US012582652B2

(12) United States Patent
Kahlig et al.

(10) Patent No.: US 12,582,652 B2
(45) Date of Patent: *Mar. 24, 2026

(54) 3-(ETHOXYDIFLUOROMETHYL)-6-(5-FLUORO-6-(2,2,2-TRIFLUOROETHOXY) PYRIDIN-3-YL)-[1,2,4]TRIAZOLO[4,3-A] PYRAZINE AS AN ION CHANNEL MODULATOR

(71) Applicant: Praxis Precision Medicines, Inc., Boston, MA (US)

(72) Inventors: Michael Kristopher Mathieu Kahlig, Redwood City, CA (US); Marion Wittmann, Medford, MA (US); Zoe A. Hughes, Newton, MA (US); Bernard Ravina, Newton, MA (US)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/927,377

(22) Filed: Oct. 25, 2024

(65) Prior Publication Data

US 2025/0049790 A1 Feb. 13, 2025

Related U.S. Application Data

(63) Continuation of application No. PCT/US2023/019652, filed on Apr. 24, 2023.

(60) Provisional application No. 63/357,944, filed on Jul. 1, 2022, provisional application No. 63/349,402, filed on Jun. 6, 2022, provisional application No. 63/335,204, filed on Apr. 26, 2022.

(51) Int. Cl.

| | |
|---|---|
| ***A61K 31/4985*** | (2006.01) |
| ***A61P 25/08*** | (2006.01) |
| ***C07D 487/04*** | (2006.01) |

(52) U.S. Cl.

CPC .......... *A61K 31/4985* (2013.01); *A61P 25/08* (2018.01)

(58) Field of Classification Search

CPC .......................... A61K 31/4985; C07D 487/04

USPC .......................................... 514/249; 544/350

See application file for complete search history.

(56) References Cited

U.S. PATENT DOCUMENTS

| | | | |
|---|---|---|---|
| 3,845,770 | A | 11/1974 | Theeuwes et al. |
| 4,112,095 | A | 9/1978 | Allen, Jr. et al. |
| 4,230,705 | A | 10/1980 | Allen, Jr. et al. |
| 4,242,515 | A | 12/1980 | Trust et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 5,905,079 | A | 5/1999 | Sargent et al. |
| 6,589,952 | B2 | 7/2003 | Bakthavatchalam et al. |
| 7,863,279 | B2 | 1/2011 | Even et al. |
| 8,030,305 | B2 | 10/2011 | Lu et al. |
| 8,173,654 | B2 | 5/2012 | Lu et al. |
| 8,198,448 | B2 | 6/2012 | Albrecht et al. |
| 8,212,041 | B2 | 7/2012 | Albrecht et al. |
| 8,217,177 | B2 | 7/2012 | Albrecht et al. |
| 8,524,900 | B2 | 9/2013 | Albrecht et al. |
| 8,937,060 | B2 | 1/2015 | Cid-Nunez et al. |
| 8,952,034 | B2 | 2/2015 | Corkey et al. |
| 9,066,954 | B2 | 6/2015 | Albrecht et al. |
| 9,371,329 | B2 | 6/2016 | Corkey et al. |
| 10,280,184 | B2 | 5/2019 | Friedman et al. |
| 11,014,931 | B2 | 5/2021 | Griffin et al. |
| 11,261,188 | B2 | 3/2022 | Reddy et al. |
| 11,278,535 | B2 | 3/2022 | Reddy et al. |
| 11,279,700 | B2 | 3/2022 | Griffin et al. |
| 11,629,146 | B2 | 4/2023 | Reddy et al. |
| 11,731,976 | B2 | 8/2023 | Griffin et al. |
| 11,731,978 | B2 | 8/2023 | Griffin et al. |
| 11,866,439 | B2 | 1/2024 | Griffin et al. |
| 2002/0049208 | A1 | 4/2002 | Bakthavatchalam et al. |

(Continued)

FOREIGN PATENT DOCUMENTS

| | | | |
|---|---|---|---|
| CA | 1080712 | A | 7/1980 |
| CN | 102725290 | A | 10/2012 |

(Continued)

OTHER PUBLICATIONS

US 8,754,103 B2, 06/2014, Corkey et al. (withdrawn)
Wilen et al., Strategies in optical resolutions. Tetrahedron. 1977;33(21):2725-2736.
Woodland et al., Discovery of Inhibitors of Trypanosoma brucei by Phenotypic Screening of a Focused Protein Kinase Library. ChemMedChem. Nov. 2015;10(11):1809-20.

(Continued)

*Primary Examiner* — Douglas M Willis
(74) *Attorney, Agent, or Firm* — McCarter & English, LLP; Jonathan M. Sparks; Yelena Margolin

(57) ABSTRACT

The present disclosure is generally directed to methods of treating a disease, disorder, or condition, e.g., a neurological disorder, a disorder associated with excessive neuronal excitability, or a disorder associated with de novo gain-of-function or loss-of-function mutations in major central nervous system sodium channel genes, such as for example, SCN1A, SCN2A, and SCN8A, using a Compound 1, or a pharmaceutically acceptable salt thereof, of the following formula:

Compound 1

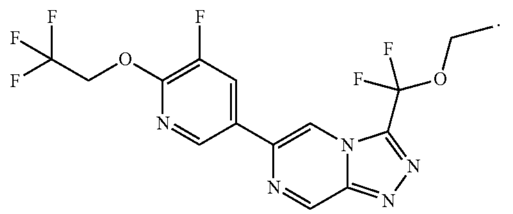

28 Claims, 24 Drawing Sheets

(56) References Cited

U.S. PATENT DOCUMENTS

| | | | |
|---|---|---|---|
| 2008/0200536 A1 | 8/2008 | Moon et al. |
| 2009/0124609 A1 | 5/2009 | Albrecht et al. |
| 2009/0203707 A1 | 8/2009 | Rajamani et al. |
| 2010/0088778 A1 | 4/2010 | Mulley et al. |
| 2011/0021521 A1 | 1/2011 | Corkey et al. |
| 2012/0010192 A1 | 1/2012 | Kobayashi et al. |
| 2012/0065191 A1 | 3/2012 | Kiss et al. |
| 2012/0245164 A1 | 9/2012 | Auger et al. |
| 2012/0245165 A1 | 9/2012 | Kang et al. |
| 2013/0315895 A1 | 11/2013 | Farrell et al. |
| 2014/0066443 A1 | 3/2014 | Beshore et al. |
| 2014/0303158 A1 | 10/2014 | Corkey et al. |
| 2015/0038503 A1 | 2/2015 | Bourotte et al. |
| 2015/0284389 A1 | 10/2015 | Pero et al. |
| 2015/0344457 A1 | 12/2015 | Duncan et al. |
| 2016/0159801 A1 | 6/2016 | Quinn et al. |
| 2016/0235718 A1 | 8/2016 | Baraban |
| 2016/0297799 A1 | 10/2016 | Brookings et al. |
| 2016/0317536 A1 | 11/2016 | Reich et al. |
| 2019/0308938 A1 | 10/2019 | McCormack et al. |
| 2019/0389868 A1 | 12/2019 | Reddy et al. |
| 2020/0179358 A1 | 6/2020 | Reddy et al. |
| 2020/0247793 A1 | 8/2020 | Reddy et al. |
| 2020/0377499 A1 | 12/2020 | Griffin et al. |
| 2020/0377506 A1 | 12/2020 | Reddy et al. |
| 2020/0377507 A1 | 12/2020 | Griffin et al. |
| 2021/0087197 A1 | 3/2021 | Griffin et al. |
| 2021/0171530 A1 | 6/2021 | Reddy et al. |
| 2021/0188839 A1 | 6/2021 | Reddy et al. |
| 2021/0355118 A1 | 11/2021 | Reddy et al. |
| 2021/0403476 A1 | 12/2021 | Reddy et al. |
| 2023/0322790 A1 | 10/2023 | Reddy et al. |
| 2023/0348466 A1 | 11/2023 | Martinez Botella et al. |
| 2024/0132501 A1 | 4/2024 | Griffin et al. |

FOREIGN PATENT DOCUMENTS

| | | | |
|---|---|---|---|
| EA | 201290121 A1 | 10/2012 |
| EA | 201991306 A1 | 3/2020 |
| EP | 2818471 A1 | 12/2014 |
| JP | 53-40798 A | 4/1978 |
| JP | 11-503437 A | 3/1999 |
| JP | 2017-1991 A | 1/2017 |
| JP | 7495962 B2 | 6/2024 |
| TW | 201116528 A | 5/2011 |
| WO | 2006/061428 A2 | 6/2006 |
| WO | 2007/075567 A1 | 7/2007 |
| WO | 2008/008539 A2 | 1/2008 |
| WO | 2010/053757 A1 | 5/2010 |
| WO | 2010/056865 A1 | 5/2010 |
| WO | 2010/074807 A1 | 7/2010 |
| WO | 2011/014462 A1 | 2/2011 |
| WO | 2011/056985 A2 | 5/2011 |
| WO | 2012/003392 A1 | 1/2012 |
| WO | 2012/065546 A1 | 5/2012 |
| WO | 2012/154760 A1 | 11/2012 |
| WO | 2013/006463 A1 | 1/2013 |
| WO | 2013/043925 A1 | 3/2013 |
| WO | 2014/179492 A1 | 11/2014 |
| WO | 2015/095370 A1 | 6/2015 |
| WO | 2015/158283 A1 | 10/2015 |
| WO | 2015/194670 A1 | 12/2015 |
| WO | 2015/197567 A1 | 12/2015 |
| WO | 2018/067786 A1 | 4/2018 |
| WO | 2018/098491 A1 | 5/2018 |
| WO | 2018/098499 A1 | 5/2018 |
| WO | 2018/098500 A1 | 5/2018 |
| WO | 2018/148745 A1 | 8/2018 |
| WO | 2018/187480 A1 | 10/2018 |
| WO | 2019/035951 A1 | 2/2019 |
| WO | 2019/232209 A1 | 12/2019 |
| WO | 2020/069322 A1 | 4/2020 |
| WO | 2021/108513 A1 | 6/2021 |
| WO | 2021/108625 A1 | 6/2021 |

OTHER PUBLICATIONS

Zablocki et al., Discovery of Dihydrobenzoxazepinone (GS-6615) Late Sodium Current Inhibitor (Late INai), a Phase II Agent with Demonstrated Preclinical Anti-Ischemic and Antiarrhythmic Properties. J Med Chem. Oct. 13, 2016;59(19):9005-9017.

Zaza et al., Pathophysiology and pharmacology of the cardiac "late sodium current.". Pharmacol Ther. Sep. 2008;119(3):326-39.

Chinese Office Action for Application No. 201780084790.8, dated Mar. 9, 2022, 23 pages.

Chinese Office Action for Application No. 201980047216.4, dated Sep. 24, 2024, 9 pages.

Eurasian Office Action for Application No. 201991306, dated Aug. 24, 2021, 6 pages.

Eurasian Office Action for Application No. 201991306, dated Feb. 25, 2021, 8 pages.

Eurasian Office Action for Application No. 202092908, dated Feb. 21, 2022, 7 pages.

European Office Action for Application No. 19810530.3, dated Feb. 23, 2023, 8 pages.

European Office Action for Application No. 19810530.6, dated Feb. 17, 2022, 1 page.

European Office Action for Application No. 19810530.6, dated Jan. 31, 2022, 9 pages.

Indian Office Action for Application No. 202017056206, dated Jun. 14, 2022, 7 pages.

International Preliminary Report on Patentability for Application No. PCT/US2017/063507, dated Jun. 6, 2019, 7 pages.

International Preliminary Report on Patentability for Application No. PCT/US2017/063533, dated Jun. 6, 2019, 8 pages.

International Preliminary Report on Patentability for Application No. PCT/US2017/063534, dated Jun. 6, 2019, 9 pages.

International Preliminary Report on Patentability for Application No. PCT/US2018/000224, dated Feb. 27, 2020, 7 pages.

International Preliminary Report on Patentability for Application No. PCT/US2018/018044, dated Aug. 22, 2019, 8 pages.

International Preliminary Report on Patentability for Application No. PCT/US2018/026099, dated Oct. 17, 2019, 7 pages.

International Preliminary Report on Patentability for Application No. PCT/US2019/034653, dated Dec. 10, 2020, 8 pages.

International Preliminary Report on Patentability for Application No. PCT/US2019/053467, dated Apr. 8, 2021, 7 pages.

International Preliminary Report on Patentability for Application No. PCT/US2020/062179, dated Jun. 9, 2022, 6 pages.

International Preliminary Report on Patentability for Application No. PCT/Us2020/062317, dated Jun. 9, 2022, 12 pages.

International Search Report and Written Opinion for Application No. PCT/US2017/063507, dated Mar. 29, 2019, 9 pages.

International Search Report and Written Opinion for Application No. PCT/US2017/063533, dated Mar. 29, 2019, 10 pages.

International Search Report and Written Opinion for Application No. PCT/US2017/063534, dated Mar. 29, 2019, 11 pages.

International Search Report and Written Opinion for Application No. PCT/US2018/000224, dated Nov. 5, 2018, 8 pages.

International Search Report and Written Opinion for Application No. PCT/US2018/018044, dated May 24, 2018, 10 pages.

International Search Report and Written Opinion for Application No. PCT/US2018/026099, dated Aug. 10, 2018, 9 pages.

International Search Report and Written Opinion for Application No. PCT/US2019/034653, dated Aug. 9, 2019, 9 pages.

International Search Report and Written Opinion for Application No. PCT/US2019/053467, dated Jan. 14, 2020, 9 pages.

International Search Report and Written Opinion for Application No. PCT/US2020/062179, dated Nov. 25, 2020, 7 pages.

International Search Report and Written Opinion for Application No. PCT/US2020/062317, dated Apr. 6, 2021, 14 pages.

International Search Report and Written Opinion for Application No. PCT/US2023/019652, dated Sep. 21, 2023, 10 pages.

International Search Report and Written Opinion for Application No. PCT/US2023/019659, dated Sep. 28, 2023, 10 pages.

Japanese Office Action for Application No. 2019-548536, dated Oct. 26, 2021, 9 pages.

(56) References Cited

OTHER PUBLICATIONS

Singapore Office Action for Application No. 11202011879R. dated May 6, 2022, 10 pages.
US Office Action for U.S. Appl. No. 16/464,483, dated Jun. 30, 2021, 22 pages.
US Office Action for U.S. Appl. No. 16/485,581, dated Mar. 10, 2021, 8 pages.
US Office Action for U.S. Appl. No. 16/500,795, dated Apr. 13, 2022, 18 pages.
US Office Action for U.S. Appl. No. 16/500,795, dated Dec. 16, 2021, 12 pages.
US Office Action for U.S. Appl. No. 16/638,725, dated Apr. 2, 2021, 8 pages.
US Office Action for U.S. Appl. No. 16/638,725, dated Dec. 11, 2020, 16 pages.
US Office Action for U.S. Appl. No. 16/885,605, dated Jan. 28, 2022, 10 pages.
US Office Action for U.S. Appl. No. 16/887,906, dated Jun. 10, 2021, 18 pages.
US Office Action for U.S. Appl. No. 17/102,586, dated Jan. 26, 2021, 14 pages.
Albright et al., Synthesis and anxiolytic activity of 6-(substituted-phenyl)-1,2,4-triazolo[4,3-b]pyridazines. J Med Chem. May 1981;24(5):592-600.
Anderson et al., Antiepileptic activity of preferential inhibitors of persistent sodium current. Epilepsia. Aug. 2014;55(8):1274-83.
Anderson et al., Unexpected Efficacy of a Novel Sodium Channel Modulator in Dravet Syndrome. Sci Rep. May 10, 2017;7(1):1682, 9 pages.
Baker et al., The novel sodium channel modulator GS-458967 (GS967) is an effective treatment in a mouse model of SCN8A encephalopathy. Epilepsia. Jun. 2018;59(6):1166-1176.
Barbieri et al., Late sodium current blocker GS967 inhibits persistent currents induced by familial hemiplegic migraine type 3 mutations of the SCN1A gene. J Headache Pain. Nov. 15, 2019;20(1):107, 13 pages.
Belardinelli et al., A novel, potent, and selective inhibitor of cardiac late sodium current suppresses experimental arrhythmias. J Pharmacol Exp Ther. Jan. 2013;344(1):23-32.
Berge et al., Pharmaceutical salts. J Pharm Sci. Jan. 1977;66(1):1-19.
Burbano et al., Characterization of a Novel Knock-in Mouse Model of KCNT1 Epileptic Encephalopathy. Neurology. Apr. 10, 2018;90(Suppl 15). Abstract P2.273.
Cannon, Analog Design. Burger's Medicional Chemistry and Drug Discovery, Fifth Edition, vol. I: Principles and Practice. Manfred E. Wolff (Ed.). John Wiley & Sons, Inc., New York. Chapter 19, pp. 783-802, (1995).
Chaplan et al., Quantitative assessment of tactile allodynia in the rat paw. J Neurosci Methods. Jul. 1994;53(1):55-63.
De Lera Ruiz et al., Voltage-Gated Sodium Channels: Structure, Function, Pharmacology, and Clinical Indications. J Med Chem. Sep. 24, 2015;58(18):7093-118.
Dorwald, Side Reactions in Organic Synthesis, A Guide to Successful Synthesis Design. Wiley-VCH Verlag GmbH & Co. KGaA. 37 pages, (2005).
Flynn et al., Correlation and prediction of mass transport across membranes. I. Influence of alkyl chain length on flux-determining properties of barrier and diffusant. J Pharm Sci. Jun. 1972;61(6):838-52.
Fukaya et al., Identification of a novel benzoxazolone derivative as a selective, orally active 18 kDa translocator protein (TSPO) ligand. J Med Chem. Oct. 24, 2013;56(20):8191-5.
Guan et al., Synthesis and anticonvulsant activity of a new 6-alkoxy-[1,2,4]triazolo[4,3-b]pyridazine. Eur J Med Chem. May 2010; 45(5):1746-52.
Hackam et al., Translation of research evidence from animals to humans. JAMA. Oct. 11, 2006;296(14):1731-2.
Jordan, Tamoxifen: a most unlikely pioneering medicine. Nat Rev Drug Discov. Mar. 2003;2(3):205-13.
Kahlig et al., The novel persistent sodium current inhibitor PRAX-562 has potent anticonvulsant activity with improved protective index relative to standard of care sodium channel blockers. Epilepsia. Mar. 2022;63(3):697-708.
Kearney et al., A gain-of-function mutation in the sodium channel gene Scn2a results in seizures and behavioral abnormalities. Neuroscience. Feb. 2001;102(2):307-17.
Kim et al., An experimental model for peripheral neuropathy produced by segmental spinal nerve ligation in the rat. Pain. Sep. 1992;50(3):355-363.
Koltun et al., Discovery of triazolopyridinone GS-462808, a late sodium current inhibitor (Late INai) of the cardiac Nav1.5 channel with improved efficacy and potency relative to ranolazine. Bioorg Med Chem Lett. Jul. 1, 2016;26(13):3207-3211.
Kolobov et al., Development of a method for the synthesis of compounds of the series 5-([1,2,4]triazolo[4,3-b] pyridazin-6-yl)benzene-1,3-diamine. Khimicheskaya Tekhnologiya. Jan. 2010;11(9):522-524.
Li et al., Antisense oligonucleotide therapy for SCN2A gain-of-function epilepsies. AES, American Epilepsy Society. 28 pages, (2018).
Patel et al., Neuropathy following spinal nerve injury shares features with the irritable nociceptor phenotype: A back-translational study of oxcarbazepine. Eur J Pain. Jan. 2019;23(1):183-197.
Petrou et al., Antisense oligonucleotide therapy for SCN2A gain-of-function epilepsies. AES, American Epilepsy Society. Retrieved online at: https://www.aesnet.org/abstractslisting/antisense-oligonucleotide-therapy-for-scn2a-gain-of-function-epilepsies. Abstract 1.466, 2 pages, (2018).
PubChem CID 58763997, 5-Phenylpyrazolo[1,5-A]pyridine. 14 pages, Mar. 10, 2018.
PubChem CID 597467, 5-Phenyl-2H-benzotriazole, 15 pages, May 12, 2018.
PubChem CID 82381512, Tuijeduithxzgl-Uhfffaoysa-N, 10 pages, Sep. 29, 2018.
PubChem CID 89077556, SCHEMBL13387345, 11 pages, Jan. 6, 2018.
STN Chemical Structure Search Results, 102 pages, May 18, 2016.
STN Chemical Structure Search Results, 107 pages, Nov. 1, 2017.
STN Chemical Structure Search Results, 123 pages, Nov. 6, 2017.
STN Chemical Structure Search Results, 22 pages, Jan. 15, 2020.
STN Chemical Structure Search Results, 23 pages, Jan. 2018.
STN Chemical Structure Search Results, 264 pages, Mar. 20, 2018.
STN Chemical Structure Search Results, 29 pages, Feb. 2018.
STN Chemical Structure Search Results, 36 pages, Apr. 14, 2019.
STN Chemical Structure Search Results, 45 pages, Apr. 23, 2019.
STN Chemical Structure Search Results, 480 pages, Mar. 6, 2017.
STN Chemical Structure Search Results, 511 pages, Mar. 6, 2017.
STN Chemical Structure Search Results, 55 pages, Apr. 2018.
STN Chemical Structure Search Results, 57 pages, Nov. 3, 2017.
STN Chemical Structure Search Results, 7 pages, Nov. 6, 2017.
STN Chemical Structure Search Results, 83 pages, Mar. 20, 2018.
STN Chemical Structure Search Results, 85 pages, Nov. 21, 2017.
STN RN 1347643-11-1, 1,2,4-Triazolo(4,3-b)pyridazine, 7-methyl-6-(4-[3-(3-piperidinyl)propoxy]phenyl). 1 page, dated Dec. 2, 2011.
Venkatesh et al., Role of the development scientist in compound lead selection and optimization. J Pharm Sci. Feb. 2000;89(2):145-54.
Wagnon et al., Convulsive seizures and SUDEP in a mouse model of SCN8A epileptic encephalopathy. Hum Mol Genet. Jan. 15, 2015;24(2):506-15.
Wang et al., Multiple Nav1.5 isoforms are functionally expressed in the brain and present distinct expression patterns compared with cardiac Nav1.5. Mol Med Rep. Jul. 2017;16(1):719-729.
Wengert et al., Prax330 reduces persistent and resurgent sodium channel currents and neuronal hyperexcitability of subiculum neurons in a mouse model of SCN8A epileptic encephalopathy. Neuropharmacology. Nov. 1, 2019;158:107699, 26 pages.
U.S. Appl. No. 16/464,468, filed May 28, 2019, U.S. Pat. No. 11,629,146, Issued.
U.S. Appl. No. 18/119,963, filed Mar. 10, 2023, 2023-0322790, Published.

(56) References Cited

OTHER PUBLICATIONS

U.S. Appl. No. 17/058,187, filed Nov. 24, 2020, U.S. Pat. No. 11,866,439, Issued.
U.S. Appl. No. 17/280,485, filed Mar. 26, 2021, 2021-0403476, Published.
U.S. Appl. No. 17/102,586, filed Nov. 24, 2020, U.S. Pat. No. 11,014,931, Issued.
U.S. Appl. No. 17/214,343, filed Mar. 26, 2021, U.S. Pat. No. 11,731,976, Issued.
U.S. Appl. No. 17/025,018, filed Mar. 23, 2022, U.S. Pat. No. 11,731,978, Issued.
U.S. Appl. No. 18/236,156, filed Aug. 21, 2023, 2024-0132501, Published.
U.S. Appl. No. 17/780,570, filed May 27, 2022, 2023-0348466, Published.
U.S. Appl. No. 18/927,451, filed Oct. 25, 2024, Pending.
U.S. Appl. No. 18/860,376, filed Oct. 25, 2024, Pending.
U.S. Appl. No. 18/860,406, filed Oct. 25, 2024, Pending.

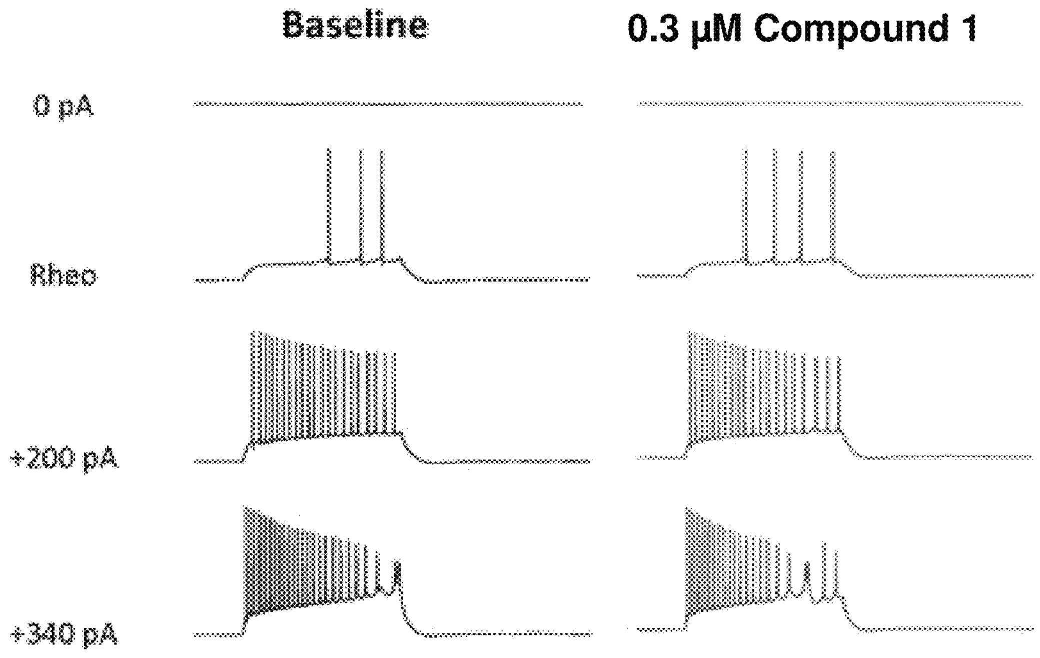
FIG. 10A
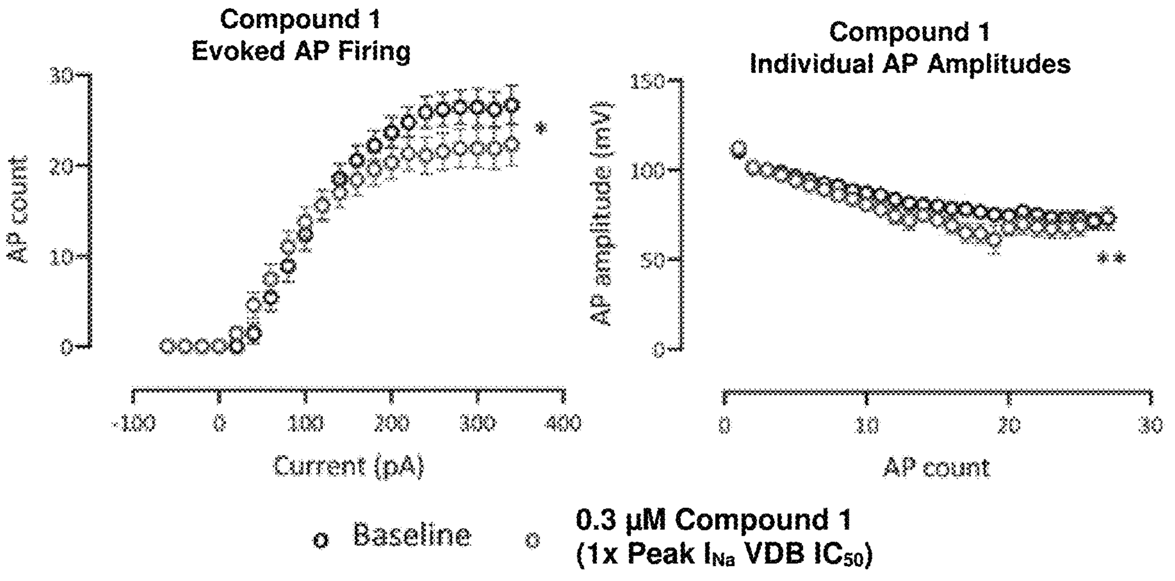
FIG. 10B
FIG. 10C

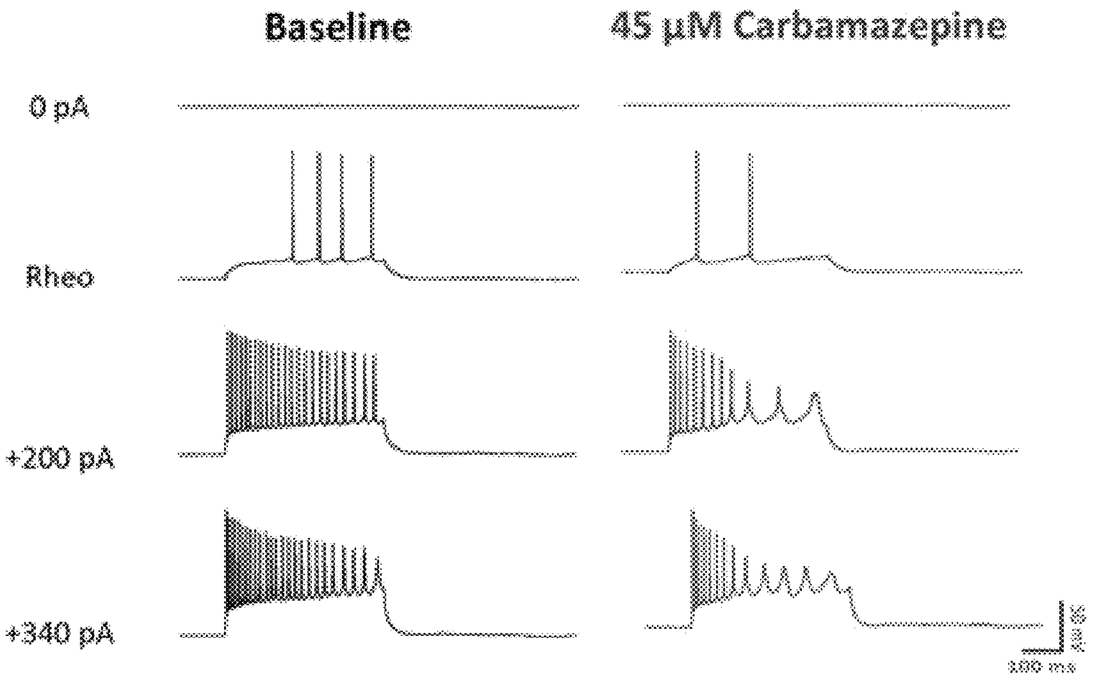
FIG. 10D
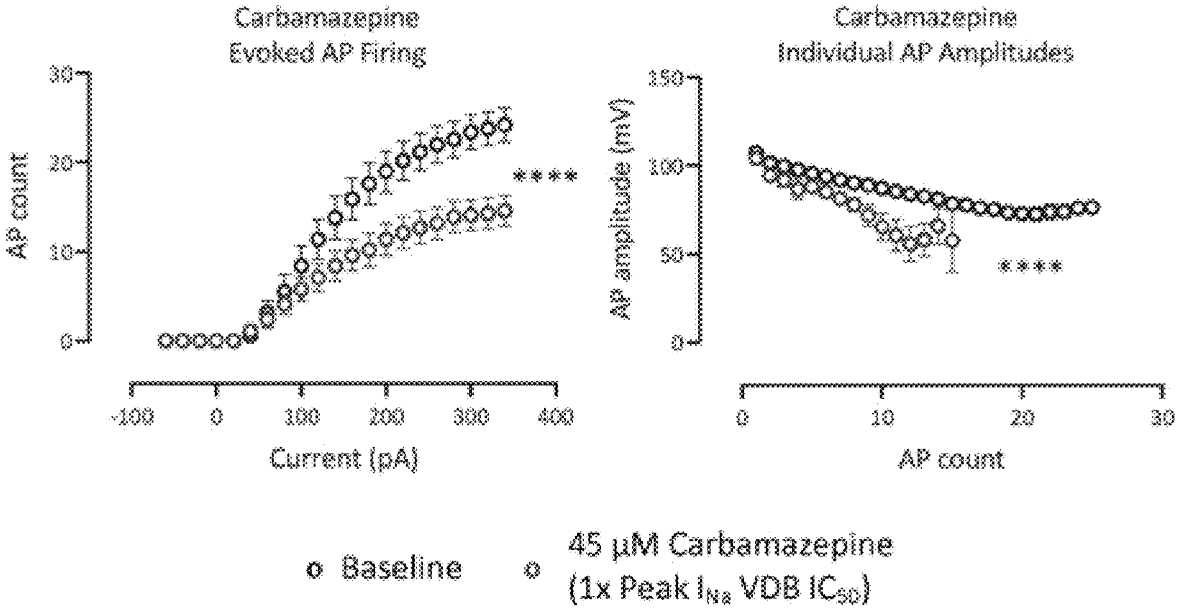
FIG. 10E
FIG. 10F

3-(ETHOXYDIFLUOROMETHYL)-6-(5-FLUORO-6-(2,2,2-TRIFLUOROETHOXY) PYRIDIN-3-YL)-[1,2,4]TRIAZOLO[4,3-A] PYRAZINE AS AN ION CHANNEL MODULATOR

RELATED APPLICATIONS

This application is a continuation of International Application No. PCT/US2023/019652, filed on Apr. 24, 2023; which claims the benefit of priority to U.S. Provisional Application No. 63/335,204, filed on Apr. 26, 2022; U.S. Provisional Application No. 63/349,402, filed on Jun. 6, 2022 and U.S. Provisional Application No. 63/357,944, filed on Jul. 1, 2022. The entire contents of each of the foregoing applications are hereby incorporated herein by reference.

FIELD OF THE DISCLOSURE

The present disclosure is generally directed to methods of treating a disease, disorder, or condition, e.g., a neurological disorder, a disorder associated with excessive neuronal excitability, or a disorder associated with de novo gain-of-function or loss-of-function mutations in central nervous system sodium channel genes, such as for example, SCN1A, SCN2A, and SCN8A.

BACKGROUND OF THE DISCLOSURE

Sodium ion ($Na^+$) channels primarily open in a transient manner and are quickly inactivated, thereby generating a fast $Na^+$ current to initiate the action potential. The late or persistent sodium current ($I_{Na}L$) is a sustained component of the fast $Na^+$ current of cardiac myocytes and neurons. Many common neurological and cardiac conditions are associated with abnormal $I_{Na}L$ enhancement, which contributes to the pathogenesis of both electrical and contractile dysfunction in mammals (see e.g., Pharmacol. Ther., 2008, 119:326-339).

Epilepsy is the fourth most common neurological disorder, affecting 3.4 million people in the United States, including 470,000 children. Epilepsy is a group of heterogeneous disorders classified into distinct syndromes by etiology, seizure type(s), and comorbidities. The most common cause of genetic epilepsy is mutations within voltage-gated sodium channel ($Na_V$) genes leading to gain-of-function and/or loss-of-function changes in channel activity. Affected patients typically present as children or neonates and have prognoses ranging from benign seizures that spontaneously remit to devastating developmental and epileptic encephalopathies (DEEs).

$Na_V$ channels are an important therapeutic target for antiepileptic drugs (AEDs). Their blockade, and consequent inhibition of neuronal sodium current ($I_{Na}$), is ideally positioned to reduce excitability, as peak $I_{Na}$ in the axonal initial segment and node of Ranvier is responsible for the initiation and propagation of action potentials (APs), respectively. However, the clinical utility of standard $Na_V$-targeting AEDs is limited because current agents, including carbamazepine (CBZ), oxcarbazepine, and phenytoin, can show severe toxicity at therapeutic doses. This toxicity includes ataxia, lethargy, vomiting, and seizures and reflects compromised physiologic neuronal function resulting from excessive peak $I_{Na}$ inhibition or off-target (non-$Na_V$-mediated) activities. Identification of novel $I_{Na}$ inhibitors with improved tolerability would thus represent a clinically meaningful alternative treatment option.

Physiological persistent $I_{Na}$ is a small, subthreshold current that contributes to the amplification of synaptic responses and the enhancement of repetitive firing. Functional studies of SCN2A (encoding $Na_V1.2$) and SCN8A (encoding $Na_V1.6$) DEE variants have demonstrated small increases in persistent $I_{Na}$ that can cause hyperexcitability, seizures, and developmental comorbidities. Current $Na_V$-targeting AEDs are predicted to inhibit both peak $I_{Na}$ and persistent $I_{Na}$ at or near therapeutic concentrations (high μmol/L range), with excessive peak $I_{Na}$ inhibition compromising physiological neuronal activity. Therefore, improved selectivity for $Na_V$ activity and preference in the targeting of persistent $I_{Na}$ could meaningfully improve tolerability.

Accordingly, additional therapeutic options with improved efficacy and tolerability to treat epilepsy, to achieve seizure freedom, or both, are needed.

SUMMARY OF THE DISCLOSURE

Disclosed herein are methods of treating a disease, disorder, or condition, e.g., a neurological disorder, a disorder associated with excessive neuronal excitability and/or abnormal late sodium current, or a disorder associated with de novo gain-of-function (GoF) or loss-of-function mutations (variants) in major central nervous system sodium channel genes, such as for example, SCN1A, SCN2A, and SCN8A, by administering to a subject in need thereof a therapeutically effective amount of a compound of Formula (I):

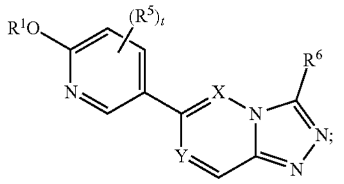

(I)

or a pharmaceutically acceptable salt thereof, wherein:

X and Y are each independently $CR^d$ or N;

$R^1$ is

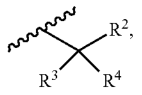

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

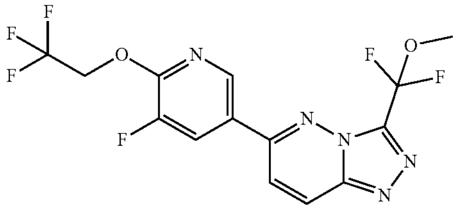

or

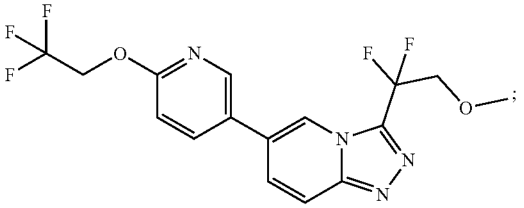

or a pharmaceutically acceptable salt thereof.

In some embodiments, the compound is a compound of Formula (I-a):

(I-a)

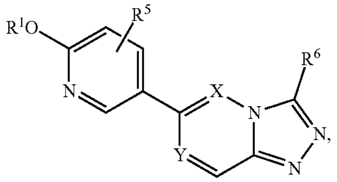

or a pharmaceutically acceptable salt thereof, wherein the variables are as defined herein.

In some embodiments, the compound is a compound of Formula (I-b):

(I-b)

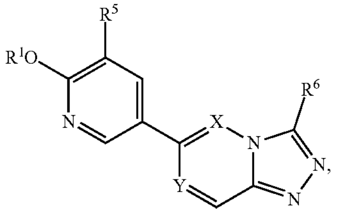

or a pharmaceutically acceptable salt thereof, wherein the variables are as defined herein.

In some embodiments, the compound is a compound of Formula (I-c):

(I-c)

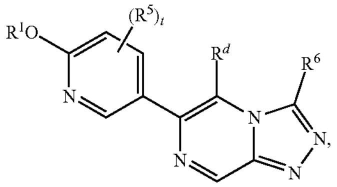

or a pharmaceutically acceptable salt thereof, wherein the variables are as defined herein.

In some embodiments, the compound is a compound of Formula (II):

(II)

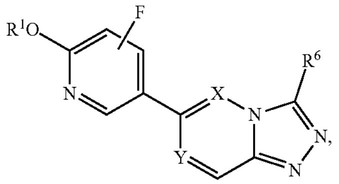

or a pharmaceutically acceptable salt thereof, wherein the variables are as defined herein.

In some embodiments, the compound is a compound of Formula III:

(III)

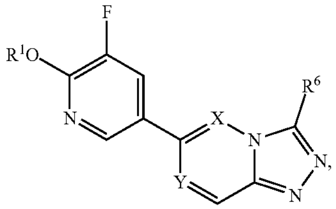

or a pharmaceutically acceptable salt thereof, wherein the variables are as defined herein.

In some embodiments, the compound is a compound of Formula IV:

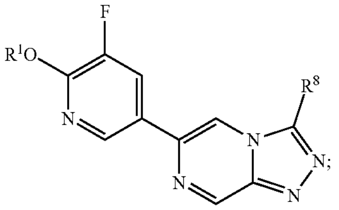

or a pharmaceutically acceptable salt thereof, wherein the variables are as defined herein.

In some embodiments, the compound is Compound 1 having the following formula:

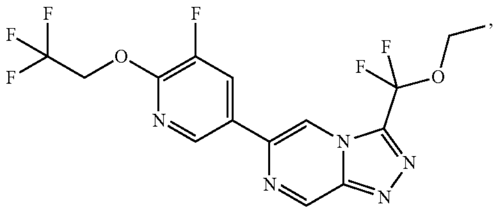

or a pharmaceutically acceptable salt thereof.

In some embodiments, the method provided involves treating a disorder associated with excessive neuronal excitability. In some embodiments, the disorder is epilepsy, an epilepsy syndrome, or an encephalopathy, such as a genetic or pediatric epilepsy or a genetic or pediatric epilepsy syndrome. In some embodiments, the disorder is developmental and epileptic encephalopathies. In some embodiments, the disorder is Tuberous Sclerosis Complex (TSC).

In some embodiments, the method reduces frequency of seizures experienced by the subject within 24 hours after administration of the compound or a pharmaceutically acceptable salt thereof as compared to the frequency of seizures prior to the administration.

In some embodiments, the compound of the disclosure, or a pharmaceutically acceptable salt thereof, is administered to the subject in an amount ranging from about 0.1 mg/kg to about 1 g/kg. In other embodiments, the compound or a pharmaceutically acceptable salt thereof is administered to the subject in an amount ranging from about 10 mg/kg to about 100 mg/kg, such as about 30 mg/kg.

In some embodiments, the compound of the disclosure, or a pharmaceutically acceptable salt thereof, is administered to the subject in an amount ranging from about 2.5 mg to about 150 mg per day, such as about 90 mg or about 120 mg per day. In some embodiments, the compound of the disclosure, or a pharmaceutically acceptable salt thereof, is administered to the subject as multiple doses in an amount ranging from about 30 mg to about 120 mg per day.

In some embodiments, the compound of the disclosure, or a pharmaceutically acceptable salt thereof, is administered to the subject orally. In some embodiments, the compound of the disclosure, or a pharmaceutically acceptable salt thereof, is administered to the subject every day for at least 14 days. In some embodiments, the compound of the disclosure, or a pharmaceutically acceptable salt thereof, is administered to the subject in a fasted state. In some embodiments, the compound of the disclosure, or a pharmaceutically acceptable salt thereof, is administered to the subject in a fed state.

In some embodiments, the subject is human. In some embodiments, the subject is a human of 2 to 17 years of age.

In some aspects, the present disclosure provides a method of treating a condition relating to aberrant function of a sodium ion channel in a subject in need thereof, said method comprising administering to said subject a compound of Formula (I):

(I)

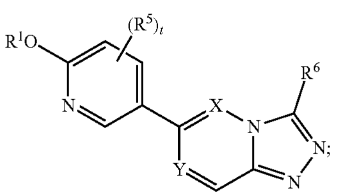

or a pharmaceutically acceptable salt thereof, at a dose of about 1 mg to about 150 mg; wherein:

X and Y are each independently $CR^d$ or N;

$R^1$ is

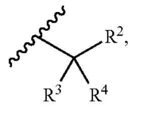

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

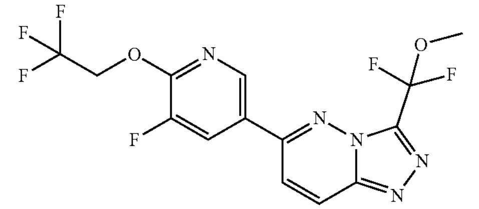

or

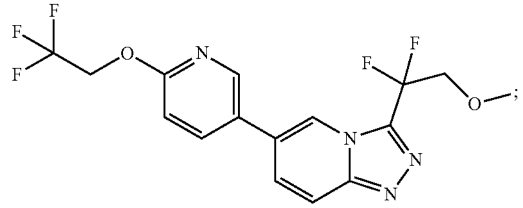

or a pharmaceutically acceptable salt thereof.

In some embodiments, the compound is administered at a dose of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg or about 150 mg.

In some aspect, s the present disclosure provides a method of treating a condition relating to aberrant function of a sodium ion channel in a subject in need thereof, said method comprising administering to said subject a compound of Formula (I):

(I)

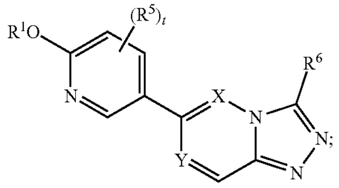

or a pharmaceutically acceptable salt thereof, at a dose of about 0.25 mg/kg/day to about 1 mg/kg/day; wherein:

X and Y are each independently $CR^d$ or N;

$R^1$ is

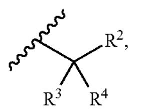

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

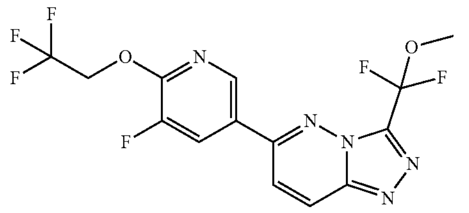

or

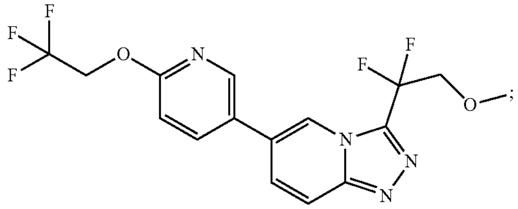

;

or a pharmaceutically acceptable salt thereof.

In some embodiments, the compound is administered at a dose of about 0.25 mg/kg/day, about 0.30 mg/kg/day, about 0.35 mg/kg/day, about 0.40 mg/kg/day, about 0.45 mg/kg/day, about 0.50 mg/kg/day, about 0.55 mg/kg/day, about 0.60 mg/kg/day, about 0.65 mg/kg/day, about 0.65 mg/kg/day, about 70 mg/kg/day, about 0.75 mg/kg/day, about 0.80 mg/kg/day, about 0.85 mg/kg/day, about 0.90 mg/kg/day, about 0.95 mg/kg/day or about 1.0 mg/kg/day.

In some embodiments, the administration of the compound results in a reduction in the severity, number and/or frequency of seizures experienced by the subject as compared to the severity, number and/or frequency of seizures experienced by the subject prior to administration of the compound.

In some embodiments, the administration of the compound does not result in ataxia, lethargy and vomiting in the subject.

In some aspects, the present disclosure provides a method of reducing severity, number and/or frequency of seizures in a subject in need thereof, said method comprising administering to said subject an effective amount of a compound of Formula (I):

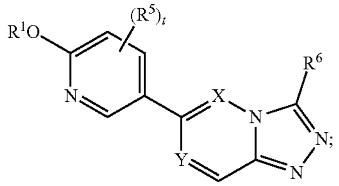

(I)

or a pharmaceutically acceptable salt thereof, wherein:

X and Y are each independently $CR^d$ or N;

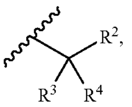

$R^1$ is monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

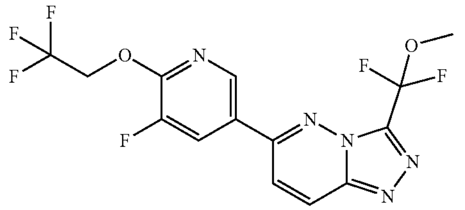

or

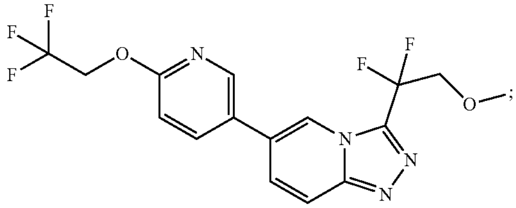

;

or a pharmaceutically acceptable salt thereof.

In some embodiments, the the subject has a condition relating to aberrant function of a sodium ion channel. In some embodiments, the condition relating to aberrant function of a sodium ion channel is a neurological disorder. In some embodiments, the neurological disorder is a disorder associated with excessive neuronal excitability. In some embodiments, the neurological disorder is associated with one or more de novo gain-of-function or loss-of-function mutations in central nervous system sodium ion channel genes.

In some embodiments, the condition is epilepsy, an epilepsy syndrome or encephalopathy. In some embodiments, the condition is a genetic epilepsy or a genetic epilepsy syndrome. In some embodiments, the condition is pediatric epilepsy or a pediatric epilepsy syndrome.

In some embodiments, the condition is selected from the group consisting of malignant migrating focal seizures of infancy (MMFSI), epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox-Gastaut syndrome, seizures, leukodystrophy, leukoencephalopathy, intellectual disability, multifocal epilepsy, drug-resistant epilepsy, temporal lobe epilepsy and cerebellar ataxia. In some embodiments, the condition is epileptic encephalopathy.

In some embodiments, the condition is selected from the group consisting of epileptic encephalopathy with SCN1A, SCN2A and/or SCN8A mutation, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, Rasmussen encephalitis, malignant migrating partial seizures of infancy, autosomal dominant nocturnal frontal lobe epilepsy, KCNQ2 epileptic encephalopathy and KCNT1 epileptic encephalopathy.

In some embodiments, the condition is Tuberous Sclerosis Complex (TSC).

In some embodiments, the compound is of Formula (I-a):

(I-a)

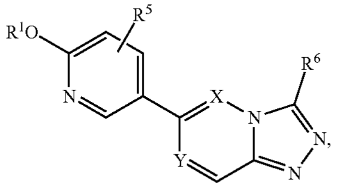

or a pharmaceutically acceptable salt thereof.

In some embodiments, the compound is of Formula (I-b):

(I-b)

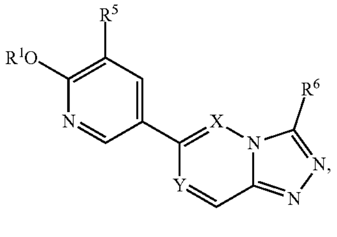

or a pharmaceutically acceptable salt thereof.

In some embodiments, the compound is of Formula (I-c):

(I-c)

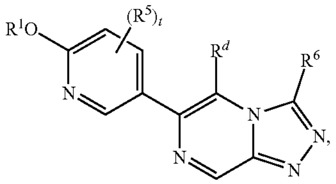

or a pharmaceutically acceptable salt thereof.

In some embodiments, the compound is of Formula (II):

(II)

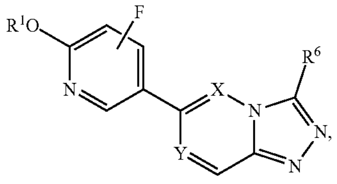

or a pharmaceutically acceptable salt thereof.

In some embodiments, the compound is of Formula III:

(III)

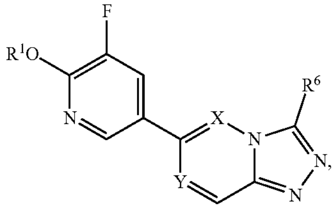

or a pharmaceutically acceptable salt thereof.

In some embodiments, the compound is of Formula IV:

(IV)

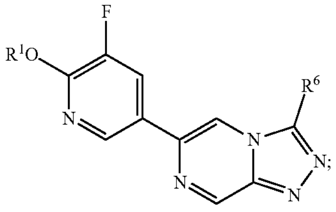

or a pharmaceutically acceptable salt thereof.

In some embodiments, the compound is Compound 1 of the following formula:

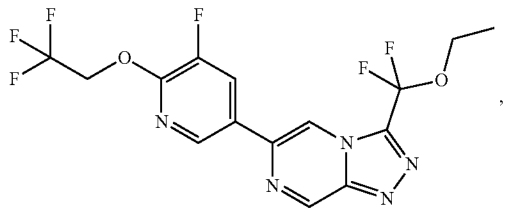 [SMILES: CCOC(F)(F)c1nnc2cnc(-c3cnc(OCC(F)(F)F)c(F)c3)cn12]

or a pharmaceutically acceptable salt thereof.

In some aspects, the present disclosure also provides a method of preferentially inhibiting persistent sodium current ($I_{Na}$) over peak sodium current ($I_{Na}$) in a neuron, said method comprising contacting said neuron with an effective amount of a compound of Formula (I):

(I)

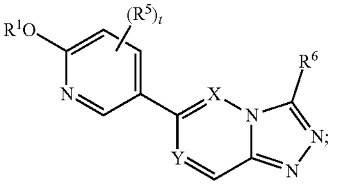

or a pharmaceutically acceptable salt thereof, wherein:

X and Y are each independently $CR^d$ or N;

$R^1$ is

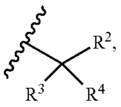

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

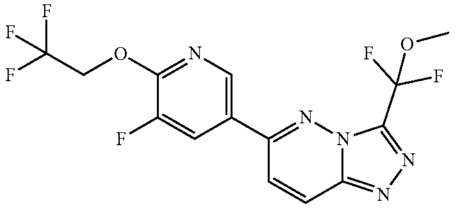

or

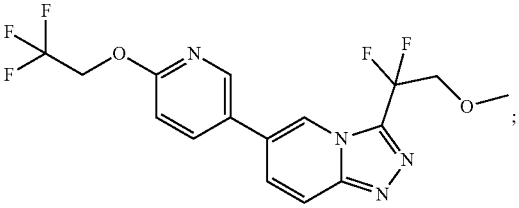

;

or a pharmaceutically acceptable salt thereof.

In some embodiments, the neuron is in a subject.

In some embodiments, the subject has a condition relating to aberrant function of a sodium ion channel. In some embodiments, the condition relating to aberrant function of a sodium ion channel is a neurological disorder. In some embodiments, the neurological disorder is a disorder associated with excessive neuronal excitability. In some embodiments, the neurological disorder is associated with one or more de novo gain-of-function or loss-of-function mutations in central nervous system sodium ion channel genes.

In some embodiments, the condition is epilepsy, an epilepsy syndrome or encephalopathy. In some embodiments, the condition is a genetic epilepsy or a genetic epilepsy syndrome. In some embodiments, the condition is a pediatric epilepsy or a pediatric epilepsy syndrome.

In some embodiments, the condition is selected from the group consisting of malignant migrating focal seizures of infancy (MMFSI), epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox-Gastaut syndrome, seizures, leukodystrophy, leukoencephalopathy, intellectual disability, multifocal epilepsy, drug-resistant epilepsy, temporal lobe epilepsy and cerebellar ataxia. In some embodiments, the condition is epileptic encephalopathy.

In some embodiments, the condition is selected from the group consisting of epileptic encephalopathy with SCN1A, SCN2A and/or SCN8A mutation, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, Rasmussen encephalitis, malignant migrating partial seizures of infancy, autosomal dominant nocturnal frontal lobe epilepsy, KCNQ2 epileptic encephalopathy and KCNT1 epileptic encephalopathy.

In some embodiments, the condition is Tuberous Sclerosis Complex (TSC).

In some embodiments, the compound is of Formula (I-a):

(I-a)

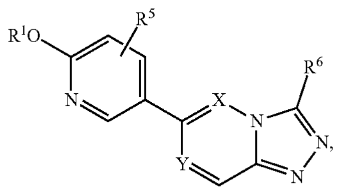

or a pharmaceutically acceptable salt thereof.

In some embodiments, the compound is of Formula (I-b):

(I-b)

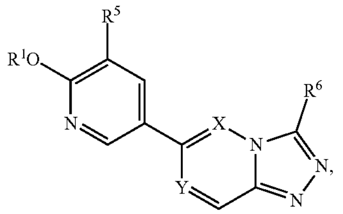

or a pharmaceutically acceptable salt thereof.

In some embodiments, the compound is of Formula (I-c):

(I-c)

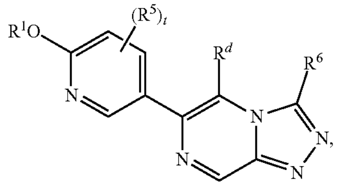

or a pharmaceutically acceptable salt thereof.

In some embodiments, the compound is of Formula (II):

(II)

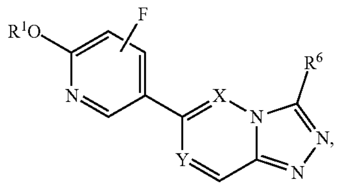

or a pharmaceutically acceptable salt thereof.

In some embodiments, the compound is of Formula III:

(III)

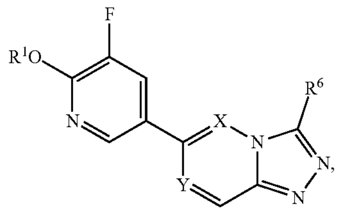

or a pharmaceutically acceptable salt thereof.

In some embodiments, the compound is of Formula IV:

(IV)

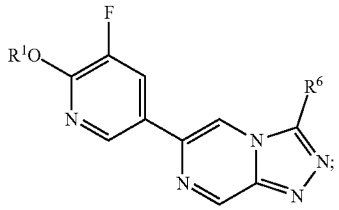

or a pharmaceutically acceptable salt thereof.

In some embodiments, the compound is Compound 1 of the following formula:

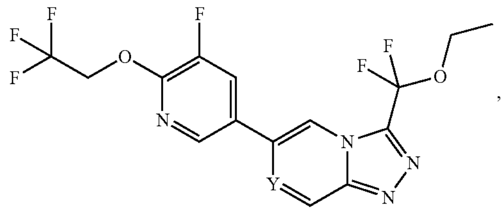

or a pharmaceutically acceptable salt thereof.

In some embodiments, the subject is a human.

BRIEF DESCRIPTION OF THE DRAWINGS

The accompanying drawings, which are incorporated in and constitute a part of this specification, illustrate certain embodiments, and together with the written description, serve to explain certain principles of the methods and devices disclosed herein.

FIG. 1A: Representative action potential traces from CA1 pyramidal neurons during baseline recording and following the application of 3 μM Compound 1. FIG. 1B: Compound 1 at both 0.3 and 3 μM significantly reduced the action potential firing frequency in CA1 pyramidal neurons from wildtype mice.

FIG. 7A: Effect of Compound 1 in KCNQ2 K556E PTZ seizure model. FIG. 7B: Effect of Compound 1 in KCNC1 R320H PTZ seizure model.

(FIG. 8B). FIG. 8C: Compound 1 demonstrated increased potency for persistent $I_{Na}$ relative to standard $Na_V$-targeting antiepileptic drugs. FIG. 8D: Compound 1 inhibited ATX-II- or N1768D-induced persistent $I_{Na}$ expressed by multiple $Na_V$ isoforms and orthologs. Voltage protocols are included as panel insets, pharmacology was measured at arrowhead, and points represent mean±SEM. NMDG, N-methyl-D-glucamine.

FIG. 9A), use-dependent block (rate/activity dependent; FIG. 9B), or voltage-dependent block (depolarization dependent; FIG. 9C). FIG. 9D: Compound 1 demonstrates preference for persistent $I_{Na}$ relative to peak $I_{Na}$ for all assay conditions (red arrow). CBZ (FIG. 9E) and LTG (FIG. 9F) exhibited lower potency and no preference for persistent $I_{Na}$ (red arrows). Voltage protocols are included as panel insets, pharmacology was measured at blue arrowheads, and points represent mean±SEM.

FIGS. 10A-10F depict that Compound 1 reduces intrinsic excitability of hippocampal CA1 pyramidal neurons without compromising action potential (AP) amplitude. The effect is shown of Compound 1 (blue) and carbamazepine (CBZ; red) at equivalent effective concentrations (half-maximal inhibitory concentration [$IC_{50}$] of peak sodium current [$I_{Na}$] voltage-dependent block [VDB]) on AP firing recorded from CA1 pyramidal neurons from wild-type mice. Representative AP traces show the predrug (black, baseline) and after-drug records for 0.3 μmol/L Compound 1 (FIG. 10, blue) or 45 μmol/L CBZ (FIG. 10, red). Input-output relationships (FIG. 10B and FIG. 10E) and AP amplitude adaptation (FIG. 10C and FIG. 10F) for Compound 1 and CBZ at a current injection of +200 pA. Data are presented as mean±SEM. *p<0.05, p<0.01, **p<0.0001.

FIG. 11C: Compound 1 (10-40 mg/kg po) produced dose-dependent reductions in distance moved in the spontaneous locomotor activity (sLMA) assay. FIG. 11D: Total brain concentrations of Compound 1 associated with anticonvulsant efficacy (green symbols, left y-axis) were separated from those associated with decreases in total distance moved (red symbols, right y-axis). FIG. 11E: The range of calculated free brain concentrations of Compound 1, CBZ, and LTG associated with anticonvulsant effects (green bars) and reductions in locomotor activity (red bars) are shown. PIs for each molecule are shown. Data presented as mean±SEM. MES: n=12-24/group, analysis of variance (ANOVA)/Dunn test; sLMA: n=20/group, ANOVA/Dunnett test. *p<0.05 versus vehicle (Veh), **p<0.01 versus Veh.

DETAILED DESCRIPTION OF THE DISCLOSURE

Figure 1A:
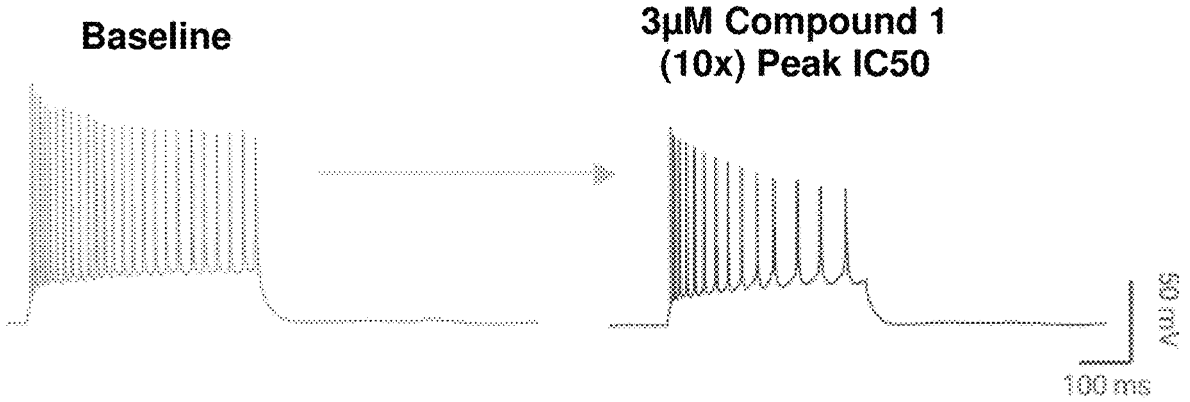
FIGS. 1A-1B depict the effect of Compound 1 at 0.3 or 3 μM on action potential firing from wildtype CA1 pyramidal neurons.

Reference will now be made in detail to various exemplary embodiments, examples of which are illustrated in the accompanying drawings. It is to be understood that the following detailed description is provided to give the reader a fuller understanding of certain embodiments, features, and details of aspects of the disclosure, and should not be interpreted as a limitation of the scope of the disclosure.

Definitions

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The term "about" is used herein to mean within the typical ranges of tolerances in the art. For example, "about" can be understood as about 2 standard deviations from the mean. According to certain embodiments, when referring to a measurable value such as an amount and the like, "about" is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value as such variations are appropriate to perform the disclosed methods and/or to make and use the disclosed devices. When "about" is present before a series of numbers or a range, it is understood that "about" can modify each of the numbers in the series or range.

The terms "administer," "administering" or "administration" as used herein refer to either directly administering a compound or pharmaceutically acceptable salt or ester of the compound or a composition comprising the compound or pharmaceutically acceptable salt or ester of the compound to a subject.

The term "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "at least" prior to a number or series of numbers (e.g., "at least two") is understood to include the number adjacent to the term "at least," and all subsequent numbers or integers that could logically be included, as clear from context. When "at least" is present before a series of numbers or a range, it is understood that "at least" can modify each of the numbers in the series or range.

The terms "disease," "disorder," and "condition" are used interchangeably herein.

As used herein, the term "in some embodiments" refers to embodiments of all aspects of the disclosure, unless the context clearly indicates otherwise.

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, a "subject" to which administration is contemplated includes, but is not limited to, humans (i.e., a male or female of any age group, e.g., a fetus, a pediatric subject (such as an infant, a child, or an adolescent) or an adult subject (e.g., a young adult, a middle-aged adult or a senior adult) and/or a non-human animal, e.g., a mammal such as a primate (e.g., a cynomolgus monkey or a rhesus monkey), a cattle, a pig, a horse, a sheep, a goat, a rodent, a cat, and/or a dog. In certain embodiments, the subject is a human. In certain embodiments, the subject is a non-human animal.

As used herein, the terms "treat", "treatment" or "treating" a condition or a disorder, e.g., epilepsy or an epilepsy syndrome, such as focal epilepsy, in a subject in need thereof includes achieving, partially, substantially or completely, one or more of the following: ameliorating, improving or achieving a reduction in the severity of at least one symptom or indicator associated with the condition or disorder; or arresting the progression or worsening of the condition or disorder.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described, for example, in Thomas Sorrell, Organic Chemistry, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-1}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to. 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

"Hetero" when used to describe a compound or a group present on a compound means that one or more carbon atoms in the compound or group have been replaced by a nitrogen, oxygen, or sulfur heteroatom. Hetero may be applied to any of the alkyl groups described above such as alkyl, e.g., heteroalkyl; alkenyl, e.g., heteroalkenyl; alkynyl, e.g., heteroalkynyl; carbocyclyl, e.g., heterocyclyl; aryl, e.g., heteroaryl, and the like having from 1 to 5, and particularly from 1 to 3 heteroatoms.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-5}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spire ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Cyano" refers to —CN.

"Halo" or "halogen" refers to a fluorine atom (i.e., fluoro or —F), a chlorine atom (i.e., chloro or —Cl), a bromine atom (i.e., bromo or —Br), and an iodine atom (i.e., iodo or —I). In certain embodiments, the halo group is fluoro or chloro.

"Haloalkyl" refers to an alkyl group substituted with one or more halogen atoms.

"Nitro" refers to —$NO_2$.

In general, the term "substituted," whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

The embodiments disclosed herein are not intended to be limited in any manner by the above exemplary listing of chemical groups and substituents. Those skilled in the art will recognize that several embodiments are possible within the scope and spirit of the present disclosure. The following description illustrates the disclosure and, of course, should not be construed in any way as limiting the scope of the inventions described herein

Compounds and Compositions

In one aspect, provided herein is a compound of Formula (I):

(I)

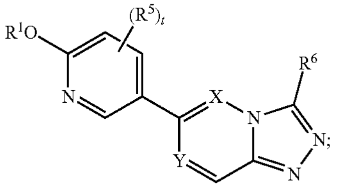

or a pharmaceutically acceptable salt thereof, wherein:

X and Y are each independently $CR^d$ or N;

$R^1$ is

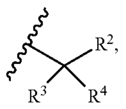

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy, $R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl;

provided the compound is not a compound having the formula:

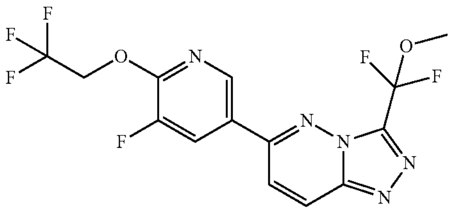

or

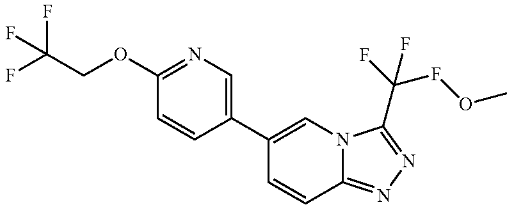

;

or a pharmaceutically acceptable salt thereof.

In some embodiments, the compound is a compound of Formula (I-a):

(I-a)

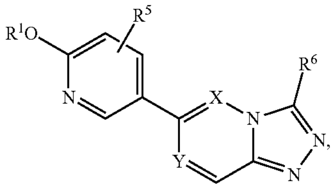

or a pharmaceutically acceptable salt thereof, wherein the variables are as defined herein.

In some embodiments, the compound is a compound of Formula (I-b):

(I-b)

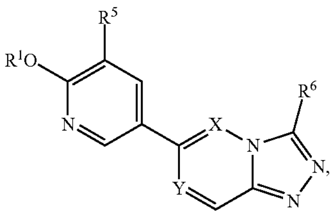

or a pharmaceutically acceptable salt thereof, wherein the variables are as defined herein.

In some embodiments, the compound is a compound of Formula (I-c):

(I-c)

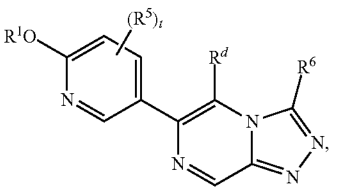

or a pharmaceutically acceptable salt thereof, wherein the variables are as defined herein.

In some embodiments, the compound is a compound of Formula (II):

(II)

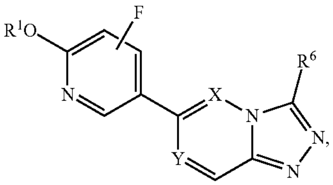

or a pharmaceutically acceptable salt thereof, wherein the variables are as defined herein.

In some embodiments, the compound is a compound of Formula III:

(III)

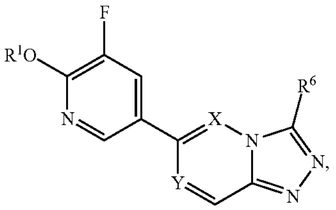

or a pharmaceutically acceptable salt thereof, wherein the variables are as defined herein.

In some embodiments, the compound is a compound of Formula IV:

(IV)

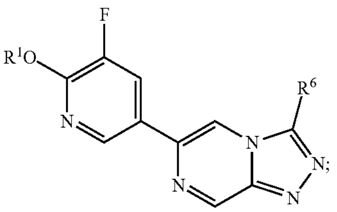

or a pharmaceutically acceptable salt thereof, wherein the variables are as defined herein.

In some embodiments, the compound is Compound 1 having the following formula:

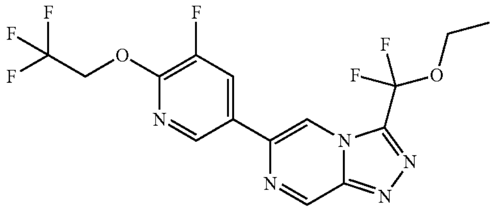

, or a pharmaceutically acceptable salt thereof.

In some embodiments, Compound 1 is in a crystalline form. In some embodiments, the crystalline form may be characterized by an X-ray powder diffraction pattern comprising X-ray powder diffraction peaks at the following diffraction angles (° 2θ): 9.3±0.2, 18.8±0.2, and 21.4±0.2. In some embodiments, the crystalline form may be characterized by an X-ray powder diffraction pattern comprising X-ray powder diffraction peaks at the following diffraction angles (° 2θ): 16.1±0.2, 21.1±0.2 and 21.6±0.2. In some embodiments, the crystalline form may be characterized by an X-ray powder diffraction pattern comprising X-ray powder diffraction peaks at the following diffraction angles (° 2θ): 9.3±0.2, 16.1±0.2, 18.8±0.2, 21.1±0.2, 21.4±0.2, and 21.6±0.2. In some embodiments, the crystalline form may be characterized by an X-ray powder diffraction pattern comprising X-ray powder diffraction peaks at the following diffraction angles (° 2θ): 16.1±0.2, 21.1±0.2, 21.6±0.2, 22.6±0.2, 23.9±0.2, 26.0±0.2, and 26.4±0.2. In some embodiments, the crystalline form may be characterized by an X-ray powder diffraction pattern comprising X-ray powder diffraction peaks at the following diffraction angles (° 2θ): 9.3±0.2, 16.1±0.2, 18.8±0.2, 21.1±0.2, 21.4±0.2, 21.6±0.2, 22.6±0.2, 23.9±0.2, 26.0±0.2, and 26.4±0.2. The crystalline form of Compound 1 is described, e.g., in WO 2019/232209, the entire contents of which are hereby incorporated herein by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomers. Isomers can be isolated from mixtures by methods known to those skilled in the art, including chiral high pressure liquid chromatography (HPLC) and the formation and crystallization of chiral salts; preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). Embodiments disclosed herein additionally encompass compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than about 75% by weight, such as more than about 80% by weight, more than about 85% by weight, more than about 90% by weight, more than about 91% by weight, more than about 92% by weight, more than about 93% by weight, more than about 94% by weight, more than about 95% by weight, more than about 96% by weight, more than about 97% by weight, more than about 98% by weight, more than about 98.5% by weight, more than about 99% by weight, more than about 99.2% by weight, more than about 99.5% by weight, more than about 99.6% by weight, more than about 99.7% by weight, more than about 99.8% by weight, or more than about 99.9% by weight, of the enantiomer. In certain embodiments, the weights are based upon total weight of all enantiomers or stereoisomers of the compound.

In certain aspects, provided are compositions comprising the compounds described herein, such as Compound 1. In some embodiments, the composition is a pharmaceutical composition comprising the compound described herein, such as Compound 1, and a pharmaceutically acceptable carrier. In some embodiments, the compound comprised in the disclosed composition is a compound of Formula (I) or a pharmaceutically acceptable salt thereof as defined elsewhere herein. In some embodiments, the compound comprised in the disclosed composition is a compound of Formula (I-a) or a pharmaceutically acceptable salt thereof as defined elsewhere herein. In some embodiments, the compound comprised in the disclosed composition is a compound of Formula (I-b) or a pharmaceutically acceptable salt thereof as defined elsewhere herein. In some embodiments, the compound comprised in the disclosed composition is a compound of Formula (I-c) or a pharmaceutically acceptable salt thereof as defined elsewhere herein. In some embodiments, the compound comprised in the disclosed composition is a compound of Formula (II) or a pharmaceutically acceptable salt thereof as defined elsewhere herein. In some embodiments, the compound comprised in the disclosed composition is a compound of Formula (III) or a pharmaceutically acceptable salt thereof as defined elsewhere herein. In some embodiments, the compound comprised in the disclosed composition is a compound of Formula (IV) or a pharmaceutically acceptable salt thereof as defined elsewhere herein. In some embodiments, the compound comprised in the disclosed composition is Compound 1 having the following formula:

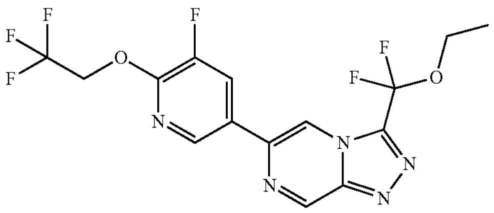
, or a pharmaceutically acceptable salt thereof.

In some embodiments, an enantiomerically pure compound can be present in the compositions with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise at least about 95% by weight S-compound and at most about 5% by weight R-compound, by total weight of the compound. In certain embodiments, the active ingredient can be formulated with little or no excipient or carrier.

Compounds described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$. O may be in any isotopic form, including $^{16}O$ and $^{18}O$, and F may be in any isotopic form, including $^{18}F$ and $^{19}F$.

Methods of Treatment

Compounds and compositions described herein are generally useful for the modulating the activity of sodium channels and are useful in treating conditions relating to aberrant function of a sodium channel ion channel, e.g., abnormal late sodium ($I_{Na}L$) current. In some embodiments, a compound provided by the disclosure is effective in the treatment of epilepsy or an epilepsy syndrome, a neurodevelopmental disorder, pain, or a neuromuscular disorder. A provided compound, pharmaceutically acceptable salt thereof, or composition comprising the same may also modulate all sodium ion channels, or may be specific to only one or a plurality of sodium ion channels, e.g., $Na_V1.1$, 1.2, 1.3, 1.4, 1.5, 1.6, 1.7, 1.8, and/or 1.9. In some embodiments, a compound of the disclosure has specificity to sodium ion channel $Na_V1.6$. In some embodiments, a compound of the disclosure is a pan-$Na_V$ blocker, with specificity against all or substantially all of the sodium ion channels (e.g., all or substantially all of $Na_V1.1$, 1.2, 1.3, 1.4, 1.5, 1.6, 1.7, 1.8, and 1.9).

In typical embodiments, the disclosure is intended to encompass the compounds disclosed herein, and the pharmaceutically acceptable salts, pharmaceutically acceptable esters, tautomeric forms, polymorphs, and prodrugs of such compounds. In some embodiments, the disclosure includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I), (I-a), (I-b), (I-c), (II), (III), or (IV), or Compound 1).

The compounds and compositions described herein, such as Compound 1, can be used to treat a neurological disorder, a disorder associated with excessive neuronal excitability, or a disorder associated with de novo gain-of-function or loss-of-function mutations in major central nervous system sodium channel genes, such as for example, SCN1A, SCN2A and SCN8A. The compounds and compositions described herein, such as Compound 1, can also be used to treat a neurological disorder, a disorder associated with excessive neuronal excitability, or a disorder associated with de novo gain-of-function or loss-of-function mutations in ion channel genes, such as for example, Kcnq2, Kcnc1 and Hcn1.

In some aspects, provided are methods of treating a neurological disorder, a disorder associated with excessive neuronal excitability, or a disorder associated with de novo gain-of-function or loss-of-function mutations in the major central nervous system sodium channel genes, comprising administering to a subject in need thereof an effective amount of a compound of a compound of Formula (I) or a pharmaceutically acceptable salt thereof as defined elsewhere herein, or pharmaceutical compositions comprising the same. In some embodiments, the compound used in the treatment of the disclosed method is a compound of Formula (I-a) or a pharmaceutically acceptable salt thereof as defined elsewhere herein, or pharmaceutical compositions comprising the same. In some embodiments, the compound used in the treatment of the disclosed method is a compound of Formula (I-b) or a pharmaceutically acceptable salt thereof as defined elsewhere herein, or pharmaceutical compositions comprising the same. In some embodiments, the compound used in the treatment of the disclosed method is a compound of Formula (I-c) or a pharmaceutically acceptable salt thereof as defined elsewhere herein, or pharmaceutical compositions comprising the same. In some embodiments, the compound used in the treatment of the disclosed method is a compound of Formula (II) or a pharmaceutically acceptable salt thereof as defined elsewhere herein, or pharmaceutical compositions comprising the same. In some embodiments, the compound used in the treatment of the disclosed method is a compound of Formula (III) or a pharmaceutically acceptable salt thereof as defined elsewhere herein, or pharmaceutical compositions comprising the same. In some embodiments, the compound used in the treatment of the disclosed method is a compound of Formula (IV) or a pharmaceutically acceptable salt thereof as defined elsewhere herein, or pharmaceutical compositions comprising the same. In some embodiments, the compound used in the treatment of the disclosed method is Compound 1 having the following formula:

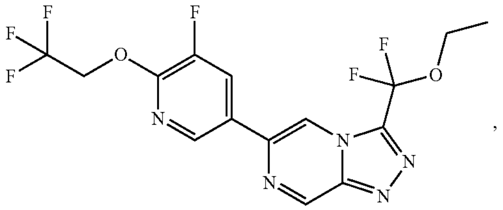 [SMILES: CCOC(F)(F)c1nnc2cnc(-c3cnc(OCC(F)(F)F)c(F)c3)cn12]

, or a pharmaceutically acceptable salt thereof, or pharmaceutical compositions comprising the same.

Exemplary diseases, disorders, or conditions include epilepsy and other encephalopathies (e.g., malignant migrating focal seizures of infancy (MMFSI) or epilepsy of infancy with migrating focal seizures (EIMFS), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy, Lennox-Gastaut syndrome), drug resistant epilepsy, seizures (e.g., frontal lobe seizures, generalized tonic clonic seizures, asymmetric tonic seizures, focal seizures), Tuberous Sclerosis Complex (TSC), leukodystrophy, hypomyelinating leukodystrophy, and leukoencephalopathy), cardiac dysfunctions (e.g., cardiac arrhythmia, Brugada syndrome, myocardial infarction), pulmonary vasculopathy/hemorrhage, pain and related conditions (e.g., neuropathic pain, acute/chronic pain, migraine, etc.), muscle disorders (e.g., myotonia, neuromyotonia, cramp muscle spasms, spasticity), itch and pruritis, movement disorders (e.g., ataxia and cerebellar ataxias), psychiatric disorders (e.g., major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders.

Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure. Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person may be confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

In some embodiments, the epilepsy syndrome is early-onset DEE. In certain embodiments, the epilepsy syndrome is DEE, including, for example, Ohtahara Syndrome; epilepsy with migrating focal seizures of infancy (EIMFS); infantile and childhood DEE, for example West Syndrome and Lennon-Gastaut Syndrome; Dravet Syndrome; Idiopathic/Generic Generalized Epilepsies (IGE/GGE); Temporal Lobe Epilepsy; Myoclonic Astatic Epilepsy (MAE); Migrating Partial Epilepsy of Infancy (MMPSI); and familial hemiplegic migraines, with or without epilepsy. In certain embodiments, the epilepsy syndrome is late seizure onset epileptic encephalopathy.

In some embodiments, the compounds described herein (e.g., a compound of Formula (I), (I-a), (I-b), (I-c), (II), (III), or (IV), or Compound 1) may be used in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome. In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy (SUDEP), Rasmussen encephalitis, malignant migrating partial seizures of infancy, autosomal dominant nocturnal frontal lobe epilepsy, KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, developmental and epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy (SUDEP), Rasmussen encephalitis, malignant migrating partial seizures of infancy, autosomal dominant nocturnal frontal lobe epilepsy, KCNQ2 epileptic encephalopathy, or KCNT1 epileptic encephalopathy) prior to administration of a compound described herein (e.g., a compound of Formula (I), (I-a), (I-b), (I-c), (II), (III), or (IV), or Compound 1).

In one aspect, the disclosure features a method of treating epilepsy or an epilepsy syndrome (e.g., epileptic encephalopathy, epileptic encephalopathy with SCN1A, SCN2A, SCN8A mutations, early infantile epileptic encephalopathy, developmental and epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy (SUDEP), Rasmussen encephalitis, malignant migrating partial seizures of infancy, autosomal dominant nocturnal frontal lobe epilepsy, KCNQ2 epileptic encephalopathy, or KCNT1 epileptic encephalopathy) comprising administering to a subject in need thereof a compound described herein (e.g., a compound of Formula (I), (I-a), (I-b), (I-c), (II), (III), or (IV), or Compound 1) or a pharmaceutically acceptable salt thereof, or a composition comprising the same.

A compound of the present invention (e.g., compound of Formula (I), (I-a), (I-b), (I-c), (II), (III), or (IV), or Compound 1) may also be used to treat an epileptic encephalopathy, wherein the subject has a mutation in one or more of the following genes: ALDH7A1, ALG13, ARHGEF9, ARX, ASAHI, CACNA1G, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRA2, GABRB3, GABRG2, GNAO1, GOSR2, GRIK1, GRIN1, GRIN2A, GRIN2B, HCN1, IER3IP1, KCN1A, KCNA2, KCNB1, KCNC1, KCNMA1, KCNN2, KCNQ2, KCNQ3, KCNT1, KCTD7, LGI1, MEF2C, NHLRC1, PCDH7, PCDH19, PLCB1, PNKP, PNPO, PRICKLE1, PRICKLE2, PRRT2, RELN, SCARB2, SCN1A, SCN1B, SCN2A, SCN8A, SCN9A, SHANK3, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, TRIM3, UNC79 and WWOX.

In some embodiments, the methods described herein further comprise identifying a subject having a mutation in one or more of ALDH7A1, ALG13, ARHGEF9, ARX, ASAHI, CACNA1G, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRA2, GABRB3, GABRG2, GNAO1, GOSR2, GRIK1, GRIN1, GRIN2A, GRIN2B, HCN1, IER3IP1, KCN1A, KCNA2, KCNB1, KCNC1, KCNMA1, KCNN2, KCNQ2, KCNQ3, KCNT1, KCTD7, LGI1, MEF2C, NHLRC1, PCDH7, PCDH19, PLCB1, PNKP, PNPO, PRICKLE1, PRICKLE2, PRRT2, RELN, SCARB2, SCN1A, SCN1B, SCN2A, SCN8A, SCN9A, SHANK3, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, TRIM3, UNC79 and WWOX prior to administration of a compound described herein (e.g., compound of Formula (I), (I-a), (I-b), (I-c), (II), (III), or (IV), or Compound 1).

The compounds described herein (e.g., a compound of Formula (I), (I-a), (I-b), (I-c), (II), (III), or (IV), or Compound 1) may also be used in methods for ameliorating at least one symptom or hallmark of epilepsy or epilepsy syndrome, including, for example, early-onset DEE, in a subject in need thereof. In certain embodiments, the symptom or hallmark includes early-onset seizures and/or global developmental delay. In certain embodiments, the symptom or hallmark includes one or more of seizures, hypotonia, sensory issues, such as sensory integration disorders, motor dysfunctions, intellectual and cognitive dysfunctions, movement and balance dysfunctions, such as choreoathetosis, dystonia, and ataxia, anxiety, sensory issues, urinary retention problems, irritability, behavior issues, visual dysfunctions, delayed language and speech, gastrointestinal disorders (for example, gastroesophageal reflux, diarrhea, constipation, dysmotility, and the like), neurodevelopmental delays, sleep problems, sudden unexpected death in epilepsy (SUDEP), motor development delays, delayed social milestones, repetitive actions, uncoordinated oral movements. In certain embodiments, the seizures include focal, clonic, tonic, and generalized tonic and clonic seizures, prolonged seizures (often lasting longer than 10 minutes), and frequent seizures (for example, convulsive, myoclonic, absence, focal, obtundation status, and tonic seizures).

In one aspect, the disclosure provides a method of ameliorating at least one symptom or hallmark of epilepsy or epilepsy syndrome, including, for example, early-onset DEE, the method comprising administering to a subject in need thereof a compound described herein (e.g., a compound of Formula (I), (I-a), (I-b), (I-c), (II), (III), or (IV), or Compound 1) or a pharmaceutically acceptable salt thereof, or a composition comprising the same. In certain embodiments, the symptom or hallmark includes early-onset seizures and/or global developmental delay. In certain embodiments, the symptom or hallmark includes one or more of seizures, hypotonia, sensory issues, such as sensory integration disorders, motor dysfunctions, intellectual and cognitive dysfunctions, movement and balance dysfunctions, such as choreoathetosis, dystonia, and ataxia, anxiety, sensory issues, urinary retention problems, irritability, behavior issues, visual dysfunctions, delayed language and speech, gastrointestinal disorders (for example, gastroesophageal reflux, diarrhea, constipation, dysmotility, and the like), neurodevelopmental delays, sleep problems, sudden unexpected death in epilepsy (SUDEP), motor development delays, delayed social milestones, repetitive actions, uncoordinated oral movements. In certain embodiments, the seizures include focal, clonic, tonic, and generalized tonic and clonic seizures, prolonged seizures (often lasting longer than 10 minutes), and frequent seizures (for example, convulsive, myoclonic, absence, focal, obtundation status, and tonic seizures).

In some aspects, the present disclosure provides a method of reducing severity, number and/or frequency of seizures in a subject in need thereof that comprises administering to the subject an effective amount of a compound described herein (e.g., a compound of Formula (I), (I-a), (I-b), (I-c), (II), (III), or (IV), or Compound 1), or a pharmaceutically acceptable salt t hereof. In some embodiments, the subject has early-onset DEE. In some embodiments, the compound is Compound 1 or a pharmaceutically acceptable salt thereof.

In some embodiments, the compounds described herein (e.g., a compound of Formula (I), (I-a), (I-b), (I-c), (II), (III), or (IV), or Compound 1) may be used in the treatment of Tuberous Sclerosis Complex (TSC). TSC is a genetic disorder that is typically associated with the growth of noncancerous (benign) tumors throughout different parts of the body. TSC often affects the brain, with some affected individuals having benign growths in the outer surface of the brain (cerebral cortex) known as cortical tubers. Individuals with TSC often develop a pattern of behaviors called TSC-associated neuropsychiatric disorders (TAND) that can be characterized by one or more of the following: hyperactivity, aggression, psychiatric conditions, intellectual disability, and problems with communication and social interaction (autism spectrum disorder). Additionally, individuals with tuberous sclerosis complex may experience attention-deficit/hyperactivity disorder (ADHD) or seizures. Individuals with TSC typically have skin abnormalities, including patches of unusually light-colored skin, areas of raised and thickened skin, and growths under the nails. Tumors on the face called facial angiofibromas are also common and typically begin during childhood.

In one aspect, the disclosure provides a method of treating Tuberous Sclerosis Complex (TSC) comprising administering to a subject in need thereof a compound described herein (e.g., a compound of Formula (I), (I-a), (I-b), (I-c), (II), (III), or (IV), or Compound 1) or a pharmaceutically acceptable salt thereof, or a composition comprising the same.

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula (I), (I-a), (I-b), (I-c), (II), (III), or (IV), or Compound 1).

In one aspect, the disclosure provides a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound described herein (e.g., a compound of Formula (I), (I-a), (I-b), (I-c), (II), (III), or (IV), or Compound 1) or a pharmaceutically acceptable salt thereof, or a composition comprising the same.

In one aspect, provided herein is a method of preferentially inhibiting persistent sodium current ($I_{Na}$) over peak sodium current ($I_{Na}$) in a neuron, said method comprising contacting said neuron with an effective amount of the compound described herein (e.g., a compound of Formula (I), (I-a), (I-b), (I-c), (II), (III), or (IV), or Compound 1). As described in Example 8 herein, an exemplary compound of the present disclosure, i.e., Compound 1, exhibited preference for inhibiting persistent $I_{Na}$ over peak sodium current $I_{Na}$. Specifically, Compound 1 inhibited persistent $I_{Na}$ in $hNa_V1.6$, and exhibited preference for the inhibition of persistent $I_{Na}$ as compared to the inhibition of peak $I_{Na}$, with the ratio of peak $I_{Na}$ to persistent $I_{Na}$ being 60. In contrast, standard-of-care anti-epileptic drugs (AEDs) exhibited less preference for the inhibition of persistent $I_{Na}$ as compared to the inhibition of peak $I_{Na}$, with the ratio of peak $I_{Na}$ to persistent $I_{Na}$ being less than 60. Specifically, the ratio of peak $I_{Na}$ to persistent $I_{Na}$ for various AEDs was 24 (cenobamate), 30 (carbamazepine), 8 (oxcarbazepine) and 16 (lamotrigine). As described herein, preferential inhibition of persistent $I_{Na}$ over peak Iva may be associated with improved tolerability of Compound 1.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

In any of the methods disclosed herein, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject in an effective amount, or a therapeutically effective amount, which is an amount sufficient to provide a therapeutic benefit in the treatment of a disease, disorder or condition, or to delay or minimize one or more symptoms associated with the disease, disorder or condition. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject in an amount ranging from about 0.1 mg/kg to about 1 g/kg, such as from about 0.1 mg/kg to about 10 mg/kg, from about 0.1 mg/kg to about 5 mg/kg, from about 0.1 mg/kg to about 2.5 mg/kg, from about 0.1 mg/kg to about 1.5 mg/kg, from about 0.2 mg/kg to about 15 mg/kg, from about 0.2 mg/kg to about 5 mg/kg, from about 0.25 mg/kg to about 1 mg/kg, from about 0.25 mg/kg to about 0.75 mg/kg, from about 0.25 mg/kg to about 0.5 mg/kg, from about 0.5 mg/kg to about 20 mg/kg, from about 0.5 mg/kg to about 10 mg/kg, or from about 0.5 mg/kg to about 5 mg/kg. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject in an amount ranging from about 10 mg/kg to about 100 mg/kg, such as about 10, 15, 20, 25, 30, 35, 40, 45, 50, 55, 60, 65, 70, 75, 80, 85, 90, 95 or 100 mg/kg. In some embodiments, the compound described herein is administered to a subject at a dose of about 0.5 mg/kg/day. In some embodiments, the compound described herein is administered to a subject at a dose of about 0.6 mg/kg/day. In some embodiments, the compound described herein is administered to a subject at a dose of about 0.7 mg/kg/day. In some embodiments, the compound described herein is administered to a subject at a dose of about 0.8 mg/kg/day. In some embodiments, the compound described herein is administered to a subject at a dose of about 0.9 mg/kg/day. In some embodiments, the compound described herein is administered to a subject at a dose of about 1 mg/kg/day. In some embodiments, the compound described herein (e.g., a compound of Formula (I), (I-a), (I-b), (I-c), (II), (III), or (IV), or Compound 1) or a pharmaceutically acceptable salt thereof is administered to a subject once daily. In some embodiments, the compound described herein (e.g., a compound of Formula (I), (I-a), (I-b), (I-c), (II), (III), or (IV), or Compound 1) or a pharmaceutically acceptable salt thereof is administered to a subject orally.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as a single dose in an amount ranging from about 1 mg to about 180 mg or from about 2.5 mg to about 150 mg, such as about 3 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, or about 150 mg. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as a single dose in an amount of about 0.1 mg to about 500 mg (e.g., from about 0.5 mg to about 200 mg, from about 1 mg to about 150 mg, or from about 10 mg to about 120 mg). In some embodiments, the compound described herein (e.g., a compound of Formula (I), (I-a), (I-b), (I-c), (II), (III), or (IV), or Compound 1) or a pharmaceutically acceptable salt thereof is administered to the subject once daily. In some embodiments, the compound described herein (e.g., a compound of Formula (I), (I-a), (I-b), (I-c), (II), (III), or (IV), or Compound 1) or a pharmaceutically acceptable salt thereof is administered to the subject orally.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as a single dose in an amount of up to 150 mg, such as from about 30 mg to about 120 mg, such as about 30, 35, 40, 45, 50, 55, 60, 65, 70, 75, 80, 85, 90, 95, 100, 105, 110, 115, or 120 mg. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as a single dose in an amount of about 90 mg or about 120 mg. In some embodiments, the compound described herein (e.g., a compound of Formula (I), (I-a), (I-b), (I-c), (II), (III), or (IV), or Compound 1) or a pharmaceutically acceptable salt thereof is administered to the subject once daily.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as multiple doses, with a maximum dose in an amount ranging from about 30 mg to about 150 mg, such as about 30, 35, 40, 45, 50, 55, 60, 65, 70, 75, 80, 85, 90, 95, 100, 105, 110, 115, 120, 125, 130, 135, 140, 145, or 150 mg. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject as multiple doses, with a maximum dose in an amount of about 90 mg or about 120 mg.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject orally. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject every day. In some embodiments, the compound of the disclosure, or a pharmaceutically acceptable salt thereof, is administered to the subject every day for at least 14 days. In some embodiments, the compound of the disclosure, or a pharmaceutically acceptable salt thereof, is administered to the subject in ascending doses, with a starting dose of about 20 mg to about 100 mg, such as about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject in a fasted state, such as more than about 10 hours after the last meal and/or at least about 4 hours before the next meal. In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is administered to the subject in a fed state, such as after a meal normally consumed by the subject, including but is not limited to a high-fat and high calorie meal.

In some embodiments, the compound described herein (e.g., a compound of Formula (I), (I-a), (I-b), (I-c), (II), (III), or (IV), or Compound 1) or a pharmaceutically acceptable salt thereof, or a composition comprising the same, is orally administered to the subject in an amount effective to achieve a maximum plasma concentration ($t_{max}$) between about 1.5 to about 5 hours, such as about 1.5 to about 4 hours, about 2.5 to about 5 hours, about 2.5 to about 4 hours, about 2 to about 4 hours, or about 2 to about 3 hours.

In some embodiments, administration of the compound described herein (e.g., a compound of Formula (I), (I-a), (I-b), (I-c), (II), (III), or (IV), or Compound 1) or a pharmaceutically acceptable salt thereof does not significantly affect the pharmacokinetic parameters of a coadministered agent or therapy contemplated herein. In some embodiments, coadministration with an agent or therapy contemplated herein does not significantly affect the pharmacokinetic parameters of the compound described herein (e.g., a compound of Formula (I), (I-a), (I-b), (I-c), (II), (III), or (IV), or Compound 1). Pharmacokinetic parameters include, for example, the area under the plasma concentration-time curve from time of administration (AUC) to infinity ($AUC_{inf}$), to the time of the last quantifiable concentration ($AUC_{last}$), to 24 hours ($AUC_{0-24}$), maximum observed plasma concentration ($C_{max}$), time of maximum observed plasma concentration ($t_{max}$), and apparent plasma terminal elimination half-life ($t_{1/2}$), among others.

In some embodiments, administration of the compound described herein (e.g., a compound of Formula (I), (I-a), (I-b), (I-c), (II), (III), or (IV), or Compound 1) or a pharmaceutically acceptable salt thereof, or a composition comprising the same, does not result in frequent or severe adverse events. An "adverse event" or "AE" is any untoward medical occurrence in a subject, temporally associated with the use of a treatment (such as, for example, any of the compounds described herein), whether or not considered related to said treatment. An AE can therefore be any unfavorable and unintended sign (including an abnormal laboratory finding), symptom, or disease (new or exacerbated) temporally associated with the use of a treatment, whether or not considered related to the treatment.

Combination Therapy

The compound or composition described herein (e.g., a compound of Formula (I), (I-a), (I-b), (I-c), (II), (III), or (IV), or Compound 1) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome.

In some embodiments, the compound or composition described herein (e.g., a compound of Formula (I), (I-a), (I-b), (I-c), (II), (III), or (IV), or Compound 1) is administered in combination with an anti-epilepsy agent. Anti-epilepsy agents include, but not limited to, brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol. In some embodiments, the compound or composition described herein (e.g., a compound of Formula (I), (I-a), (I-b), (I-c), (II), (III), or (IV), or Compound 1) is administered in combination with carbamazepine.

In some embodiments, the compound or composition described herein (e.g., a compound of Formula (I), (I-a), (I-b), (I-c), (II), (III), or (IV), or Compound 1) is administered in combination with any one of caffeine, dextrametorphan, midazolam, ciprofloxacin, itraconazole, and oxcarbazepine.

In some embodiments, the disclosed methods comprise administering to the subject in need thereof a compound or composition described herein (e.g., a compound of Formula (I), (I-a), (I-b), (I-c), (II), (III), or (IV), or Compound 1) in combination with an anti-epilepsy agent. In some embodiments, the disclosed methods comprise administering to the subject in need thereof a compound or composition described herein (e.g., a compound of Formula (I), (I-a), (I-b), (I-c), (II), (III), or (IV), or Compound 1) in combination with carbamazepine.

Accordingly, one aspect of the disclosure provides for a composition comprising any of the compounds described herein (e.g., a compound of Formula (I), (I-a), (I-b), (I-c), (II), (III), or (IV), or Compound 1) and at least one additional therapeutic agent. In some embodiments, the composition comprises any of the compounds described herein (e.g., a compound of Formula (I), (I-a), (I-b), (I-c), (II), (III), or (IV), or Compound 1) and at least two additional therapeutic agents. In some embodiments, the composition comprises any of the compounds described herein (e.g., a compound of Formula (I), (I-a), (I-b), (I-c), (II), (III), or (IV), or Compound 1) and at least three additional therapeutic agents, any of the compounds described herein (e.g., a compound of Formula (I), (I-a), (I-b), (I-c), (II), (III), or (IV), or Compound 1) and at least four additional therapeutic agents, or any of the compounds described herein (e.g., a compound of Formula (I), (I-a), (I-b), (I-c), (II), (III), or (IV), or Compound 1) and at least five therapeutic agents.

The methods of combination therapy include co-administration of a single formulation containing any of the compounds described herein (e.g., a compound of Formula (I), (I-a), (I-b), (I-c), (II), (III), or (IV), or Compound 1) and additional therapeutic agent or agents, essentially contemporaneous administration of more than one formulation comprising any of the compounds described herein (e.g., a compound of Formula (I), (I-a), (I-b), (I-c), (II), (III), or (IV), or Compound 1) and an additional therapeutic agent or agents, and consecutive administration of any of the compounds described herein (e.g., a compound of Formula (I), (I-a), (I-b), (I-c), (II), (III), or (IV), or Compound 1) and and additional therapeutic agent or agents, in any order, wherein preferably there is a time period where any of the compounds described herein (e.g., a compound of Formula (I), (I-a), (I-b), (I-c), (II), (III), or (IV), or Compound 1) and additional therapeutic agent or agents simultaneously exert a therapeutic effect.

Dosage Forms and Compositions

In one aspect, the disclosure provides dosage forms or compositions useful for treating a disease, disorder, or condition described herein, e.g., a neurological disorder, a disorder associated with excessive neuronal excitability, or a disorder associated with de novo gain-of-function or loss-of-function mutations in major central nervous system sodium channel genes, such as for example, SCN1A, SCN2A, and SCN8A.

Accordingly, the disclosure provides pharmaceutical compositions that contain, as the active ingredient, a compound described herein (e.g., a compound of Formula (I), (I-a), (I-b), (I-c), (II), (III), or (IV), or Compound 1), or a pharmaceutically acceptable salt thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. In some embodiments, the compounds or pharmaceutical compositions of the disclosure are administered orally.

One mode for administration is parenteral, particularly by injection. The forms in which the compositions of the disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the present disclosure. Administration may be via capsule or tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. Sec, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from about 1 mg to about 2 g of a compound described herein, and for parenteral administration, preferably from about 0.1 to about 700 mg of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein is a dosage form or a composition in a dosage form comprising: from about 0.1 mg to about 500 mg (e.g., from about 0.5 mg to about 200 mg, from about 1 mg to about 150 mg, from about 10 mg to about 120 mg) of a compound of Formula (I), (I-a), (I-b), (I-c), (II), (III), or (IV), or Compound 1; and a pharmaceutically acceptable excipient.

In some embodiments, the dosage form or a composition in a dosage form comprises from about 2.5 mg to about 150 mg (e.g., from about 10 mg to about 150 mg, from about 20 mg to about 150 mg, from about 40 mg to about 150 mg, from about 60 mg to about 150 mg, from about 80 mg to about 150 mg, from about 100 mg to about 150 mg, from about 10 mg to about 120 mg, from about 20 mg to about 120 mg, from about 40 mg to about 120 mg, from about 60 mg to about 120 mg, from about 80 mg to about 120 mg, from about 100 mg to about 120 mg, from about 10 mg to about 100 mg, from about 20 mg to about 100 mg, from about 40 mg to about 100 mg, from about 60 mg to about 100 mg, from about 80 mg to about 100 mg, from about 10 mg to about 80 mg, from about 20 mg to about 80 mg, from about 40 mg to about 80 mg, from about 60 mg to about 80 mg, from about 10 mg to about 60 mg, from about 20 mg to about 60 mg, from about 40 mg to about 60 mg, from about 70 mg to about 120 mg, from about 70 mg to about 100 mg, from about 50 mg to about 120 mg, from about 50 mg to 90 mg, from about 30 mg to about 120 mg, from about 30 mg to about 60 mg, from about 30 mg to about 80 mg, from about 30 mg to about 100 mg) of a compound of Formula (I), (I-a), (I-b), (I-c), (II), (III), or (IV), or Compound 1. In some embodiments, the dosage form or a composition in a dosage form is for oral administration.

In some embodiments, the dosage form or a composition in a dosage form comprises from about 1 mg to about 100 mg (e.g., 1 from about 1 mg to about 80 mg, from about 1 mg to about 50 mg, from about 1 mg to about 20 mg, from about 1 mg to about 10 mg, from about 1 mg to about mg, from about 5 mg to about 100 mg, from about 5 mg to about 80 mg, from about 5 mg to about 50 mg, from about 5 mg to about 20 mg) of a compound of Formula (I), (I-a), (I-b), (I-c), (II), (III), or (IV), or Compound 1.

In some embodiments, the dosage form or a composition in a dosage form comprises about 200 mg, 190 mg, 180 mg, 170 mg, 160 mg, 150 mg, 140 mg, 130 mg, 120 mg, 110 mg, 100 mg, about 99 mg, about 98 mg, about 97 mg, about 96 mg, about 95 mg, about 94 mg, about 93 mg, about 92 mg, about 91 mg, about 90 mg, about 85 mg, about 80 mg, about 75 mg, about 70 mg, about 69 mg, about 68 mg, about 67 mg, about 66 mg, about 65 mg, about 64 mg, about 63 mg, about 62 mg, about 61 mg, about 60 mg, about 59 mg, about 58 mg, about 57 mg, about 56 mg, about 55 mg, about 54 mg, about 53 mg, about 52 mg, about 51 mg, about 50 mg, about 45 mg, about 40 mg, about 35 mg, about 30 mg, about 25 mg, about 20 mg, about 15 mg, about 10 mg, about 7 mg, about 5 mg, about 2.5 mg, about 2 mg, about 1.5 mg, or about 1 mg of a compound of Formula (I), (I-a), (I-b), (I-c), (II), (III), or (IV), or Compound 1.

In another aspect, the present disclosure provides a dosage form or a composition in a dosage form comprising: a plurality of particles of a compound of Formula (I), (I-a), (I-b), (I-c), (II), (III), or (IV), or Compound 1; and a pharmaceutically acceptable excipient, wherein the amount of the plurality of particles of a compound of Formula (I), (I-a), (I-b), (I-c), (II), (III), or (IV), or Compound 1 in the dosage form is from about 0.1 mg to about 500 mg (e.g., from about 0.5 mg to about 200 mg, from about 1 mg to about 150 mg, from about 10 mg to about 120 mg).

In some embodiments, the plurality of particles of a compound of Formula (I), (I-a), (I-b), (I-c), (II), (III), or (IV), or Compound 1 in the dosage form or composition is from about 2.5 mg to about 150 mg (e.g., from about 10 mg to about 150 mg, from about 20 mg to about 150 mg, from about 70 mg to about 120 mg, from about 30 mg to about 60 mg, about 100 mg, about 50 mg).

In some embodiments, the dosage form or the composition is configured for oral administration. In some embodiments, the dosage form is a solid form. In some embodiments, the dosage form is in the form of a capsule. In some embodiments, the pharmaceutical excipient in the capsule is a filler (e.g., cellulose derivatives (e.g., microcrystalline cellulose), starches (e.g., hydrolyzed starches, and partially pregelatinized starches), anhydrous lactose, lactose monohydrate, sugar alcohols (e.g., sorbitol, xylitol, and mannitol).

In some embodiments, the dosage form is a liquid form. In some embodiments, the dosage form is in the form of a solution. In some embodiments, the pharmaceutical excipient in the solution is selected from the group consisting of a filler (e.g., polymer (e.g., PEG 400)), an emulsifier (e.g., a castor oil derivative (e.g., Kolliphor RH40), a surfactant (e.g., a glyceride (e.g., Labrafil M2125 CS), a vitamin derivative (e.g., Vitamin ETPGS)), a solvent (e.g., propylene glycol, ethanol, diethylene glycol monoethyl ether (or Transcutol HP)).

In some embodiments, the concentration of a compound of Formula (I), (I-a), (I-b), (I-c), (II), (III), or (IV), or Compound 1 in the solution is from about 0.1 mg/mL to about 10 mg/mL (e.g., from about 0.5 mg/mL to about 10 mg/mL, from about 1 mg/mL to about 10 mg/mL, from about 2 mg/mL to about 10 mg/mL, from about 3 mg/mL to about 10 mg/mL, from about 4 mg/mL to about 10 mg/mL, from about 5 mg/mL to about 10 mg/mL, from about 6 mg/mL to about 10 mg/mL, from about 0.1 mg/mL to about 8 mg/mL, from about 0.5 mg/mL to about 8 mg/mL, from about 1 mg/mL to about 8 mg/mL, from about 2 mg/mL to about 8 mg/mL, from about 3 mg/mL to about 8 mg/mL, from about 4 mg/mL to about 8 mg/mL, from about 5 mg/mL to about 8 mg/mL, from about 6 mg/mL to about 8 mg/mL, from about 0.5 mg/mL to about 6 mg/mL, from about 1 mg/mL to about 6 mg/mL, from about 2 mg/mL to about 6 mg/mL, from about 3 mg/mL to about 6 mg/mL, from about 4 mg/mL to about 6 mg/mL, from about 0.5 mg/mL to about 4 mg/mL, from about 1 mg/mL to about 4 mg/mL, or from about 2 mg/mL to about 4 mg/mL).

In some embodiments, the concentration of a compound of Formula (I), (I-a), (I-b), (I-c), (II), (III), or (IV), or Compound 1 in the solution is about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

In some embodiments, the dosage form is in the form of a suspension. In some embodiments, the concentration of a compound of Formula (I), (I-a), (I-b), (I-c), (II), (III), or (IV), or Compound 1 in the suspension is about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 20 mg/mL, about 25 mg/mL.

In some embodiments, the concentration of a compound of Formula (I), (I-a), (I-b), (I-c), (II), (III), or (IV), or Compound 1 in the suspension is from about 0.1 mg/mL to about 10 mg/mL (e.g., from about 0.5 mg/mL to about 10 mg/mL, from about 1 mg/mL to about 10 mg/mL, from about 2 mg/mL to about 10 mg/mL, from about 3 mg/mL to about 10 mg/mL, from about 4 mg/mL to about 10 mg/mL, from about 5 mg/mL to about 10 mg/mL, from about 6 mg/mL to about 10 mg/mL, from about 0.1 mg/mL to about 8 mg/mL, from about 0.5 mg/mL to about 8 mg/mL, from about 1 mg/mL to about 8 mg/mL, from about 2 mg/mL to about 8 mg/mL, from about 3 mg/mL to about 8 mg/mL, from about 4 mg/mL to about 8 mg/mL, from about 5 mg/mL to about 8 mg/mL, from about 6 mg/mL to about 8 mg/mL, from about 0.5 mg/mL to about 6 mg/mL, from about 1 mg/mL to about 6 mg/mL, from about 2 mg/mL to about 6 mg/mL, from about 3 mg/mL to about 6 mg/mL, from about 4 mg/mL to about 6 mg/mL, from about 0.5 mg/mL to about 4 mg/mL, from about 1 mg/mL to about 4 mg/mL, or from about 2 mg/mL to about 4 mg/mL).

EXAMPLES

In order that the embodiments described herein may be more fully understood, the following examples are set forth. The examples described in this application are offered to illustrate the compounds, pharmaceutical compositions, and methods provided herein and are not to be construed in any way as limiting their scope.

Example 1. Effect of Compound 1 on Mouse Wildtype CA1 Pyramidal Neuron Excitability Using Brain Slice Whole-Cell Patch-Clamp Electrophysiology The aim of this study was to determine the effect of Compound 1 on intrinsic excitability of CA1 pyramidal neurons from brain slices obtained from wildtype mice.

1. Materials and Methods i. Brain Slice Preparation

Mice (p17-p21) were anesthetized with 2% isoflurane, and the brain was removed and placed into an iced slurry of incubation solution containing: 125 mM Choline chloride, 2.5 mM KCl, 1.25 mM $NaH_2PO_4$, 26 mM $NaHCO_3$, 20 mM D-glucose, 0.4 mM $CaCl_2 \cdot 2H_2O$, and 6 mM $MgCl_2 \cdot 6H_2O$ at a pH of 7.4, maintained by continuous bubbling with carbogen gas (95% $O_2$-5% $CO_2$). Three hundred micrometer coronal hippocampal slices were cut on a vibratome (VT1200; Leica) for whole-cell patch-clamp experiments. Slices were incubated for a minimum of 1 hour in the incubation solution at room temperature before patching.

ii. Current Clamp Electrophysiology Recordings

Brain slices were transferred to a submerged recording chamber on an upright microscope (Slicescope Pro 1000; Scientifica) and were perfused (2 ml/min) with the extracellular artificial cerebral spinal fluid (aCSF) recording solution at 32° C. The extracellular aCSF recording solution contained: 125 mM NaCl, 2.5 mM KCl, 1.25 mM $NaH_2PO_4$, 26 mM $NaHCO_3$, 10 mM D-glucose, 2 mM $CaCl_2 \cdot 2H_2O$, and 2 mM $MgCl_2 \cdot 6H_2O$ at a pH of 7.4 maintained by continuous bubbling with carbogen gas (95% $O_2$-5% $CO_2$).

CA1 pyramidal neurons were identified visually in the stratum pyramidale of the CA1 region of the hippocampus, using infrared-oblique illumination microscopy with a 40× water-immersion objective (Olympus) using a camera (Dage IR-2000; Dage). Cell identity was also confirmed using action potential firing characteristics, where action potentials were accommodating at high current injections and had a wide action potential half-width. Patch-clamp recordings were made using a micromanipulator (MPC-200; Sutter) and Axon Multiclamp 700B patch-clamp amplifier (MDS). Data were acquired using pClamp software (v10; MDS) using a sampling rate of 50 kHz and low pass Bessel filtered at 10 kHz (Digidata 1550b; Axon). Patch pipettes (3-7 MΩ; GC150F-7.5; Harvard Instruments) pulled using a Flaming/brown micropipette puller (Model P-1000; Sutter) were filled with intracellular recording solution containing: 125 mM K gluconate, 5 mM KCl, 2 mM $MgCl_2 \cdot 6H_2O$, 10 mM HEPES, 4 mM ATP-Mg, 0.3 mM GTP-Na, 10 mM Phosphocreatine, 0.1 mM EGTA, and 0.2% Biocytin at a pH of 7.2 (adjusted with KOH) and a measured osmolarity of 292 mOsm.

iii. Intrinsic Excitability Assay (Evoked Action Potentials)

Figure 1B:
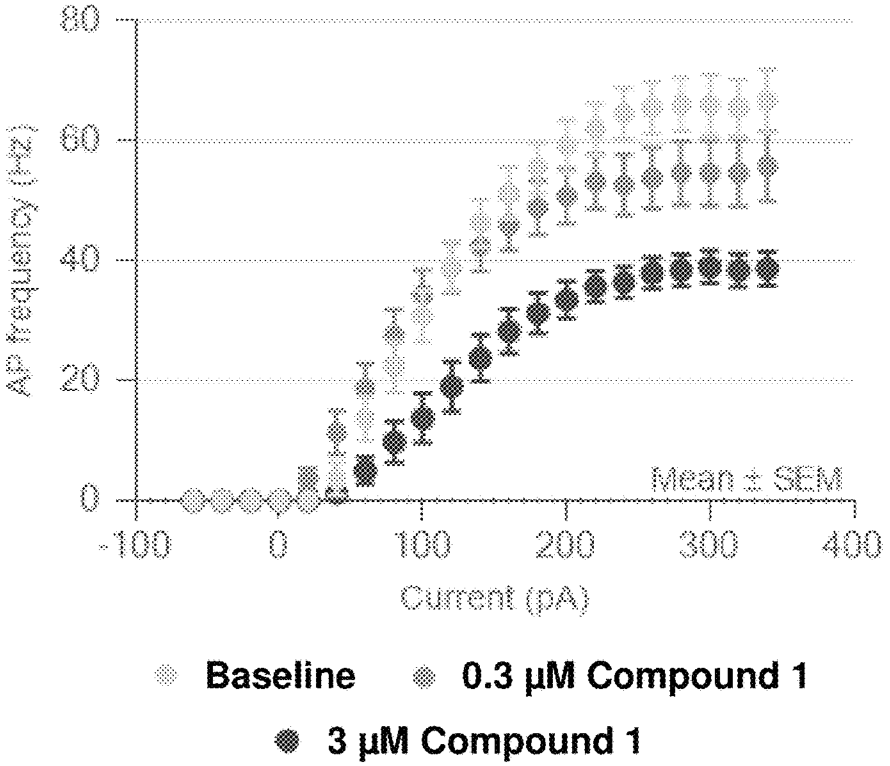

Studies were performed using whole-cell current clamp recording mode. The experimental timeline is depicted in FIG. 1A. Once the whole-cell configuration was obtained for 2 minutes, a holding current was injected to maintain a membrane potential of approximately −70 mV. Current steps (injected current of between −60 to 340 pA in 20 pA steps, 400 ms duration) (FIG. 1B)) were applied in current clamp mode. The amplitude of current injections was relative to the holding current. A test pulse (−5 pA amplitude, 50 ms duration) was applied 650 ms after the termination of the main current step. The inter sweep interval was 5 seconds (0.2 Hz). To be included in the study, a cell had to have an access resistance of less than 20 M2 and a holding current of less than −200 pA. Once baseline action potential firing was determined in the presence of the extracellular aCSF recording solution (baseline), Compound 1 (300 nM or 3 μM) was washed onto the slice for 5 minutes before repeating the action potential generating protocol (FIG. 1B).

iv. Data Analysis for Generation of Input-Frequency Relationships

Data were analyzed using Axograph X software. Individual action potentials were identified and counted using a +50 mV amplitude threshold relative to pre-event baseline. The frequencies of action potentials generated were plotted for each of the current injections to create an input-frequency relationship for each cell. The average frequency of action potentials evoked for each current injection was calculated and reported in Tables 1 and 4. Action potential amplitudes were determined relative to the pre-event baseline at the +200 pA current injection step for each cell. The average action potential amplitude for each evoked action potential was calculated and reported in Tables 3 and 6. Once an action potential count had less than three cells contributing to the averaged amplitude, it was excluded from analysis. For statistical comparisons between groups, the total number of action potentials fired per cell was calculated. The averaged values are reported in Tables 2 and 5. Statistical analysis was performed using GraphPad Prism software (v8). Paired two-tailed Student's t-tests were used to test the effect of compound on action potential firing compared to baseline. In all cases, the significance for analysis was set as an alpha value of 0.05.

2. Results

In slices from wildtype mice, Compound 1 at both 0.3 and 3 μM significantly reduced the number of action potentials generated when compared to baseline (FIG. 1A-1B). The reduction in CA1 pyramidal neuron intrinsic excitability by Compound 1 as measured using evoked action potential firing was concentration-dependent (FIG. 1B).

Example 2. Effect of Compound 1 on Human $Na_V1.6$ Channels Using the PatchXpress® (Molecular Devices) Electrophysiology Platform The aim of this study was to determine the effect of Compound 1 on the human $Na_V1.6$ late (persistent) current and peak current tonic block (TB), and peak current use-dependent block (UDB).

1. Materials and Methods i. Cell Preparation

HEK-293 cell lines stably expressing either human $Na_V1.6$ (NP_055006), mouse $Na_V1.6$ (NP_035453.2), or rat $Na_V1.6$ (NP_062139) were used. All cells were seeded at $2\times10^6$ cells per Nunc T75 flask for 2 days in culture. At time of harvest for assays, the cell counts were approximately $6\times10^6$ cells. Cells were washed (1×) in DPBS (Hyclone, Cat #SH30028.03) for approximately 30 seconds. 1 mL of 1×0.05% Trypsin-EDTA (GIBCO Cat #25300-054) was added and swirled around to cover the bottom of the flask and was allowed to sit on the cells for approximately 4 minutes (±90% of the cells were lifted by light tapping of the flask). 10 mL of warmed media (DMEM high glucose media Hyclone, SH30022.02 supplemented with 10% Fetal Bovine Serum, 2 mM Sodium Pyruvate, 10 mM HEPES and 400 μg/mL G418) was added to inactivate the trypsin. Cells were triturated until a single cell suspension was achieved. A cell count was performed and cells were aliquoted into a 250 ml centrifuge tube at a concentration of $2\times10^5$/mL in +30 ml of prewarmed media. The 250 mL centrifuge tube was placed on a rocker in an incubator set at 28° C. and gently rocked for approximately 1 hour to allow cells to recover. Cell aliquots of 5 mL ($1\times10^6$ cells) were placed in a 15 mL centrifuge tube and spun at 100×g for 2 minutes. Supernatant was removed leaving a cell pellet. 100 μL of external recording solution was added to the pellet and triturated 20 times to achieve a single cell suspension and then transferred to a 1.5 mL tube for placement in the PatchXpress® (Molecular Devices).

ii. Test Agent Preparation

Compound 1 was provided as powder and prepared as 10 mM DMSO stocks in 1 dram glass vials prior to assay. Immediately prior to assay, Compound 1 was diluted with DMSO to 300×, the designated final assay concentration. Assay dilutions (1× concentration) were prepared by pipetting 3 μL of diluted Compound 1 into 897 μL of extracellular solution in a 1 mL glass shell vial. Vials were capped and vortexed until initiation of the PatchXpress® (Molecular Devices) recording protocol.

iii. PatchXpress® (Molecular Devices) Recording Solutions

The same intracellular recording solution was used for the persistent and peak $I_{Na}$ assays, which contained: 135 mM CsF, 10 mM CsCl, 5 mM NaCl, 10 mM HEPES, 5 mM EGTA at a pH of 7.4 (adjusted with CsOH) and a measured osmolarity of 298 mOsm (adjusted with mannitol). For the persistent $I_{Na}$ assay, the external recording solution contained: 135 mM NaCl, 5.4 mM KCl, 5 mM glucose, 2 mM $CaCl_2$), 1 mM $MgCl_2$, 10 mM HEPES, and 200 nM ATX-II (sea anemone toxin, Alomone Labs; Jerusalem, Israel) at a pH of 7.4 (adjusted with NaOH) and a measured osmolarity of 300 mOsm (adjusted with mannitol). For the peak $I_{Na}$ assays, the external recording solution contained: 100 mM NaCl, 35 mM NMDG, 5.4 mM KCl, 5 mM glucose, 2 mM $CaCl_2$), 1 mM $MgCl_2$, and 10 mM HEPES at a pH of 7.4 (adjusted with NaOH) and a measured osmolarity of 300 mOsm (adjusted with mannitol).

iv. Experimental Protocols

All studies were performed using the PatchXpress® (Molecular Devices) automated patch clamp platform (Molecular Devices) using the whole cell configuration. Recordings were performed at room temperature. Data were collected using Patch Commander software (Molecular Devices) and processed using DataXpress 2.0 (Molecular Devices). Cell acceptance criteria were continuously monitored by custom scripts during the recording. Acceptance criteria for all assays were: baseline peak $I_{Na}$>800 pA, $R_{seal}$>200 MΩ, and, where appropriate, persistent $I_{Na}$>100 pA. Compensation was 50% and leak subtraction was not used. Currents were filtered at 5 kHz and digitized at 32.5 kHz. $R_{access}$ and $R_{seal}$ were monitored throughout the recording and cells with $R_{access}$>10 MΩ or $R_{seal}$<200 MΩ were terminated automatically by script.

Late (persistent) current Block: The inhibition of ATX-II activated late current was measured using a 200 ms voltage step to 0 mV. Protocols used low stimulation rates (about 0.1 Hz) and negative potentials (−120 mV) to keep channels in closed (resting) states. Pharmacology was measured as the mean $I_{Na}$ during the final 20 ms of the step to 0 mV and leak subtraction was not used.

Tonic Block (TB): Tonic Block (TB) protocols used low stimulation rates (about 0.1 Hz) and negative potentials (−120 mV) to keep channels in closed (resting) states. Pharmacology was measured during peak $I_{Na}$ in response to step to 0 mV. No leak subtraction was used.

Use Dependent Block (UDB-10 Hz): UDB protocols used elevated stimulation rates (10 Hz) to cycle channels between closed (resting), open, and fast inactivated states. Slow inactivation was minimized by using a negative potential (−120 mV) between the steps. Pharmacology was measured during peak $I_{Na}$ in response to step to 0 mV. No leak subtraction was used.

Voltage Dependent Block (VDB): VDB protocols used a depolarized voltage to keep channels in half-inactivated (resting) states. This allowed equilibrium binding and accurate determination of isoform selectivity (in the absence of biological features). For each cell, the midpoint of inactivation ($V_{0.5}$) was determined using a 5,000 ms step to increase voltages (10 mV increments) to inactivate the channel immediately followed by a 2 ms step to 0 mV to maximally activate the channels. The holding potential (Vhold) was −120 mV between steps. The peak $I_{Na}$ measured in response to the step to 0 mV was plotted and fitted with a Boltzmann equation to determine the $V_{0.5}$. This value was then used for the VDB protocol. Pharmacology was measured during peak $I_{Na}$ in response to step to 0 mV. No leak subtraction was used.

Plotting and fitting were performed using GraphPad Prism (GraphPad Software). Percent inhibition was calculated, expressed as mean±SEM, and plotted versus the tested concentration. Data were fit using a Hill equation [Max_Effect/(1+($IC_{50}$/x)^Hill_Slope] to estimate the concentration of compound producing half inhibition ($IC_{50}$) and hill slope. MaxEffect was allowed to vary for the Use Dependent Block (UDB) assay but was fixed at 100 for all other assays.

2. Results

Figure 2A:
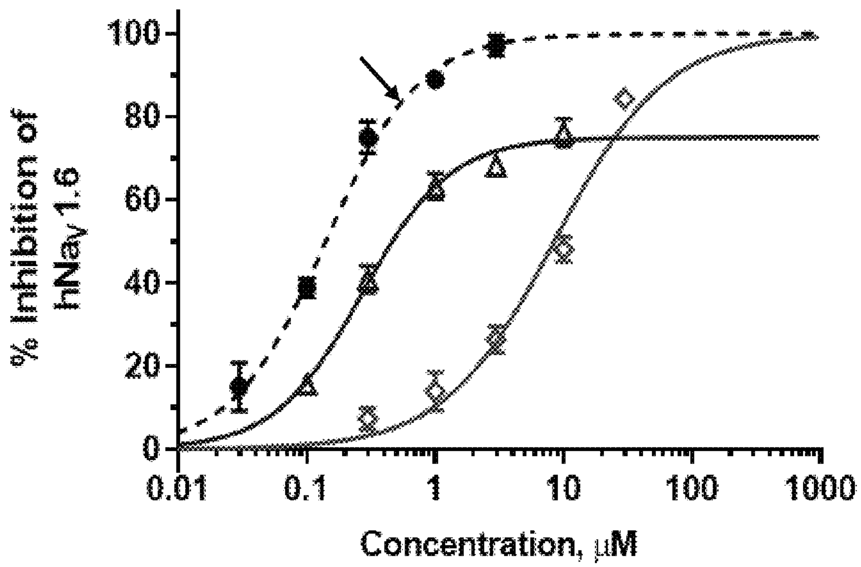
FIG. 2A-2C depict the effect of Compound 1 (FIG. 2A), lamotrigine (LTG) (FIG. 2B), and carbamazepine (CBZ) (FIG. 2C) on human $Na_V$1.6 channel using the PatchXpress® Molecular Devices) Electrophysiology platform.
Figure 2B:
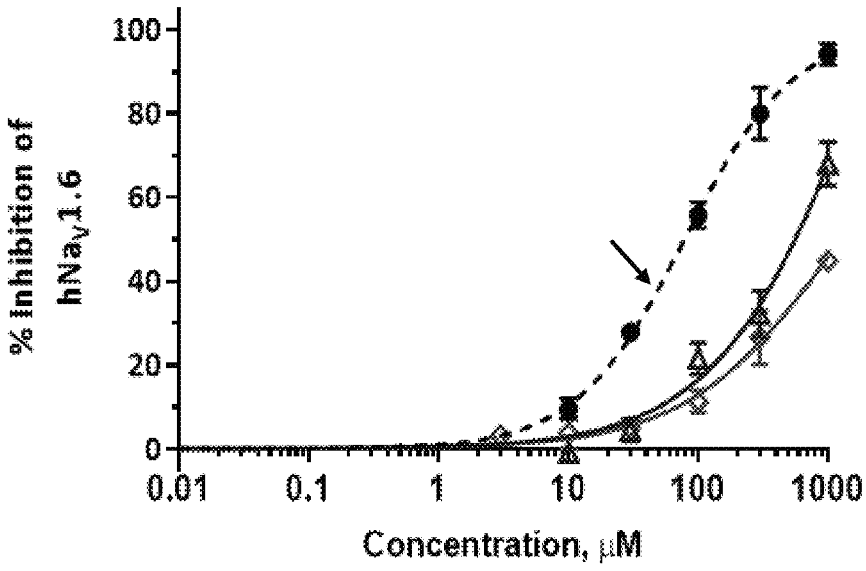
Figure 2C:
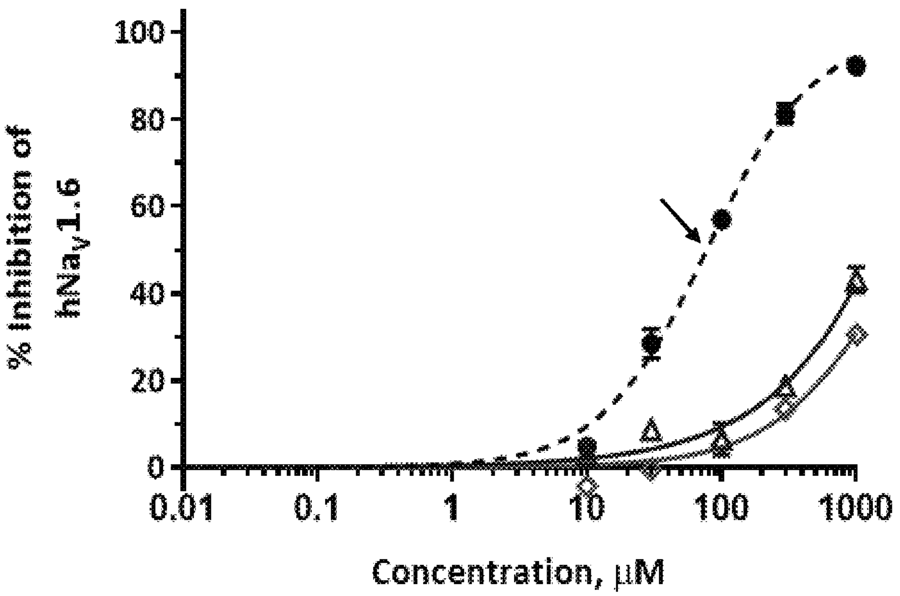

Compound 1 produced concentration dependent inhibition of $hNa_V1.6$ at a 10 Hz stimulus frequency (UDB). The blocking of $hNa_V1.6$ channels by Compound 1 from the resting state (TB) was also concentration dependent, however the extent of block was less than that observed for either state-dependent or use-dependent assays (FIG. 2A). Compound 1 demonstrates a preference for persistent $I_{Na}$ relative to peak $I_{Na}$ for all assay conditions (arrow in FIG. 2A). By contrast, the two standard $Na_V$-targeting antiepileptic drugs lamotrigine (LTG) and carbamazepine (CBZ) exhibited lower potency and no preference for persistent $I_{Na}$ (arrows in FIG. 2B (LTG) and FIG. 2C (CBZ)).

Example 3. Effect of Compound 1 on Maximal Electroshock Induced Seizure in Mouse Model The maximal electroshock (MES) test is a validated model for evaluating anti-seizure potential of compounds. Valproic acid (VPA) is used clinically for its anticonvulsant properties and is an effective treatment for tonic seizures. The object of these studies was to evaluate the effect of Compound 1 (0.3, 1, 3 and 10 mg/kg p.o. (oral)) to attenuate MES-induced seizures in male CD-1 mice.

1. Materials and Methods i. Animals

Male CD-1 mice, 6-weeks old, were obtained from Vital River (Beijing, China). The average body weight was approximately 35 g at the time the experiments were carried out. The mice were housed in groups of 3-5 under controlled conditions (temperature: 20-26° C.; humidity: 40-70%; air exchange rate: 10-15 cycles/hour; 12:12 light-dark cycle with lights on at 5:00 a.m.). Food and water were available ad libitum. The mice were acclimated to these conditions for 6 days before the start of behavioral testing.

ii. Drug Formulation

Dosing solutions were prepared on each experiment day. A stock solution of the highest dose of Compound 1 was prepared in 35% HPBCD (Vehicle 2) and diluted to make the lower doses. VPA was prepared in saline (Vehicle 1). All solutions were protected from light. All compounds and vehicles were dosed at 10 ml/kg.

iii. Study Protocol

The MES test was carried out over two days with 6 of 12 mice from each treatment group being tested on each day. Mice were brought to the test room at least one hour before the start of the experiment. All animals were marked on the tail with a permanent marker and weighed. Mice were randomly assigned into one of the six treatment groups.

Compound 1 or 35% HPBCD (Vehicle 2) were orally (p.o.) administered to animals 30 minutes prior to the MES test or VPA or saline (Vehicle 1) were intraperitoneally (i.p.) administered 30 minutes prior to the MES test. Just before the start of the MES test, possible side effects, such as overt sedation were recorded.

A Grass S88x (Grass Technologies of Astro-Med, Inc., West Warwick, RI) Stimulus Isolation Unit (A385, WPI Inc., USA) was set to deliver a 50 mA square-wave stimulus, with a 0.8 second duration, a pulse width of 10 msec, and a frequency of 50 Hz. A pair of custom stainless steel electrodes were soaked in 0.2% Agar, and then the subject received bilateral transauricular stimulation through ear-clip electrodes. During the stimulation, mice were manually restrained. They were then released into the observation cage for convulsion observation for 60 seconds immediately after stimulation. Each mouse was observed continuously by individuals blinded to treatment conditions and results were recorded.

Sedation assessment endpoints were: (1) None: mouse exhibits normal locomotor behavior; (2) Mild: mouse shows less locomotion or immobility when alone in its home cage, but shows normal locomotor activity if provoked by touching from an observer's hand; (3) Moderate: mouse shows immobility when alone in its home cage and reduced locomotor activity when pushed or provoked by touching from an observer's hand; and (4) Severe: mouse completely loses the ability to move.

Anti-seizure assessment endpoints were: (1) latency of hindlimb tonic flexion; (2) latency of hindlimb tonic extension; (3) total #hindlimb tonic flexions; (4) total #hindlimb tonic extensions; (5) latency to death; and (6) mortality rate Following the experiment, mice were anesthetized with $CO_2$ and terminal plasma and brain tissue samples were collected. 500 μL whole blood was collected via cardiac puncture and placed in tubes with 10 μL EDTAK2. The tubes were then placed in wet ice until centrifuged at 2,000 g for 5 minutes at 4° C. The supernatant plasma was pipetted into Eppendorf tubes. Both brain and plasma samples were stored at −80° C. until determination of Compound 1 concentration in each sample.

iv. Plasma Sample Preparation

An aliquot of 20 μL unknown sample, calibration standard, quality control, dilute quality control, single blank, and double blank sample was added to a 1.5 mL tube. Each sample (except the double blank) was quenched with 300 μL IS solution respectively (double blank sample was quenched with 300 μL ACN), and then the mixture was vortex-mixed well (at least 15 seconds) and centrifuged for 15 minutes at 12000 g, 4° C. 70 μL supernatant was transferred to a 96-well plate and centrifuged for 5 minutes at 3220 g, 4° C. Then 5 μL supernatant was injected for LC-MS/MS analysis.

v. Brain Sample Preparation

Brain homogenate was prepared by homogenizing brain tissue with 5 volumes (w:v) of homogenizing solution (cold 15 mM PBS/MeOH (V:V, 2:1)). An aliquot of 20 μL unknown sample, calibration standard, quality control, dilute quality control, single blank and double blank sample was added to a 1.5 mL tube. Each sample (except the double blank) was quenched with 300 μL IS solution respectively (double blank sample was quenched with 300 μL ACN), and then the mixture was vortex-mixed well (at least 15 seconds) and centrifuged for 15 minutes at 12000 g, 4° C. 70 μL supernatant was transferred to the 96-well plate and centrifuged for 5 minutes at 3220 g, 4° C. Then 5 μL supernatant was injected for LC-MS/MS analysis.

vi. Statistical Analysis

All statistical analyses were conducted using GraphPad Prism 7.0. Data are presented as mean±s.e.m. and $p<0.05$ was regarded as statistically significant. Mann-Whitney test was used to detect significant differences in latency and number of seizures between saline and VPA groups. Kruskal-Wallis followed by Dunn's test was used to detect significant differences in latency and number of seizures between 35% HPBCD and Compound 1.

vii. Calculating $ED_{50}$ and $EC_{50}$ Values

Dose-response and concentration-response curves for plasma and brain were fitted for each end-point using GraphPad Prism. From these fitted curves, $ED_{50}$ and $EC_{50}$ values were calculated.

2. Results

Figure 3:
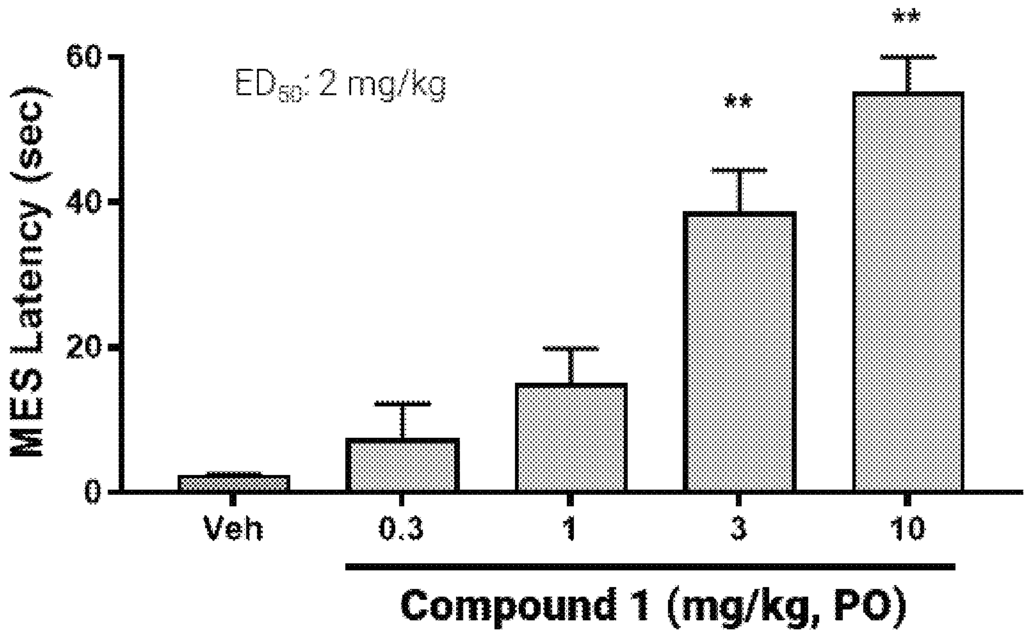
FIG. 3 depicts the effect of Compound 1 on maximal electroshock induced seizure (MES) in male CD-1 mice. CD-1 mice: n=12/group; **p<0.01 vs. Veh.

As shown in FIG. 3, at 3 mg/kg (p.o.), Compound 1 significantly increased latency to seizures following bilateral transauricular stimulation. The ability of Compound 1 to increase latency to seizures following MES was even more pronounced at 10 mg/kg (p.o.). Compound 1 has a calculated $ED_{50}$ of 2 mg/kg. These data suggest that Compound 1 has anti-seizure properties in the MES-induced seizure model.

Example 4. Effect of Compound 1 on Spontaneous Locomotor Activity (sLMA) in Mouse Model The Spontaneous Locomotor Activity (sLMA) test is a validated model for evaluating the potential motor side effects of compounds. The objective of this study was to evaluate the effect of Compound 1 (10, 20 and 40 mg/kg, p.o.) on spontaneous locomotor activity (sLMA) in male CD-1 mice at 30 minutes post-dose.

1. Materials and Methods i. Animals

Male CD-1 mice, 6-weeks old, were obtained from Vital River (Beijing, China). The average body weight was 25-35 g at the time the experiments were carried out. The mice were housed in groups of 3-5 under controlled conditions (temperature: 20-26° C.; humidity: 40-70%; air exchange rate: 10-15 cycles/hour; 12:12 light-dark cycle with lights on at 5:00 a.m.). Food and water were available ad libitum. The mice were acclimated to these conditions for 6 days before the start of the studies.

ii. Drug Formulation

Dosing solutions were prepared on each experiment day. A stock solution of the highest dose of Compound 1 was prepared in 35% HPBCD (vehicle) and diluted to make the lower doses. The stock was stirred and sonicated for at least 20 minutes and resulted in a homogeneous suspension. All solutions were protected from light. Samples from dosing solutions were stored at 4° C. Both compound and vehicle were dosed at 10 ml/kg.

iii. Study Protocol

The sLMA test was carried out over two days. 5 of 10 mice from each treatment group were tested on each day. All animals were marked on the tail with a permanent marker and weighed. Mice were randomly assigned into one of the four treatment groups. Animals were acclimated to the test room at least 30 minutes before the start of the experiment.

Compound 1 or 35% HPBCD (vehicle) were orally (p.o.) administered to animals 30 minutes prior to the sLMA test. Possible side effects, such as overt sedation, were recorded just before the start of the sLMA test.

Sedation assessment endpoints were: (1) None: mouse exhibits normal locomotor behavior; (2) Mild: mouse shows less locomotion or immobility when alone in its home cage, but shows normal locomotor activity if touched by an observer; (3) Moderate: mouse shows immobility when alone in its home cage and reduced locomotor activity when pushed or touched by an observer; and (4) Severe: mouse completely loses the ability to move.

30 minutes after being dosed with Compound 1 or vehicle, the mouse was placed at the center of the test chamber (40×40×30 cm, 45±5 Lux on the floor) for the 30-minute sLMA video recording. Each mouse was automatically tracked with overhead cameras using a 1-minute sampling window in an isolated chamber. Spontaneous locomotor activity was then analyzed offline using the Animal Behavior Video Tracking Analysis System (Ji Liang Software Technology Co., Ltd., Shanghai, China).

Locomotor status was defined as >2 mm of movement in every 200 ms (Frame-rate recorded was 20 frames/second. Locomotor status was identified in every 4 frame-to-frame interval. The accumulated shift of tracking spots that exceeded 2 mm in every 4 frame intervals was identified as a locomotor epoch). Traveling distance was calculated automatically from all the locomotion epochs and analyzed. Following the test, a short video recording (10 seconds) was taken of 2-3 representative mice showing side effects from each of the Compound 1 treatment groups.

All mice were anesthetized with $CO_2$. Then, terminal plasma and brain tissue samples were collected from animals in the drug treatment groups. 500 μL whole blood was collected via cardiac puncture and placed in tubes with 10 μL EDTAK2. The tubes were then placed in wet ice until centrifuged at 2000 g for 5 minutes at 4° C. The supernatant plasma was pipetted into Eppendorf tubes. Both brain and plasma samples were stored at −80° C. until drug concentration analysis of Compound 1 levels.

iv. Plasma Sample Preparation

An aliquot of 20 μL unknown sample, calibration standard, quality control, dilute quality control, single blank, and double blank sample was added to a 1.5 mL tube. Each sample (except the double blank) was quenched with 300 μL IS solution (double blank sample was quenched with 300 μL ACN), and then the mixture was vortex-mixed well for at least 15 seconds and centrifuged for 15 minutes at 12000 g, 4° C. 65 μL supernatant was transferred to a 96-well plate and centrifuged for 5 minutes at 3220 g, 4° C. Then 3 μL supernatant was directly injected for LC-MS/MS analysis.

v. Brain Sample Preparation

Brain homogenate was prepared by homogenizing brain tissue with 5 volumes (w: v) of cold 15 mM PBS/MeOH (V:V, 2:1). An aliquot of 40 μL unknown sample, calibration standard, quality control, dilute quality control, single blank and double blank sample was added to a 1.5 mL tube. Each sample (except the double blank) was quenched with 600 μL IS solution (double blank sample was quenched with 600 μL ACN), and then the mixture was vortex-mixed well for at least 15 seconds and centrifuged for 15 minutes at 12000 g, 4° C. 65 μL supernatant was transferred to a 96-well plate and centrifuged for 5 minutes at 3220 g, 4° C. Then 3 μL of the supernatant was directly injected for LC-MS/MS analysis.

vi. Statistical Analysis

All statistical analyses were conducted using GraphPad Prism 7.0. Data are presented as mean±s.e.m., and $p<0.05$ was regarded as statistically significant. Two-way ANOVA with Dunnett's post hoc test was used to detect significant differences in traveling distance per 5-minute bins between vehicle and Compound 1 treatment groups. ANOVA followed by Dunnett's test was used to detect significant differences in total traveling distance over 30 minutes between vehicle and Compound 1 treatment groups.

vii. Calculating $TD_{50}$ and $TC_{50}$ Values

Dose-response and concentration-response curves for plasma and brain were fitted for each end-point using GraphPad Prism. From these fitted curves, $TD_{50}$ and $TC_{50}$ values were calculated.

2. Results

Figure 4:
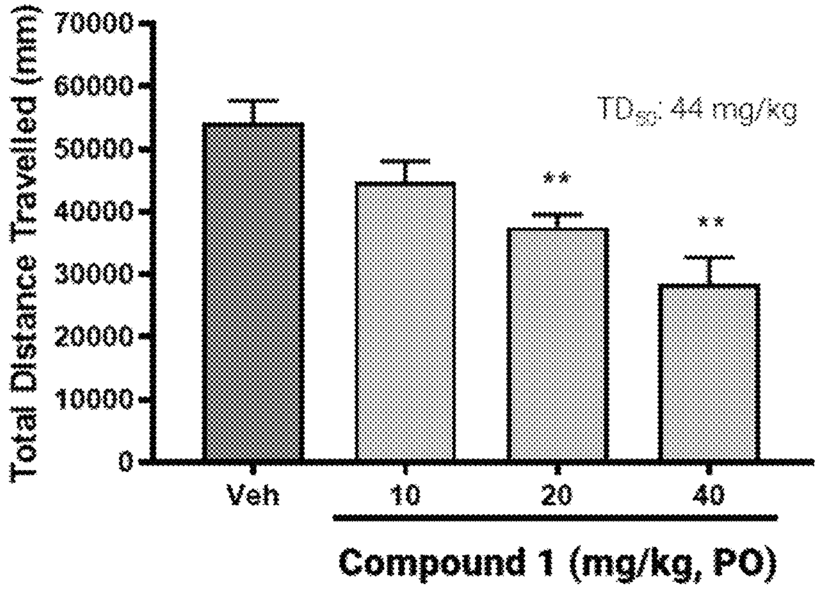
FIG. 4 depicts the effect of Compound 1 on spontaneous locomotor activity (sLMA) in male CD-1 mice. CD-1 mice: n=20/group; ANOVA/Dunnett; **p<0.01 vs. Veh.

As shown in FIG. 4, Compound 1 at doses of 20 and 40 mg/kg significantly reduced total traveling distance in the 30-minute sLMA test. Compound 1 has a calculated $TD_{50}$ of 44 mg/kg. These data suggest that Compound 1 at a dose of 20 mg/kg and 40 mg/kg reduces locomotor activity.

Example 5. Effect of Compound 1 on Seizure Frequency in Scn2a$^{Q54}$ Mouse Model of Elevated Persistent Sodium Current The objective of this study was to assess the potential anti-convulsant properties of Compound 1 (0.3 mg/kg, 1 mg/kg, 3 mg/kg, or 10 mg/kg, p.o.) in a genetic model of increased $I_{Na}$ mouse line. SCN2A and SCN8A gain of function mutations that increase $Na_V1.2$ and $Na_V1.6$ persistent sodium current ($I_{Na}$), respectively, have been identified in children with various forms of epileptic encephalopathy (EE). The Scn2a$^{Q54}$ mouse line was developed as a model of increased $I_{Na}$ by introducing 3 consecutive point mutations in the full length SCN2A gene (G879Q, A880Q, L881Q). The mutated gene encodes a large pathological neuronal persistent $I_{Na}$ in the CNS sodium channel $Na_V1.2$ (Kearney et al., A gain-of-function mutation in the sodium channel gene Scn2a results in seizures and behavioral abnormalities, Neuroscience, 2001, 102 (2): 307-317; PMID 11166117). Like the EE patients, Scn2a$^{Q54}$ mice exhibit early life seizures, status epilepticus and premature death.

1. Materials and Methods i. Animals

Scn2a$^{Q54}$ transgenic mice were generated as described and are maintained as a congenic line on the C57BL/6J (Jax #000664) background (B6.Q54) (Kearney et al., 2001; PMID 11166117). For experiments, F1 generation mice were produced by crossing B6.Q54 hemizygous transgenic males with SJL/J (Jax #000686) females and genotyping for the Scn2a$^{Q54}$ transgene. Experimental animals used in this study were male and female postnatal day 18-21 (P18-21) mice, with the majority being P19-P20.

Mice were group-housed in a specific pathogen free mouse facility under standard laboratory conditions (14/10-hour light/dark cycle). Mice had access to food and water ad libitum, except during the experimental period for seizure monitoring. All manipulations were performed during the animals' light cycle.

ii. Compound Formulation and Dosing

Dosing solutions were freshly formulated on the morning on the study. Dosing solution contained 0.5% methylcellulose with 0.2% Tween-80 was made with 1 mL 10% Tween-80 (in ddH20) and 49 mL 0.5% methylcellulose (in ddH20) either with or without (vehicle) Compound 1 (0.3 mg/kg, 1 mg/kg, 3 mg/kg, or 10 mg/kg). Each animal received a single administration of vehicle or Compound 1 by oral gavage.

iii. Study Design

For seizure monitoring, two mice were placed into a monitoring cage (23 cm×13 cm) and two side-view cameras were placed to record baseline spontaneous seizure activity. Prior extensive video electroencephalography (EEG) monitoring of Scn2a$^{Q54}$ transgenic mice demonstrated strong correlation between behavioral and EEG seizures (K=0.988) (Anderson et al., Antiepileptic activity of preferential inhibitors of persistent sodium current, Epilepsia, 2014, 55 (8): 1274-1283 (PMID: 24862204); Kearney et al., 2001). After the 30-minute recording, mice were administered Compound 1 or vehicle and returned to their home cage. After 30 minutes, the two mice were returned to the monitoring cage and recorded for an additional 30 minutes to assess post-treatment seizure activity. The number of focal motor seizures with forelimb clonus and repetitive movements lasting 1-5 seconds, and generalized tonic-clonic seizures (GTCS) with rearing and falling lasting approximately 1 minute were counted. Seizures were scored offline by an observer blinded to treatment and pre/post status of the video file.

iv. Calculations and Statistical Analysis

The numbers of seizures before and after treatment were counted for each animal by a reviewer blinded to treatment and pre/post status of the video record. Mice that had less than three seizures or more than 35 seizures during the baseline period were excluded from the analysis as pre-defined in the study design. Statistical analysis was conducted using two-way repeated measures ANOVA and Sidak's multiple comparisons, with $p<0.05$ considered statistically significant (GraphPad Prism 8.4). Change in average seizure frequency was determined by averaging each group and then computing relative change as [(avg. post−avg. pre)/avg. pre], expressed as a percentage.

v. Plasma and Brain Collections

At the conclusion of the seizure observation period, animals were sacrificed and blood was collected and transferred into heparin blood collection tubes. Blood collection tubes were centrifuged at 5,000 g for 10 minutes and plasma was removed to 1.5 mL Eppendorf tubes on dry ice. Following blood collection, the brain was removed, frozen on dry ice and stored individually in 1.5 mL Eppendorf tubes. Rodent plasma and brain tissues were stored at −80° C. until shipped on dry ice for bioanalysis.

2. Results

Figure 5:
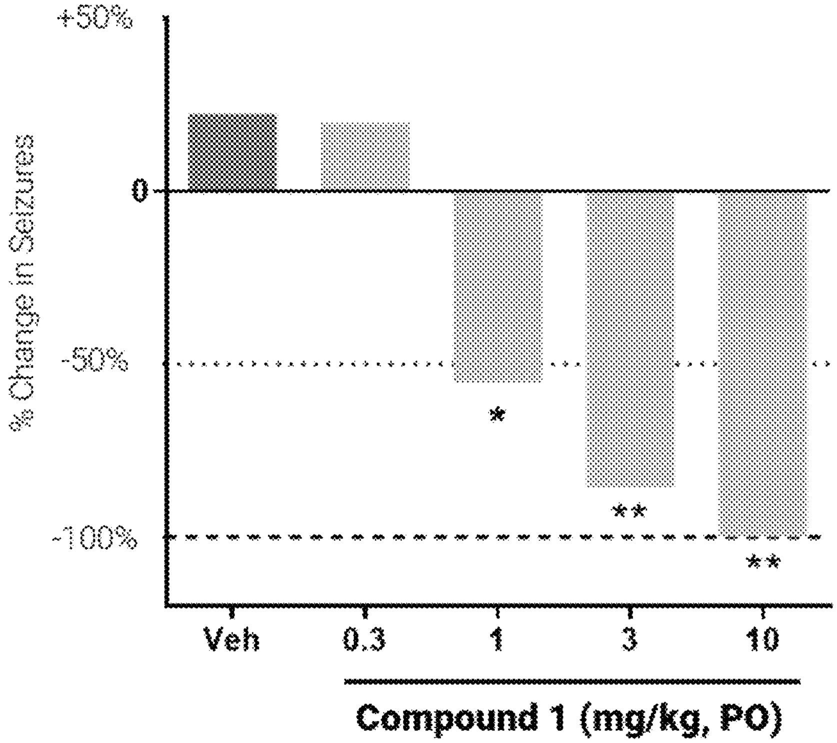
FIG. 5 depicts effect of Compound 1 on reducing focal motor seizure frequency in Scn2a$^{Q54}$ mouse model of elevated persistent sodium current. Sidak's post-hoc comparison test; *P<0.05 vs. Veh., **P<0.001 vs. Veh.

Seizure frequency was measured in Scn2a$^{Q54}$ mice for 30 minutes before and then again 30 minutes after treatment with Compound 1 or vehicle. Treatment of Scn2a$^{Q54}$ mice with Compound 1 at 1, 3 and 10 mg/kg resulted in a significant reduction in seizure frequency compared to pre-treatment baseline (FIG. 5). At doses of 1 mg/kg and above, there was a 50% reduction in seizure frequency with no mice showing any seizures after dosing with 10 mg/kg.

Overall, Compound 1 had a significant anti-seizure effect in Scn2a$^{Q54}$ mice. These data suggest that Compound 1 exhibits anti-convulsive activity in a model of elevated persistent $I_{Na}$ and has potential for treatment of epilepsy, particularly in syndromes with elevated persistent sodium current as a genetic etiology.

Example 6. Effect of Compound 1 on Audiogenic Induced Seizures in Scn8a$^{N1768D/+}$ Transgenic Mouse Model The objective of this study was to evaluate the effect of Compound 1 on audiogenic induced seizures in the N1768D gain-of-function SCN8A epileptic encephalopathy mouse model (D/+). The Scn8a$^{N1768D/+}$ transgenic mouse carries a gain-of-function mutation in $Na_V1.6$ (Wagnon et al., Convulsive seizures and SUDEP in a mouse model of SCN8A epileptic encephalopathy, Human Molecular Genetics, 2015, 24 (2): 506-515).

Both male and female N1768D (D/+) mice, 8-12 weeks old, were used in the study. Compound 1 was administered orally (p.o.) at three doses (1 mg/kg, 3 mg/kg, 10 mg/kg) and also vehicle 1 hour prior to testing. The mice were randomized such that at the completion of the study each individual mouse had been evaluated at each test dose of Compound 1 and vehicle. A minimum of 3 days was allowed to elapse before retesting the mice. At the time of testing, mice were taken from their home cage and transferred to a clean test cage located in a separate testing room where they were allowed to acclimate for about 20 seconds before the onset of the acoustic stimulus. To induce audiogenic seizures, a 15 kHz signal was generated using Tone Generator software (NCH Software, Inc.), amplified using a Kinter K3118 stereo amplifier (Kinter USA), and converted to sound using a small 3-watt speaker lowered into the testing chamber. The stimulus was applied for 30 seconds unless a seizure was detected before the 30-second time point, in which case the audiogenic stimulus was terminated. Videos of the event were recorded using a laptop webcam. On the final day of testing, brains and plasma were collected from the D/+ mice immediately after audiogenic seizure testing to determine concentrations of Compound 1. A separate cohort of 8 age-matched WT mice were also included (n=2/dose level) to achieve a sample size of n=4 for PK for each dose level. Brain and plasma specimens were submitted for bioanalytical analysis.

Figure 6:
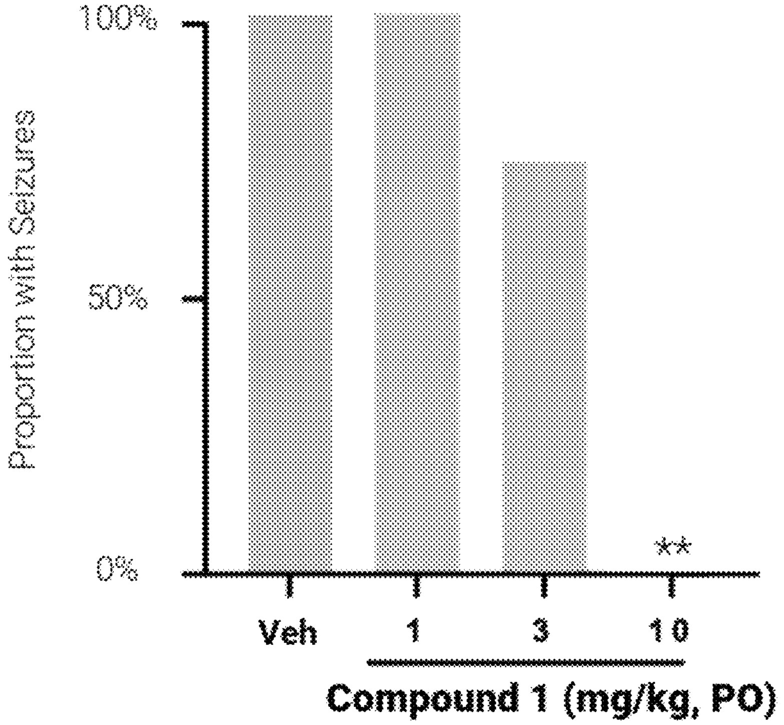
FIG. 6 depict inhibition of audiogenic seizures by Compound 1 (1-10 mg/kg, p.o.). Results of in vivo proof of concept studies in N1768D D/+ mice showing Compound 1 inhibition of audiogenic evoked seizures. **Significant protection vs. Veh; $\chi^2_2$=16.0, Fisher's p=0.0002.

As shown in FIG. 6, oral administration of Compound 1 resulted in dose dependent inhibition of audiogenic seizures in D/+ mice. Compound 1 at 10 mg/kg (p.o.) produced complete protection from audiogenic seizures.

Overall, Compound 1 was shown to inhibit audiogenic seizures in a dose-dependent manner in a human knock-in mouse model of SCN8A epileptic encephalopathy (EIEE13). These studies demonstrate the efficacy of Compound 1 in inhibiting seizures associated with a gain-of-function SCN8A mutation.

Example 7. Effect of Compound 1 on Time to Pentylenetetrazole Induced Seizure Pentylenetetrazole (PTZ), a GABA receptor antagonist, can be used to create a common, chemically-induced seizure model, a model of generalized seizure. The PTZ experiments were performed on heterozygous Kcnq2 K556E, Kcnc1 R320H, or Hcn1 M294L mice, or their wild type (WT) littermates (P35-P45, both male and female).

Mice were acclimated to experimental area for minimum 30 minutes before experimentation. All experiments were performed between 10:00 am and 12:30 pm. The treatment compounds and PTZ were always prepared fresh.

Mice were randomly assigned either to different doses of Compound 1 (10 mg/kg, 1 mg/kg, or 0.1 mg/kg) or a vehicle control containing 0.5% methylcellulose and 0.2% tween 80, and dosed via oral gavage (p.o). Compound 1 and the vehicle control were administered 60 minutes before the injection of PTZ.

Retigabine (4 mg/kg) was also used as a positive control in the Kcnq2 K556E mice. The retigabine was dissolved in 10% DMSO and 10% solutol, and administered by intraperitoneal (i.p.) route 30 minutes before the injection of PTZ.

PTZ (100 mg/kg) was dissolved in saline and administered subcutaneously (s.c) to the experimental mice. The latency to full tonic-clonic seizure with hind limb extension was measured. The animals were sacrificed either at the time of hind limb extension or 40 minutes after PTZ administration if no hind limb extension was recorded.

Data were analyzed using a Mantel-Cox log-rank test. Brain tissue and plasma were collected from some mice for each dose of Compound 1 at the PTZ endpoint for PK analysis.

Figure 7A:
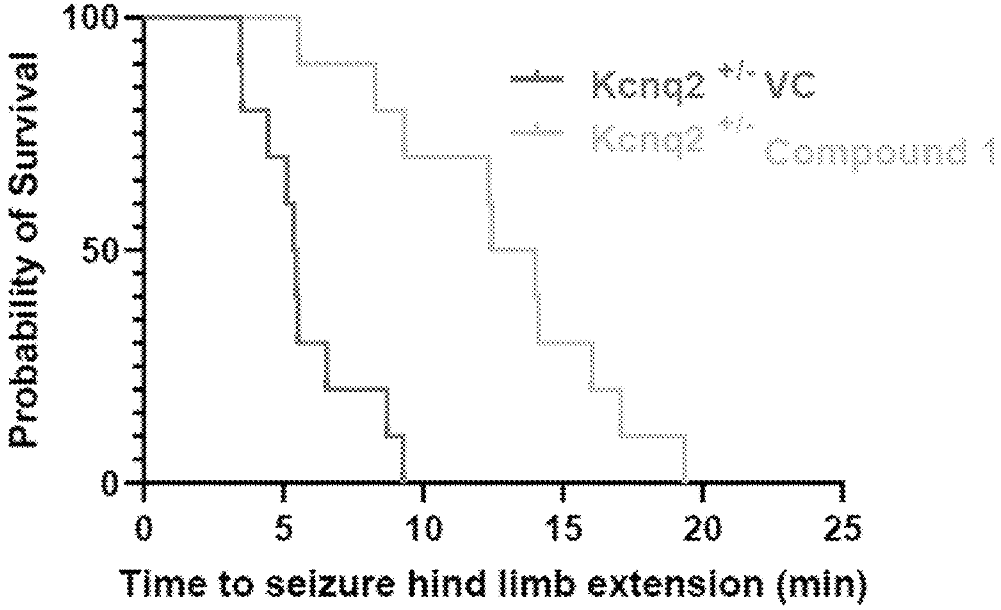
FIGS. 7A-7B depict effect of Compound 1 (10 mg/kg) in KCNQ2 K556E and KCNC1 R320H PTZ seizure models.
Figure 7B:
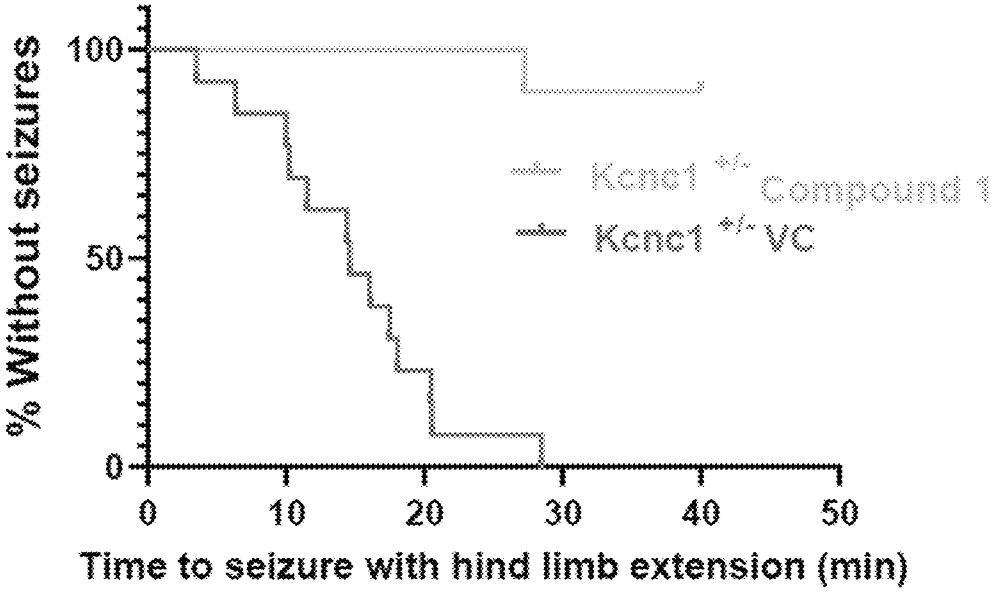

As shown in FIG. 7A-7B, at a dose of 10 mg/kg, Compound 1 is highly efficacious in KCNQ2 (FIG. 7A) and KCNC1 (FIG. 7B) seizure models.

Example 8. Compound 1 has Potent Anticonvulsant Activity with Improved Protective Index Relative to Standard of Care Sodium Channel Blockers This study compared the effects of Compound 1 on sodium current ($I_{Na}$), intrinsic neuronal excitability, and protection from evoked seizures to two standard voltage-gated sodium channel ($Na_V$) blockers to determine whether a preferential persistent $I_{Na}$ inhibitor, such as Compound 1, would exhibit improved preclinical efficacy and tolerability.

Inhibition of $I_{Na}$ was characterized using patch clamp analysis. The effect on intrinsic excitability was measured using evoked action potentials recorded from hippocampal CA1 pyramidal neurons in mouse brain slices. Anticonvulsant activity was evaluated using the maximal electroshock seizure (MES) model, and tolerability was assessed by measuring spontaneous locomotor activity (sLMA). All assays are described in the preceding examples.

1. Compound 1 Potently Inhibits Persistent $I_{Na}$

Figure 8A:
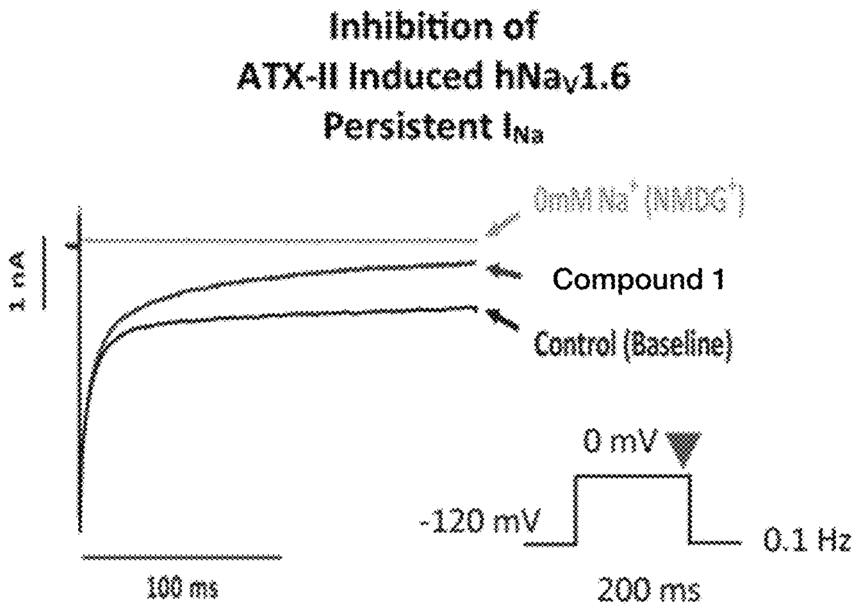
FIGS. 8A-8D show that Compound 1 exhibits potent inhibition of $Na_V$1.6 persistent sodium current ($I_{Na}$). Compound 1 ATX-II-evoked h$Na_V$1.6 persistent $I_{Na}$ (FIG. 8A) and h$Na_V$1.6-N1768D (developmental or epileptic encephalopathy variant)-expressed persistent $I_{Na}$.
Figure 8B:
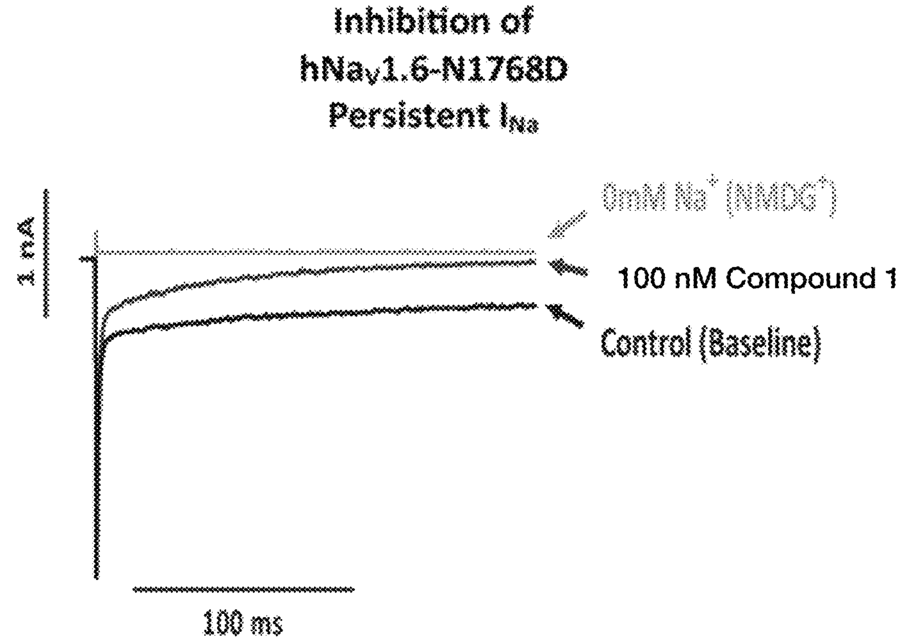
Figure 8C:
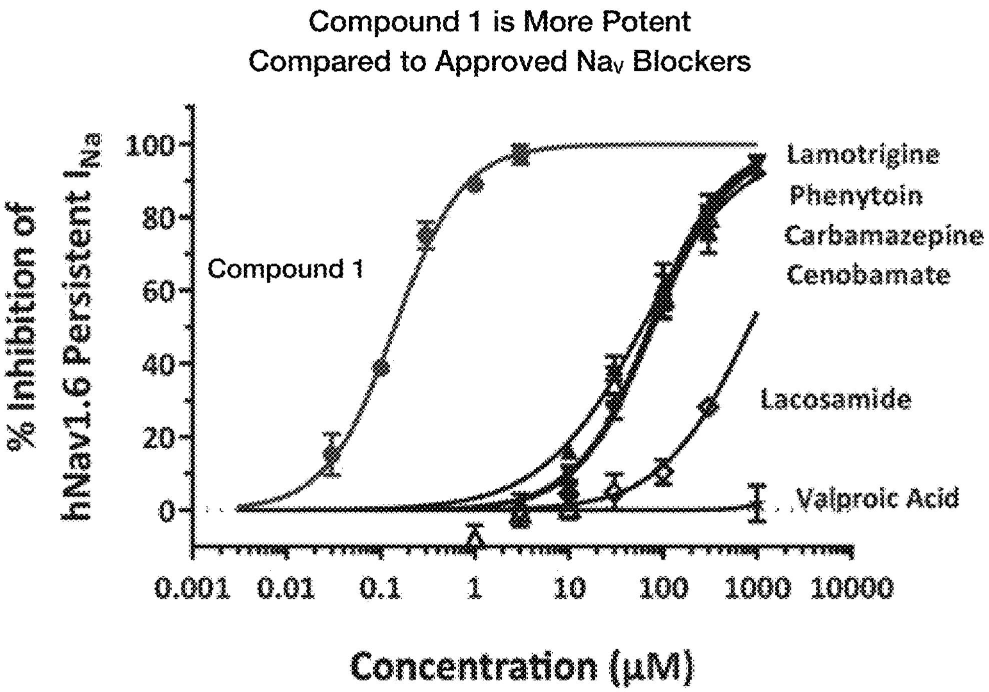
Figure 8D:
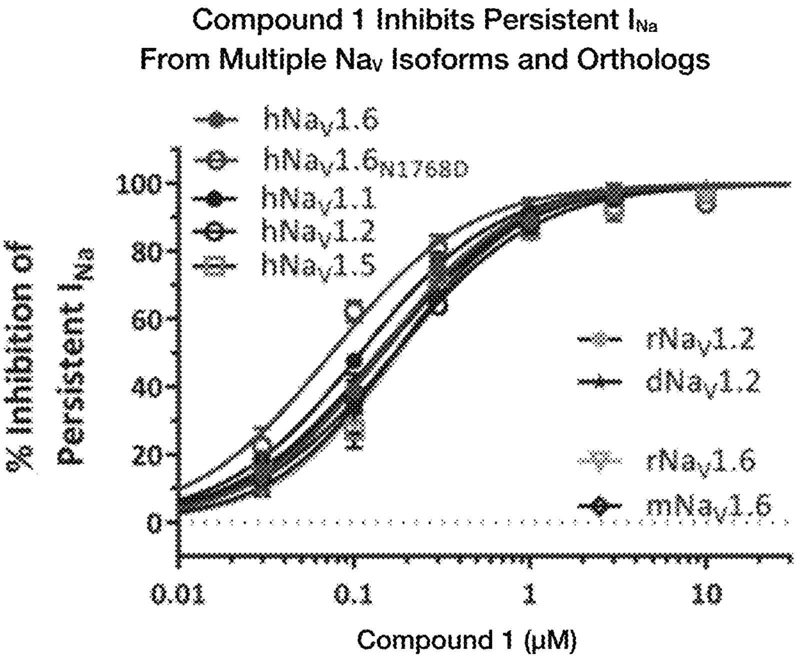

Compound 1 potently inhibited ATX-II-induced persistent $I_{Na}$ expressed by wild-type h$Na_V$1.6 (FIG. 8A; $IC_{50}$=141 nmol/L) and persistent $I_{Na}$ expressed by the DEE mutant h$Na_V$1.6-N1768D (FIG. 8B; $IC_{50}$=75 nmol/L). Persistent $I_{Na}$ was activated from resting/closed channel conformations by maintaining a hyperpolarized holding potential (−120 mV). Removal of extracellular sodium ($NMDG^+$) completely inhibited sodium-dependent conductance. The potency of Compound 1 for ATX-II or N1768D persistent $I_{Na}$ was at least 550-fold greater than that of standard $Na_V$-targeting AEDs (FIG. 8C, Table 1). Compound 1 displayed similar potency for the inhibition of persistent $I_{Na}$ expressed by other human $Na_V$ isoforms (h$Na_V$1.1 (NP_008851.3), h$Na_V$1.2 (NP_066287.2), h$Na_V$1.5 (NP_000326.2)) as well as rat, dog, and mouse orthologs (r$Na_V$1.2 (NP_036779.1), d$Na_V$1.2 (XP_013966299.1), m$Na_V$1.6 (NP_035453.2), and r$Na_V$1.6 (NP_062139)), with $IC_{50}$ values ranging 109-180 nmol/L (FIG. 8D).

Figure 9A:
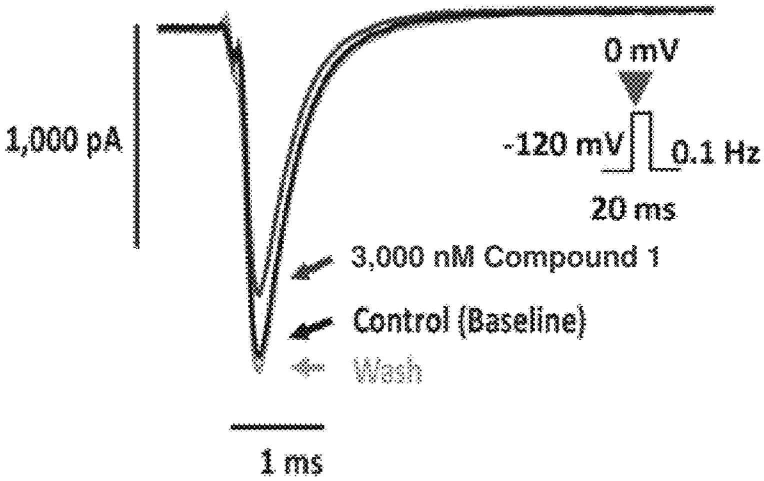
FIGS. 9A-9F depict that Compound 1 demonstrates increased preference for h$Na_V$1.6 persistent sodium current ($I_{Na}$) over peak $I_{Na}$ relative to the standard $Na_V$-targeting antiepileptic drugs carbamazepine (CBZ) and lamotrigine (LTG). Inhibition of peak $I_{Na}$ assessed using assays for tonic block (resting state.

2. Compound 1 Exhibits Enhanced Preference for the Inhibition of Persistent $I_{Na}$ Over Peak $I_{Na}$ The inhibition of peak $I_{Na}$ was investigated using three assays with increasing levels of h$Na_V$1.6 activation. Tonic block of physiologic peak $I_{Na}$ is measured at a low stimulation frequency (0.1 Hz) from resting/closed channel conformations (FIG. 9A). Compound 1 exhibited tonic block with lower potency ($IC_{50}$=8470 nmol/L), demonstrating 60-fold preference for persistent $I_{Na}$ (Table 1). Compound 1 also exhibited preference for persistent $I_{Na}$ over peak $I_{Na}$ tonic block for other human $Na_V$ soforms: h$Na_V$1.1 (173-fold, 109 nmol/L vs. 18 870 nmol/L), h$Na_V$1.2 (80-fold, 172 nmol/L vs. 13 690 nmol/L), and h$Na_V$1.5 (>174-fold, 172 nmol/L vs. 12% inhibition at 30 000 nmol/L).

Figure 9B:
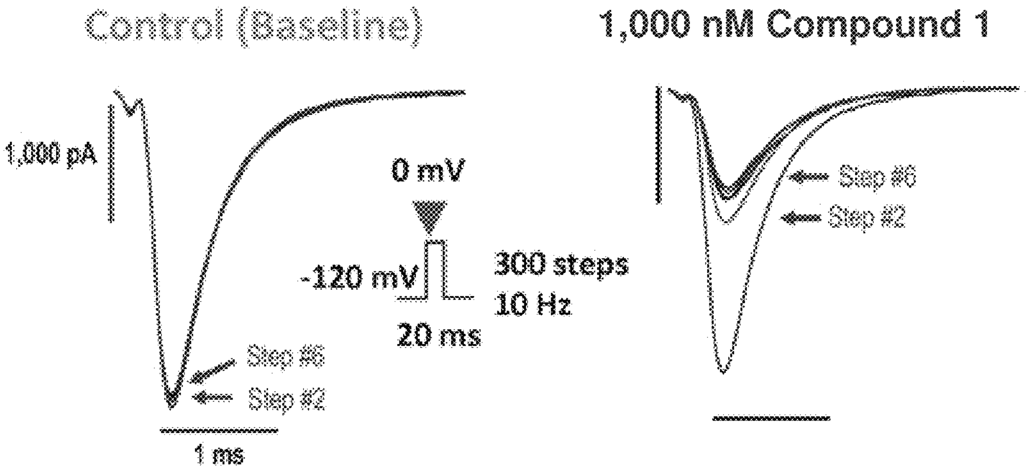

The use-(activity-) dependent block of h$Na_V$1.6 by Compound 1 was measured using a train of short voltage steps at a frequency of 10 Hz to represent periods of elevated neuronal firing (e.g., during a seizure) where use-dependent block of peak $I_{Na}$ may have a therapeutic benefit. Compound 1 exhibited use-dependent block of h$Na_V$1.6 peak Iva with an $IC_{50}$ of 271 nmol/L and maximum inhibition of 75% (blue trace, FIG. 9B; Table 1). Notably, use-dependent block was not observed for either CBZ or LTG at a stimulation frequency of 10 Hz (blue trace, FIG. 9E and FIG. 9F, respectively). Use-dependent block could be observed for CBZ by increasing the frequency of depolarization from 10 Hz to either 30 Hz or 50 Hz. The degree of use-dependent block observed for Compound 1 was significantly greater compared with CBZ at all frequencies, suggesting an increased ability of Compound 1 to respond to acute changes in neuronal activity (acute hyperexcitability).

Figure 9C:
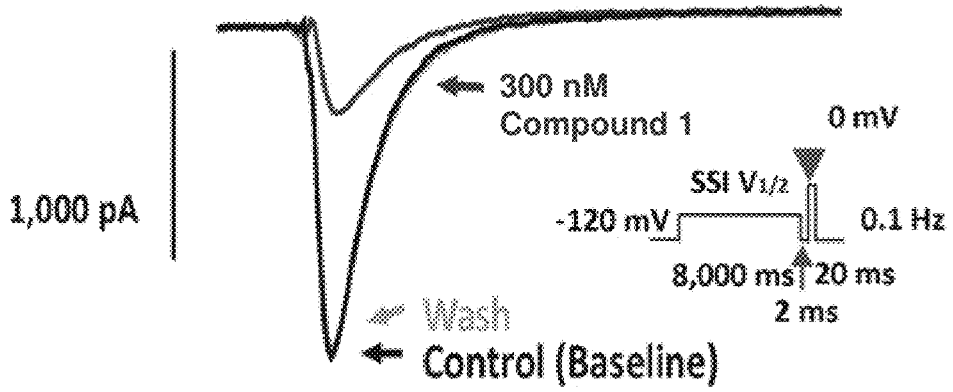
Figure 9D:
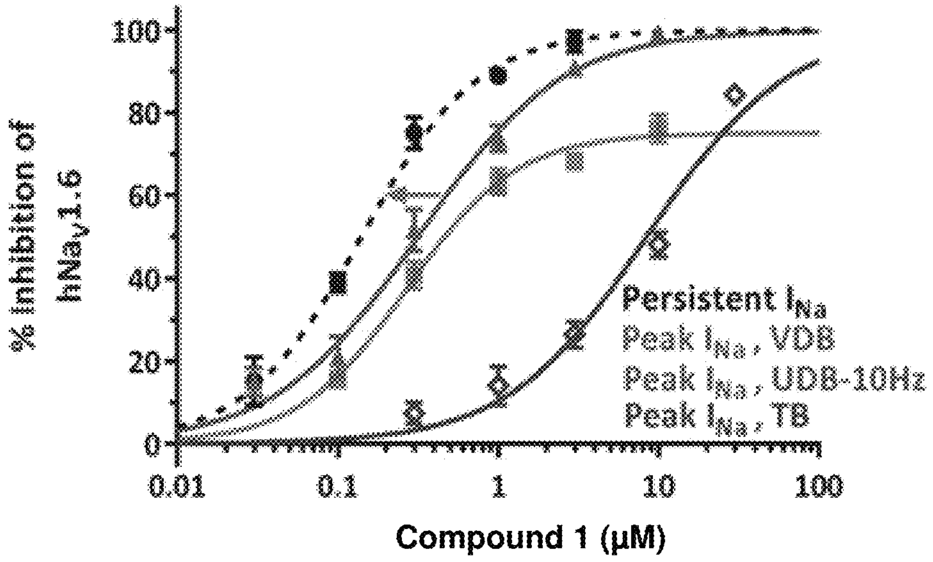
Figure 9E:
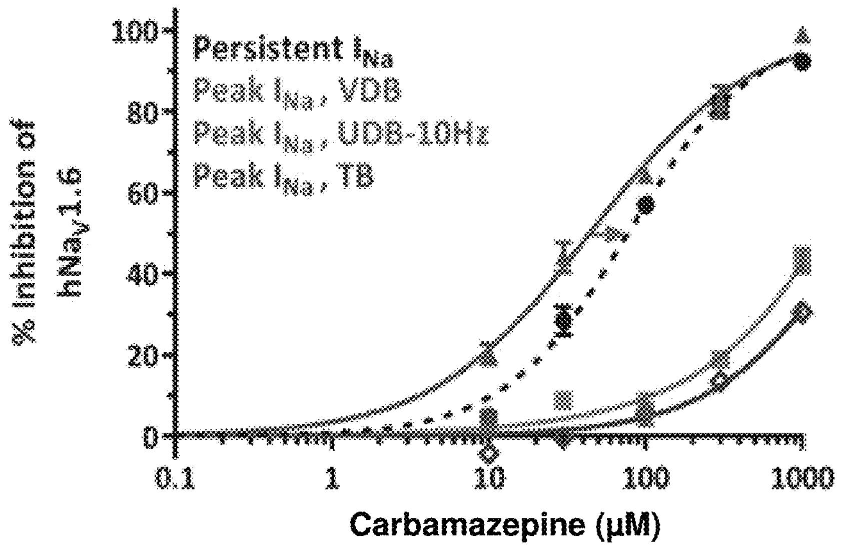
Figure 9F:
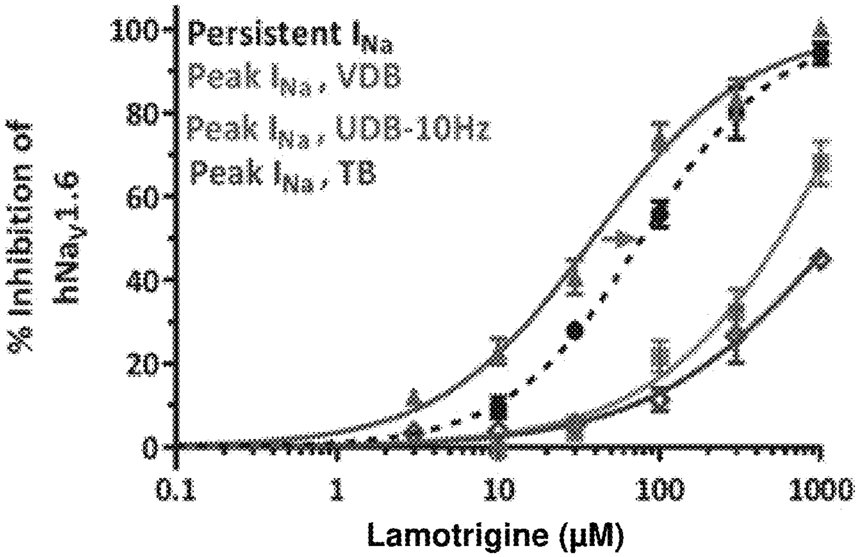

The peak $I_{Na}$ voltage-dependent block assay employs a sustained, nonphysiological inactivating voltage step to midpoint ($V_{1/2}$) of the steady-state inactivation (determined in real time for each cell) to place half the channels into the inactivated state. This approach effectively explores isoform selectivity, as the differences in voltage-sensing that regulate binding site access are minimized, and the extended time allows for most inhibitors to reach binding equilibrium. Compound 1 exhibited a voltage-dependent block $IC_{50}$ of 317 nmol/L (FIG. 9C, Table 1). These data demonstrate a 2.2-fold preference for persistent $I_{Na}$ is retained as channels are inactivated (red arrow, FIG. 9D; Table 1). Compound 1 exhibited a similar preference for persistent $I_{Na}$ over peak $I_{Na}$ voltage-dependent block for $hNa_V1.1$ (6.3-fold), $hNa_V1.2$ (8.2-fold), and $hNa_V1.5$ (5.8-fold). Compound 1 also induced a concentration-dependent stabilization of $hNa_V1.6$ inactivation, as evidenced by a significant left shift in the Vin of the steady-state inactivation curve: shifts of −2.6 mV for dimethylsulfoxide (DMSO)/control, 6.2 mV for 0.3 μmol/L Compound 1, and −11.7 mV for 1 μmol/L Compound 1. Only minor shifts in the $V_{1/2}$ of the activation curve were observed: shifts of −1.3 mV for DMSO/control, −2.3 mV for 0.3 μmol/L Compound 1, and −2.7 mV for 1 μmol/L Compound 1. These data suggest Compound 1 enhances fast inactivation with minimal effects on activation gating.

A panel of standard $Na_V$-targeting AEDs was tested in the same persistent $I_{Na}$ and peak $I_{Na}$ assays. Compared with Compound 1, all tested inhibitors were less potent in all assays (Table 1). The moderate persistent $I_{Na}$ preference observed for other $I_{Na}$ inhibitors in the tonic block assay (eightfold to 30-fold) was lost as the channels transitioned to more activated/inactivated states, as in the voltage-dependent block assay (0.3-fold to 0.9-fold preference). Notably, both CBZ and LTG were more potent for voltage-dependent block peak $I_{Na}$ compared to persistent $I_{Na}$ (0.6-fold and 0.5-fold, respectively), demonstrating a preference for peak $I_{Na}$ under these conditions.

3. Compound 1 Reduces Intrinsic Excitability of Wild-Type CA1 Pyramidal Neurons

The preferential inhibition of persistent $I_{Na}$ is predicted to reduce neuronal hyperexcitability without excessive disruption of AP morphology, including AP amplitude, as this feature depends on the expression of peak $I_{Na}$. The effects of Compound 1 and CBZ on neuronal intrinsic excitability were measured using evoked AP firing (input-output curves) at the equivalent effective concentrations of the peak $I_{Na}$ voltage-dependent block $IC_{50}$ (Table 1). At 0.3 μmol/L, Compound 1 significantly reduced the intrinsic excitability as measured by the number of evoked APs (FIG. 10A). In contrast, 45 μmol/L CBZ produced a more robust reduction in neuronal excitability (FIG. 10D). CBZ caused a more pronounced reduction in AP amplitude compared to Compound 1, suggesting greater inhibition of peak $I_{Na}$ (FIG. 10F). These data demonstrate that although both agents generate a reduction in the excitability of wild-type CA1 neurons, Compound 1 reduces excitability in a manner that likely maintains physiological activity over a broader range of concentrations than CBZ by leaving a greater proportion of peak $I_{Na}$ intact.

Figure 11A:
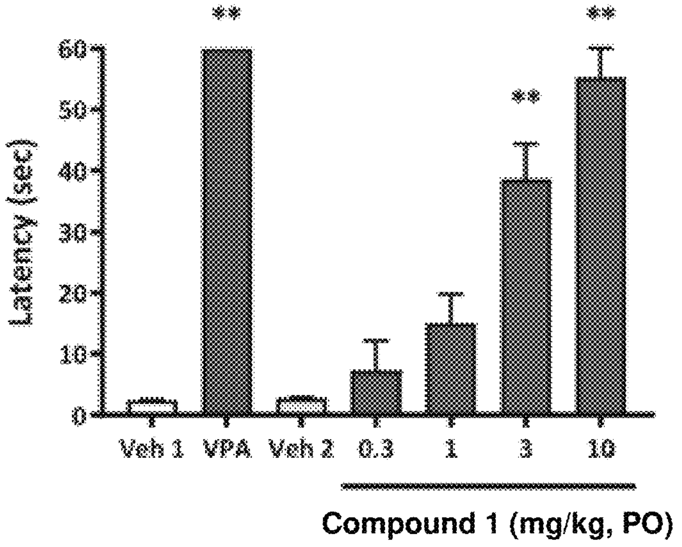
FIGS. 11A-11E depict that Compound 1 has an improved preclinical protective index (PI) compared to carbamazepine (CBZ) or lamotrigine (LTG). Compound 1 (0.3-10 mg/kg po) produced dose-dependent increases in latency to tonic extension seizures (FIG. 11A) and decreases in the relative number of mice developing seizures (FIG. 11B) in the maximal electroshock seizure (MES) model. Maximal effects were equivalent to the positive control valproic acid (VPA; 400 mg/kg ip).

4. Compound 1 Achieves Full Anticonvulsant Efficacy without Affecting Locomotor Activity To assess whether a persistent $I_{Na}$ inhibitor with the in vitro profile of Compound 1 can prevent seizures, anticonvulsant activity in the mouse MES model was investigated. This model has predictive validity for clinical anticonvulsant activity. Compound 1 was compared to the standard $Na_V$-targeting AEDs, CBZ and LTG. Compound 1 produced dose-dependent protection (increase in latency) of mice against MES-induced tonic hindlimb seizures (FIG. 11A). Near complete protection was achieved at 10 mg/kg, where

TABLE 1

Compound 1 demonstrates greater potency and preference for $hNa_V1.6$ persistent $I_{Na}$ compared with standard $Na_V$-targeting antiepileptic drugs.

| | Persistent $I_{Na}$ | Peak $I_{Na}$ TB | Ratio to Pers. $I_{Na}$ | Peak $I_{Na}$ UDB-10 Hz | Ratio to Pers. $I_{Na}$ | Ratio to Peak $I_{Na}$ (TB) | Peak $I_{Na}$ VDB | Ratio to Pers. $I_{Na}$ |
|---|---|---|---|---|---|---|---|---|
| Compound 1 | 141 (1.2) | 8,472 (1.0) | 60 | 271 (1.3) max 75% | 2 | 31 | 317 (1.0) | 2.2 |
| Cenobamate | 71,690 (1.1) | 1,719,000 (1.1) | 24 | 749,300 (0.7) | 11 | 2.3 | 66,710 (0.9) | 0.9 |
| Phenytoin | 59,820 (0.8) | n/a** | — | 876,600 (0.6) | 15 | — | 47,780 (1.0) | 0.8 |
| Carbamazepine | 77,490 (1.1) | 2,307,000 (1.0) | 30 | 1,418,000 (0.9) | 18 | 1.6 | 44,370 (0.9) | 0.6 |
| Oxcarbazepine | 123,700 (1.0) | 1,035,000 (1.7) | 8 | n.d. | — | — | 42,000 (1.1) | 0.3 |
| Lamotrigine | 78,480 (1.0) | 1,249,000 (0.8) | 16 | 515,800 (1.0) | 6.6 | 2.4 | 39,090 (0.9) | 0.5 |
| Lacosamide | 832,700 (0.9) | n/a** | — | 682,200 (1.3) | 0.8 | — | 269,300 (1.2) | 0.3 |
| Valproic acid | 2% @ 1 mM | 11 @ 1 mM | — | 8% @ 1 mM | — | — | 18% @ 1 mM | — |

Abbreviations:

$IC_{50}$, half-maximal inhibitory concentration;

$I_{Na}$, sodium current;

MAX, maximum;

n.d., not determined;

n/a, not available;

$Na_V$, voltage-gated sodium channel;

TB, tonic block;

UDB, use-dependent block;

VDB, voltage-dependent block.

[a] Could not be determined due to compound solubility limit.

Figure 11B:
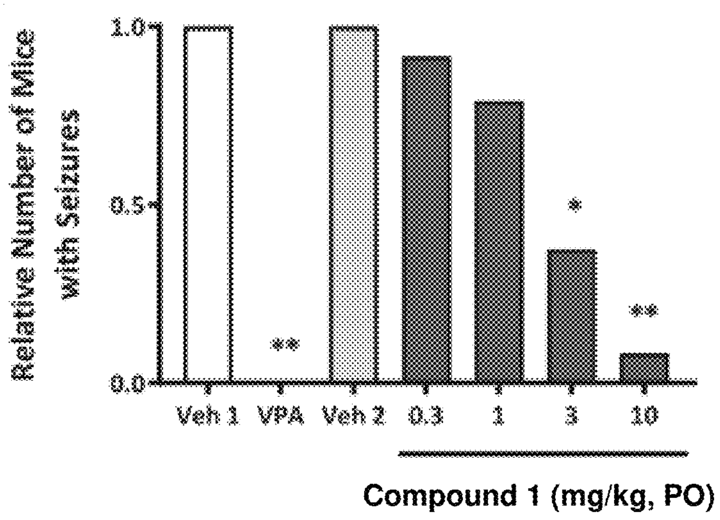

11 of 12 mice did not exhibit tonic seizures (FIG. 11B). This effect was comparable to that observed with the positive control, VPA. The calculated $ED_{50}$ value for increasing latency to tonic extension seizures was 2 mg/kg, with calculated $EC_{50}$ values of 90.1 ng/ml (17.9 nmol/L free) and 116 ng/g (4.3 nmol/L free) in plasma and brain, respectively (Table 2).

TABLE 2

Compound 1 has improved preclinical PI compared to CBZ and LTG.

| | Efficacy (MES) | | | Tolerability (sLMA) | | | | |
|---|---|---|---|---|---|---|---|---|
| | $ED_{50}$ (mg/kg) | $EC_{50}$ (free brain, nM) | $EC_{50}$ (free plasma, nM) | $TD_{50}$ (mg/kg) | $TC_{50}$ (free brain, nM) | $EC_{50}$ (free plasma, nM) | PI (Brain) | PI (Plasma) |
| Compound 1 | 2.0 | 4.3 | 18 | 44 | 69.7 | 309 | 16.2 | 17.3 |
| LTG | 3.4 | 2,754 | 3,188 | 26.5 | 12,853 | 20,455 | 4.7 | 6.4 |
| CBZ | 5.0 | 2,410 | 5,560 | 37.6 | 14,350 | 19,010 | 5.9 | 3.4 |

Note:
Mean drug concentrations associated with MES $ED_{50}/EC_{50}$ and sLMA $TD_{50}/TC_{50}$ are shown. PI was calculated as brain $TC_{50}$/brain $EC_{50}$.

Abbreviations: CBZ, carbamazepine; $EC_{50}$, half-maximal efficacious concentration; $ED_{50}$, half-maximal efficacious dose; LTG, lamotrigine; MES, maximal electroshock seizure; PI, protective index; sLMA, spontaneous locomotor activity; $TC_{50}$, half-maximal tolerated concentration; $TD_{50}$, half-maximal tolerated dose.

CBZ and LTG also provided dose-dependent protection of mice against MES-induced tonic hindlimb seizures, with CBZ (30 mg/kg) protecting all mice and LTG protecting eight of 12 mice at the highest dose tested (10 mg/kg). The calculated $ED_{50}$ values for increased latency to tonic extension seizures were 5 and 3.4 mg/kg for CBZ and LTG, respectively (Table 2).

Figure 11C:
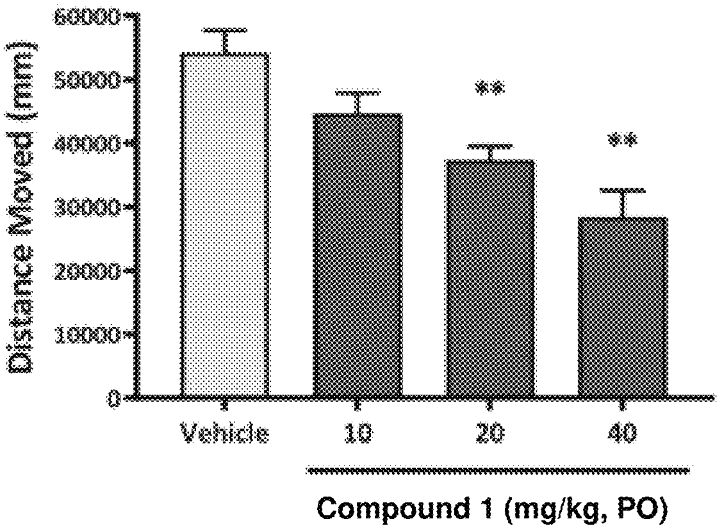

To determine the tolerability of Compound 1, the effects on sLMA were measured. Compound 1 produced reductions in the distance moved at 20 and 40 mg/kg (FIG. 11C). The dose of Compound 1 (10 mg/kg) that resulted in seizure prevention in 11 of 12 mice had no effect on locomotor function. The dose of Compound 1 required to reduce sLMA by 50% ($TD_{50}$) was calculated to be 44 mg/kg. The Compound 1 concentrations associated with the 50% effect ($TC_{50}$) were calculated to be 1553 ng/ml (308.9 nmol/L free) and 1899 ng/g (69.7 nmol/L free) in plasma and brain, respectively (Table 2).

CBZ and LTG also produced dose-dependent reductions in sLMA, with $ED_{50}$ values of 37.6 and 26.5 mg/kg, respectively (Table 2). Notably, CBZ produced a significant reduction in sLMA at the dose required for complete seizure prevention.

Figure 11D:
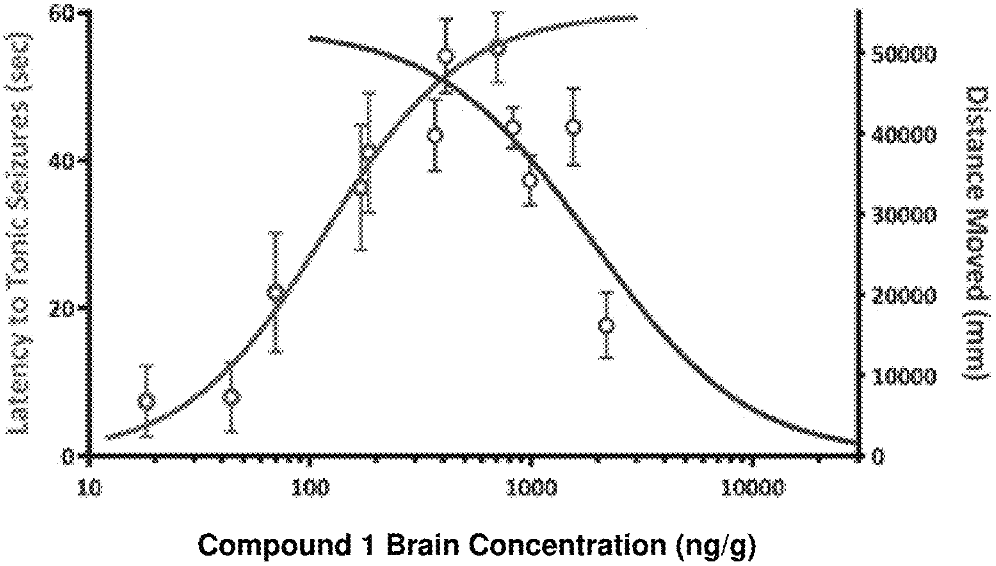
Figure 11E:
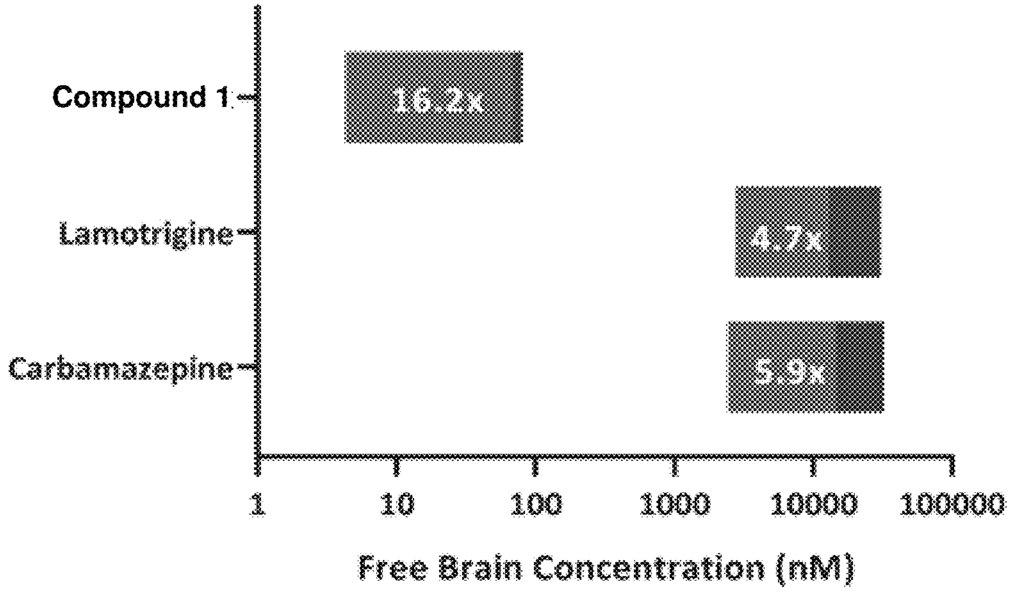

The ratio of tolerability to efficacy (PI) was calculated for each molecule by dividing the brain or plasma $TC_{50}$ for reduction in sLMA by the brain or plasma $EC_{50}$ for increasing latency to seizures (FIG. 11D). Compound 1 had a significantly improved PI of approximately 16-fold (based on calculated free brain concentrations) and 17-fold (based on free plasma concentrations). This represents an improvement in PI compared with both CBZ (brain, 5.9×; plasma, 3.4×) and LTG (brain, 4.7×; plasma, 6.4×; FIG. 11E).

5. Combination of Compound 1 with Standard of Care Sodium Channel Blockers Produces Greater Efficacy In Vivo and does not Alter Tolerability The effect of Compound 1 in combination with standard of care sodium channel blocker CBZ was tested in the MES model and sLMA assay.

Figure 12A:
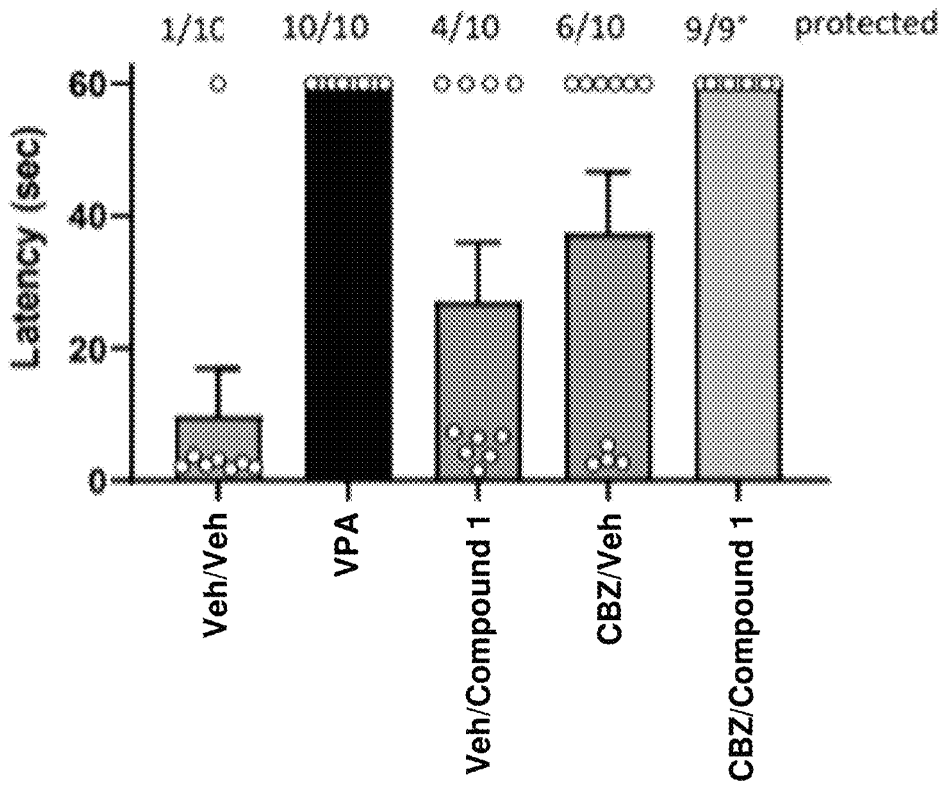
FIGS. 12A-12B depict that combination of Compound 1 with standard of care sodium channel blocker carbamazepine ("CBZ") produces greater efficacy in vivo (FIG. 12A) and does not alter tolerability (FIG. 12B). For FIG. 12A, n=8/group veh, n=10 Compound 1, Mann-Whitenet (VPA), ANOVA/Dunn (Compound 1), *p<0.05 vs. Veh/Veh, p<0.005 vs. Veh/Veh. For FIG. 12B, n=10/group, 4 excluded from CBZ/Compound 1 for ataxia, ANOVA/Dunn, p<0.01 vs. Veh.

In the MES model, 2 mg/kg of Compound 1 and 5 mg/kg of CBZ were tested either alone or in combination in CD-1 mice. Compound 1 and CBZ were prepared individually in 35% HPBCD. Animals were dosed 30 minutes prior to the MES test with either: 1) 35% HPBCD i.p.+35% HPBCD p.o.; 2) 35% HPBCD i.p.+Compound 1 p.o.; 3) CBZ i.p.+35% HPBCD p.o.; 4) CBZ i.p.+Compound 1 p.o.; 5) positive control groups valproate (VPA) or saline i.p. 30 minutes prior to the MES test. All solutions were dosed at 10 mL/kg. Just before the start of the MES test, possible side effects, such as overt sedation, were recorded. As shown in FIG. 12A, the combination of Compound 1 and CBZ was more efficacious in the MES model than Compound 1 or CBZ alone. Exposures were consistent for all groups and at intended levels.

Figure 12B:
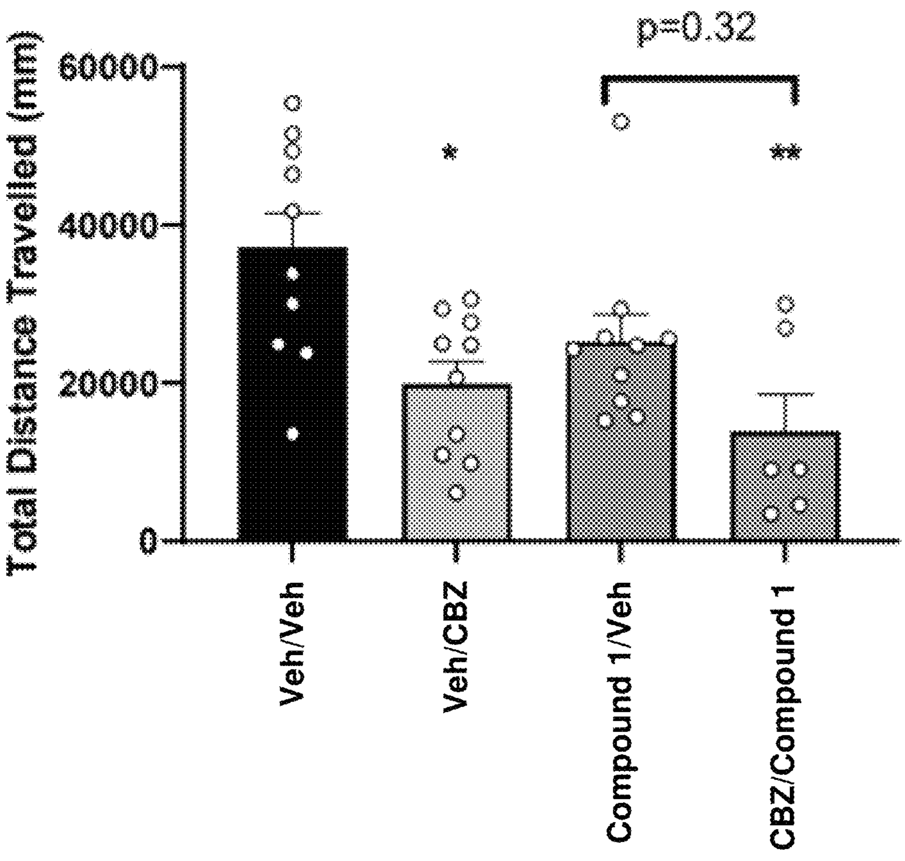

In the sLMA assay, 10 mg/kg of Compound 1 and 30 mg/kg of CBZ were tested either alone or in combination in CD-1 mice. Compound 1 and CBZ were prepared individually in 35% HPBCD. Animals were dosed 30 minutes prior to the sLMA test with either: 1) 35% HPBCD i.p.+35% HPBCD p.o.; 2) 35% HPBCD i.p.+Compound 1 p.o.; 3) CBZ i.p.+35% HPBCD p.o.; 4) CBZ i.p.+Compound 1 p.o. All solutions were dosed at 10 mL/kg. Just before the start of the sLMA test, possible side effects such as overt sedation were recorde. As shown in FIG. 12B, the combination of Compound 1 and CBZ does not impair tolerability. Exposures were consistent for all groups and at intended levels.

Example 9. Study on Safety, Tolerability, Efficacy, and Pharmacokinetics of Compound 1 in Patients with Developmental and Epileptic Encephalopathies Compound 1-mediated blockade of the persistent sodium current ($I_{Na}$), as shown in animal models, can lead to antiseizure efficacy at well tolerated doses. By specifically blocking persistent $I_{Na}$, Compound 1 can provide greater efficacy in seizure reduction compared to standard of care (SOC) sodium channel blockers (SCB) that are less selective for persistent $I_{Na}$. Because Compound 1 is less active at peak current, it will be better tolerated than SOC, causing fewer on-target AEs. Accordingly, Compound 1 can be effective and well tolerated when utilized as first line monotherapy, allowing for improved patient outcomes and continuity of treatment from infancy to adulthood.

Preclinical data and emerging clinical data demonstrate that Compound 1 has enhanced selectivity for disease-state $Na_V$ channel hyperexcitability, wide therapeutic window, and convenient auto-titration regimen with stable PK, which all contribute to its superior safety and efficacy in animal models, and expected therapeutic utility in human patients with epilepsy, such as SCN2A, SCN8A, and other DEEs.

The purpose of this study is to evaluate the safety and tolerability of Compound 1, to assess the effect of Compound 1 on the frequency of motor seizures, and to characterize the pharmacokinetics (PK) of oral suspension Compound 1 in patients with developmental and epileptic encephalopathies (DEE).

This is an open-label proof of concept study with 3 cohorts of DEE patients (SCN2A, SCN8A, and Tuberous Sclerosis Complex (TSC)) between 2 years old and 17 years old. There will be an 8-week screening period followed by a 16-week treatment period comprised of 8-week dose optimization period and 8-week maintenance period, and a 4-week safety follow-up period or roll-over into LTE. The rationale for 16-week treatment period is based on the current knowledge of Compound 1 pharmacokinetics, which is predicted to potentially take about 6 weeks to achieve 90% steady state. The 8-week dose optimization period allows for adjusting concomitant SCBs and the additional 8 weeks will allow for evaluation of tolerability and efficacy signal during the maintenance period.

For efficacy endpoint, each cohort will be reviewed as individual cohorts in parallel to one another and analyzed separately. The primary objective is the safety and tolerability of Compound 1 with a principle secondary objective being the efficacy of Compound 1 as determined by average monthly (28 day) motor seizure frequency as compared to baseline during the maintenance period. The major elements of the study schedule is provided in Table 3.

TABLE 3

Major elements of the study schedule.

| Visit | Study Day/Week | Assessments |
|---|---|---|
| Screening | Week −8 to Day −1 | Informed Consent/Assent Form<br>Confirmation of entry criteria by Eligibility Review Committee<br>General and safety (labs, ECG, exams, vitals, disease-specific history, etc.) |
| Baseline period | Week −4 to Day −1 | Seizure diary collection: establish baseline seizure frequency and confirm eligibility<br>Video EEG (+ASSR) |
| Baseline | Day 1 | Confirmation of entry criteria<br>First dose received<br>General and safety (labs, PK, ECG, exams, vitals, etc.)<br>Measures of non-seizure symptoms |
| Treatment period | Weeks 1-14<br>In clinic visit Week 4, 8, and 14<br>Telephone call Week 2 and 6 | In clinic visits: General and safety (labs, PK, ECG, exams, vitals, AEs, etc.)<br>Measures of non-seizure symptoms<br>Seizure diary review<br>Weight check and dose adjustment as needed (Week 4 and 8 only)<br>Telephone call: AEs, con meds, seizure diary review<br>Video EEG (+ASSR) around Week 8 and 14 |
| Safety follow-up | Week 18 (telephone call) | AEs |

Dosing will be guided by preclinical data (targeting concentration between $EC_{50}$ and $EC_{90}$ from MES model) and modeling from adult PK data, and duration of dose optimization phase will be predicated on adult PK data. During the dose optimization period, the dose adjustment will be as follows. The starting dose will be 1 mg/kg/day of Compound 1. If within the first 6 weeks, there is no improvement in seizure frequency (30% reduction) and no issues with tolerability, the dose may be increased to 1.5 mg/kg/day. If there are tolerability issues, the dose will be dropped back down to 1 mg/kg/day. If during the dose optimization period, there are tolerability issues at 1 mg/kg/day of Compound 1, then first decrease concomitant SCB by ≥25% while continue dosing of Compound 1 and evaluate after 1 week. If tolerability issues persist, then decrease concomitant SCB by another ≥25% while continue dosing of Compound 1 and evaluate after 1 week. If tolerability issues still persist, then decrease Compound 1 to 0.5 mg/kg/day. If there is no tolerability at 0.5 mg/kg/day of Compound 1, patient will be withdrawn from the study.

The participants will be chosen based on the following eligibility criteria for inclusion: (1) has a documented diagnosis of SCN2A, SCN8A, or TSC; (2) male and female patients aged ≥2 and ≤17 years at the time of informed consent; (3) history of, on average, ≥8 motor seizures per month during the 3 months immediately prior to the screening based on Investigator's assessment, and ≥8 motor seizures during the 1-month baseline period based on diary collection (motor seizures are defined as: tonic, tonic-clonic, focal with secondary generalization, focal with motor symptoms and epileptic spasms, not including myoclonic only or absence); (4) agreement for enrollment by Epilepsy Study Consortium Eligibility Review Committee; (5) on stable doses of antiseizure medications (ASM) for 1 month prior to screening, no more than 2 of which can be sodium channel blocking ASMs; and (6) agree to keep all antiseizure therapies (ASMs, CBD/THC products, VNS settings, ketogenic or other diet parameters, etc.) stable throughout the course of the study unless instructed by Investigator or per protocol. Benzodiazepines used at a daily frequency to treat seizures are considered an ASM. If using CBD and/or THC products, CBD and/or THC products must be at stable dose for 1 month prior to screening. If using VNS, VNS must have been placed at least 3 months prior to screening with stable setting for at least 1 month prior to screening and VNS is not counted as an ASM. If a patient is on a ketogenic or other diet for management of seizures, the patient must have started the diet at least 3 months prior to screening with stable parameters for at least 1 month prior to screening and diets are not counted as an ASM.

The eligibility criteria for exclusion include: (1) has a loss of function mutation and/or clinical evidence that prior exposure to a sodium channel blocking medication worsened seizures; (2) has two or more episodes of convulsive status epilepticus requiring hospitalization and intubation in the 6 months prior to screening; (3) history of left bundle branch block, Brugada syndrome, or congenital heart disease (a non-clinically significant PFO is not considered an exclusion); (4) has an abnormal ECG reading, including a QT interval with Fridericia correction method (QTcF)>xxx msec (males) or >xxx msec (females) at screening or prior to randomization; (5) has any of the following abnormal laboratory test result at Screening: a serum total bilirubin value >1.5× the upper limit of normal (ULN) and/or a serum alanine aminotransferase (ALT) or aspartate aminotransferase (AST) value >2×ULN; (6) has any prior use of gene therapy; (7) has received any other experimental or investigational drug, device, or other therapy within 30 days or 5 half-lives (whichever is longer) prior to screening; (8) has previously or is currently participating in any other Compound 1 clinical trial; (9) has a known hypersensitivity to any component of the formulation of Compound 1; and (10) prohibited medications/classes forthcoming.

Figure 13A:
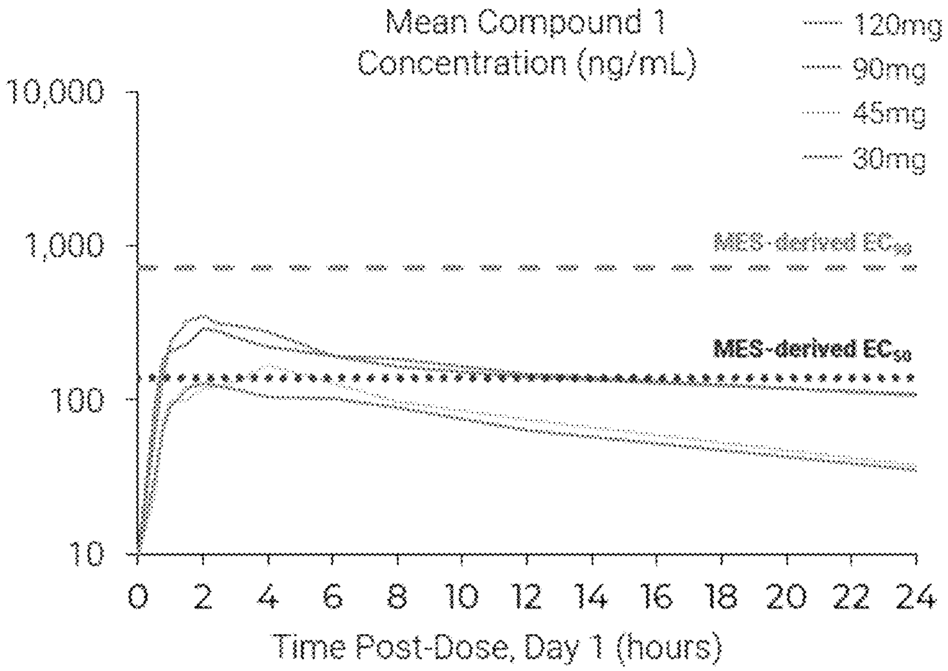
FIGS. 13A-13B depict that Compound 1 exposures above therapeutic range after single dose (FIG. 13A) and approaching steady-state after 28 days of dosing with once daily dosing and auto-titration (FIG. 13B). $C_{Max}$ in FIG. 13B is representative of concentration at 2.5 hours post-dose.
Figure 13B:
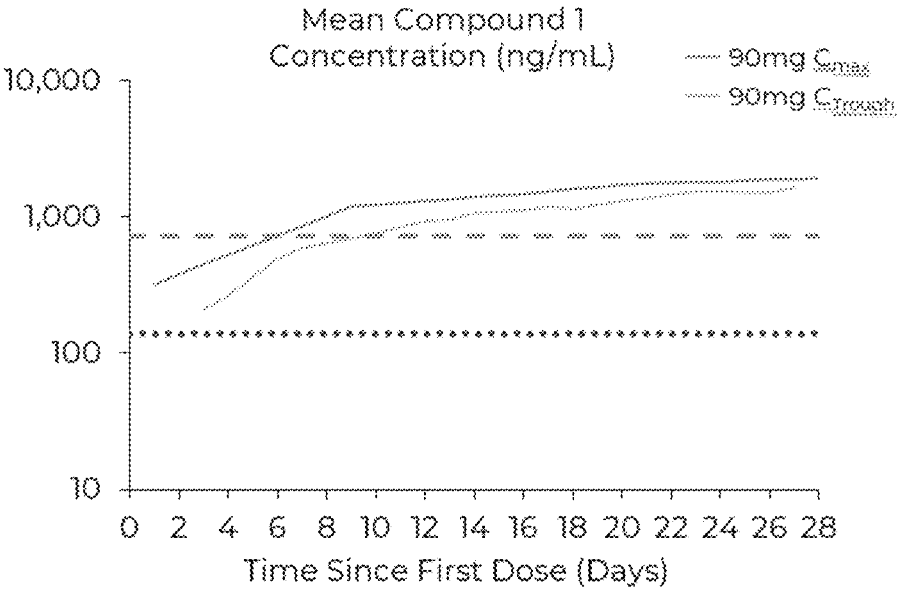

Preliminary data from the first 12 participants enrolled in the study showed Compound 1 exposures above predicted therapeutic levels on Day 1 (FIG. 13A) and that Compound 1 approaches steady state after 28 days of dosing with once daily dosing and auto-titration, well above predicted therapeutic exposure (FIG. 13B).

Example 10. Study on Safety, Tolerability, Pharmacokinetics and Food Effect of Compound 1 in Healthy Volunteers The purpose of this study was to evaluate safety, tolerability, and pharmacokinetics (PK) of single and multiple ascending doses of Compound 1, as well as the effect of food on PK of a single dose in healthy adults.

This was a 3-part Phase 1 clinical trial in healthy participants aged 18-55 years. Parts A and B were randomized, placebo-controlled and evaluated the effects of single (2.5-150 mg) and multiple (30-120 mg, 14 days QD (every day)) ascending oral doses of Compound 1, respectively. Part C was an open-label, randomized, crossover design evaluating the PK of a single oral dose (90 mg) in fasted and fed states. In Parts A (n=64) and B (n=32), participants were randomized 3:1 to Compound 1 or placebo (n=8/cohort). In Part C (n=16), participants were randomized 1:1 to one of two treatment sequences receiving a single dose of 90 mg Compound 1 in the fed (following a high-fat/high calorie meal) or fasted (≥10 hours after the last, and 4 hours before the next, meal) state.

In this clinical trial, the PD activity of Compound 1 was evaluated in healthy participants using electroencephalogram (EEG)-based auditory steady-state response (ASSR) measures and resting state EEG (qEEG)-based spectral power measures under eyes-open and eyes-closed conditions.

The ASSR-based phase-locking factor (PLF) data suggested that Compound 1 plasma exposures sufficient to modulate the ASSR signal were reached at doses of 90 mg and 120 mg Compound 1 QD. In Part B, a reduction from baseline in PLF at Day 14 (2 hours 35 minutes postdose) of approximately 30% and 60% was observed in the 90-mg and 120-mg Compound 1 QD groups, respectively. The decrease in PLF seemed to be dose dependent between the 90-mg and 120-mg QD dose levels. A statistical analysis was not performed on this measure. No statistically significant differences between the placebo and any Compound 1 dose level were observed for ASSR-based absolute evoked gamma power. Nonetheless, these data suggested that Compound 1 exposures reached with the 90-mg and 120-mg QD dose regimens were sufficient to modulate cortical excitatory/inhibitory balance in the brain in healthy participants.

Resting state EEGs (qEEGs) were only collected in the 120-mg single-dose and multiple-dose cohorts in Part A and Part B, respectively. Increases from baseline in the Delta (1.5-6 Hz) and Theta (6-8.5 Hz) band spectral power were observed in both the 120-mg Compound 1 single dose group and 120-mg Compound 1 QD group.

112 participants were enrolled across the trial (n=88 Compound 1, n=24 placebo). Compound 1 was well-tolerated with no clinically significant safety findings in vital signs, clinical laboratory results, physical exams, electrocardiograms (ECGs), or Columbia-suicide severity rating scale (C—SSRS) data. Treatment emergent adverse events (TEAEs) were mild (>92%); the most common being catheter-site related, headache and dizziness. Typical $Na_V$ blocker events were experienced by 34% of participants and more frequently reported at higher doses (120 mg and 150 mg).

Exposure increased dose proportionally over the evaluated dose range. Compound 1 rapidly appeared in plasma with time to observed maximum concentration ($t_{max}$) between 2 and 3 hours, and detectable levels over a dose interval. Administration of a 90-mg dose in the fed state resulted in a slight increase in $C_{max}$ (9%), delay in $t_{max}$ (4 vs 2.5 h), and a modest increase in AUC (14%) compared to fasted state.

Compound 1 was well tolerated in healthy participants at single doses up to 150 mg (fasted) in Part A, at multiple doses of up to 120 mg QD for 14 days (fasted) in Part B, and at a single dose of 90 mg in the fed and fasted states in Part C. These findings further indicate that Compound 1 can be administered without regard for food.

Example 11. A Phase 1 Trial Evaluating the Safety, Tolerability, Pharmacokinetics and Pharmacodynamics of Compound 1 in Healthy Volunteers This was a 2-part randomized, placebo-controlled Phase 1 trial in healthy participants aged 18-55 years. Part A evaluated the effects of 90 mg Compound 1 over 28 days (QD) vs. placebo. Part B evaluated the effects of oxcarbazepine (OXC) in combination with 120 mg Compound 1 (QD) vs. OXC alone over 28 days. PD effects were examined on quantitative EEG (qEEG; resting and vigilant conditions) and stimulated EEG using auditory steady state response (ASSR). A total of 48 participants were enrolled; Part A, n=30; Part B, n=18.

There were no clinically significant safety findings in vital signs, physical exams, ECGs, or C—SSRS data. TEAEs were mostly mild or moderate (100% Part A; 96% Part B). Compound 1 was well tolerated in healthy adults at 90 mg in Part A. In Part A, there were 35 TEAEs across 13 participants: 71% mild in severity, 29% moderate, 0% severe.

In Part B, there were 74 TEAEs across 16 participants: 51% mild in severity, 45% moderate, 4% severe. TEAEs were observed in 13 (92.9%) patients receiving OXC+ Compound 1 and in 3 (75%) patients receiving OXC+ Placebo. A review of ALT/AST increases and rhabdomyolysis did not identify a causal association to Compound 1. One Part B participant experienced 3 study drug related SAEs leading to study drug discontinuation. The majority of AEs including SAEs in Part B were considered to be due to coadministration of projected supratherapeutic doses of Compound 1 (120 mg) with OXC, and likely additive $Na_V$ blocking effects.

Compound 1 90 mg administered for 28 days approached steady state in Part A. Exposure to OXC and its primary metabolite, 10-Hydroxycarbamezapine, appeared to be similar when administered concomitantly with Compound 1 vs administered alone in Part B, as is illustrated in the table below. Specifically, the table below shows Day 7 Compound 1 exposure summary (120 mg, Part B).

| Analysis | Parameter | OXC + Compound 1 (N = 13) | OXC + Placebo (N = 4) |
|---|---|---|---|
| Oxcarbazepine | $C_{max}$ (ng/mL) | 1,776 (37.6) | 1,525 (21.1) |

-continued

| Analysis | Parameter | OXC + Compound 1 (N = 13) | OXC + Placebo (N = 4) |
|---|---|---|---|
| | $AUC_{last}$ (nag*h/mL) | 5,564 (40.2) | 5,828 (16.4) |
| 10-Hydroxycarbamezapine | $C_{max}$ (ng/mL) | 17,017 (31.1) | 18,175 (21.3) |
| | $AUC_{last}$ (nag*h/mL) | 151,595 (38.9) | 172,658 (13.8) |

Compound 1 exposure did not appear to be altered with OXC coadministration in Part B (data not shown). Part A PK findings demonstrate a 13-fold increase in Compound 1 concentrations over the human-equivalent dose required to achieve efficacy as measured in preclinical maximal electroshock seizure models.

PD biomarker changes observed on qEEG and ASSR were exposure dependent; qEEG changes were observed across all spectral frequencies. Statistically significant differences between placebo and Compound 1 were observed in Part A on qEEG (Delta and Theta power) and ASSR (phase-locking-factor (PLF) and Evoked Power). Effects on both low frequency qEEG power and ASSR appeared to be Compound 1 concentration dependent. Statistically significant differences were observed in Part B participants receiving OXC+Compound 1 vs. OXC alone on qEEG Delta, but not qEEG Theta or ASSR. PD findings indicate CNS modulation and expected target engagement for Compound 1 across multiple qEEG measures.

Example 12. A Phase 1, Open-Label Trial in Healthy Participants to Evaluate the Drug-Drug Interaction Potential of Compound 1

This is a Phase 1, open-label trial in healthy male or female participants to investigate the effect of coadministration of Compound 1 on the PK of caffeine, dextromethorphan, and midazolam, and the effect of coadministration of ciprofloxacin and itraconazole on the PK of Compound 1. The trial will be conducted in 2 parts: non-randomized single-sequence crossover (Part A) and randomized parallel design (Part B). Each part will consist of 3 distinct periods: Screening, Intervention, and Follow-up.

Objectives and Endpoints

| Objective | Endpoint |
|---|---|
| Primary | |
| To determine the effect of multiple doses of Compound 1 on the PK of caffeine, dextromethorphan, and midazolam and their metabolites (Part A only) | The PK parameters of caffeine, dextromethorphan, and midazolam (as well as their metabolites) derived from plasma concentration-time profiles in the presence and absence of Compound 1, and will include area under the plasma concentration-time curve (AUC) from time zero to infinity ($AUC_{inf}$)<br>maximum observed plasma concentration ($C_{max}$)<br>Additional PK parameters may include, but are not limited to, the following:<br>AUC from time zero to the time of the last quantifiable concentration ($AUC_{last}$)<br>time of the maximum observed plasma concentration ($t_{max}$)<br>apparent plasma terminal elimination half-life ($t_{1/2}$)<br>metabolite to parent ratios based on $AUC_{inf}$ |
| To determine the effect of multiple doses of ciprofloxacin and itraconazole on the PK of Compound 1 (Part B only) | The PK parameters of Compound 1 derived from the plasma concentration-time profile in the presence and absence of each of the co-administered drugs, and will include<br>$AUC_{inf}$<br>$AUC_{last}$<br>$C_{max}$<br>Additional PK parameters may include, but are not limited to, the following:<br>AUC from time zero to 24 hours ($AUC_{0-24}$)<br>$t_{max}$<br>$t_{1/2}$<br>metabolite to parent ratios based on $AUC_{inf}$ |
| Secondary | |
| To assess the safety and tolerability of Compound 1 when administered alone and when co-administered with caffeine, dextromethorphan and midazolam, and with, ciprofloxacin, or itraconazole in healthy participants | Incidence and severity of adverse events (AEs)<br>Changes in vital signs measurements<br>Changes in clinical laboratory test results<br>Changes in electrocardiogram (ECG) parameters |

-continued

| Objective | Endpoint |
| --- | --- |
| | Incidence of suicidal ideation or behavior measured by the Columbia-Suicide Severity Rating Scale (C-SSRS) |

Screening Period

Participants will be screened for eligibility during the 27-day screening phase (from Day-28 to Day-2). Prior to any clinical trial procedures, participants will provide written informed consent. Screening assessments will be completed to assess participants' eligibility to enter the trial.

Intervention Period

Part A

Fifteen participants meeting all inclusion criteria and none of the exclusion criteria will attend the clinical site on Day-1 for Admission procedures and will remain domiciled at the clinical site from thereon through the discharge date. Single oral doses of caffeine 100 mg, dextromethorphan 30 mg, and midazolam 2 mg will be administered on the morning of Day 1. On Days 2 to 18, participants will receive a daily morning dose of Compound 1 120 mg orally. On Day 16, single oral doses of caffeine 100 mg, dextromethorphan 30 mg, and midazolam 2 mg will be administered, followed immediately by Compound 1. Safety assessments, and PK sampling for the CYP probes and their metabolites (caffeine/paraxanthine, dextromethorphan/dextrorphan, midazolam/1-hydroxymidazolam), and for Compound 1 will be performed. Participants will be discharged on Day 19 after satisfactory safety review and completion of trial-related procedures.

Part B

Forty-five participants meeting all inclusion criteria and none of the exclusion criteria will be randomized to one of the 3 treatment groups of 15 participants each. The participants in each treatment group will attend the clinical site on Day-1 for Admission procedures and will remain domiciled at the clinical site from thereon through the discharge date. The participants will be administered trial drugs orally as follows:

- Treatment Group 1: A single dose of Compound 1 120 mg on Day 1.
- Treatment Group 2: Ciprofloxacin 500 mg twice daily (Days 1 to 18). A single dose of Compound 1 120 mg on Day 5.
- Treatment Group 3: Itraconazole 200 mg twice daily (Day 1) and 200 mg once daily (Days 2 to 18). A single dose of Compound 1 120 mg on Day 5.

Safety assessments, and PK sampling for Compound 1, ciprofloxacin, and itraconazole, will be performed. Following satisfactory safety review and completion of trial related procedures, participants will be discharged from the clinic on Day 19.

Safety Follow-Up Period

The Safety Follow-up Period will span from discharge from the clinic until 28 days (±2 days) after the last dose administration. On Day 26 (±2 days) in Part A and Part B, participants will return to the clinic for the final clinical trial assessments At the end of the Safety Follow-up Period, participants will receive a telephone call to assess AEs and concomitant medications.

Pharmacokinetic Assessments

Blood samples will be collected for measurement of plasma concentrations of Compound 1, caffeine (and metabolite paraxanthine), dextromethorphan (and metabolite dextrorphan), midazolam (and 1 hydroxymidazolam), ciprofloxacin, and itraconazole. Samples collected may also be used to evaluate safety related to concerns arising during or after the clinical trial. Samples may also be used for additional exploratory method development and/or metabolite characterization purposes.

Adverse and Serious Adverse Events

AEs will be reported by the participant (or, when appropriate, by a caregiver, surrogate, or the participant's legally authorized representative) and may include:

- Any abnormal laboratory test results (hematology, clinical chemistry, or urinalysis) or other safety assessments (eg, ECG, radiological scans, vital signs measurements), including those that worsen from baseline, considered clinically significant in the medical and scientific judgment of the investigator (ie, not related to progression of underlying disease).
- Exacerbation of a chronic or intermittent pre-existing condition including either an increase in frequency and/or intensity of the condition.
- New conditions detected or diagnosed after study drug administration even though it may have been present before the start of the clinical trial.
- Signs, symptoms, or the clinical sequelae of a suspected drug-drug interaction.
- Signs, symptoms, or the clinical sequelae of a suspected overdose of either study drug or a concomitant medication.
- Overdose per se will not be reported as an AE/SAE unless it is an intentional overdose taken with possible suicidal/self-harming intent. Such overdoses should be reported regardless of sequelae.

Each AE and SAE reported during the clinical trial will be assigned to one of the following categories:

- Mild: An event that is easily tolerated by the participant, causing minimal discomfort, and not interfering with everyday activities
- Moderate: An event that causes sufficient discomfort and interferes with normal everyday activities
- Severe: An event that prevents normal everyday activities. An AE that is assessed as severe should not be confused with a SAE. Severe is a category utilized for rating the intensity of an event; and both AEs and SAEs can be assessed as severe Example 13. A Phase 2, Double-Blind, Randomized Clinical Trial to Explore the Safety, Tolerability, Efficacy, and Pharmacokinetics of Compound 1 in Pediatric Participants with Developmental and Epileptic Encephalopathies Followed by an Open-Label Extension This Phase 2, multicenter, double-blind, randomized clinical trial, followed by an open-label extension (OLE), is designed to explore the safety, tolerability, efficacy, and PK of Compound 1 when administered to pediatric participants who have seizures associated with early-onset SCN2A-DEE and SCN8A-DEE.

Eligible male and female participants aged 2 to 18 years, inclusive, with a diagnosis of early-onset SCN2A DEE (n≈10) and SCN8A-DEE (n≈10) will be enrolled in the clinical trial in 2 distinct cohorts.

Part A (randomized, double-blind) will consist of the following periods: Screening Period (including 28-day Baseline Observation Period), Double-Blind Treatment Period, and Safety Follow-up Period. Part B (OLE) will consist of the following periods: OLE Treatment Period and Safety Follow-up Period.

Objectives and Endpoints

PART A: RANDOMIZED, DOUBLE-BLIND

| Objective | Endpoint |
|---|---|
| **Primary** | |
| To evaluate the safety and tolerability of Compound 1 in pediatric participants with DEEs | Incidence and severity of treatment-emergent adverse events (TEAEs) |
| **Secondary** | |
| To assess the effect of Compound 1 on the frequency of countable motor seizures in pediatric participants with DEEs | Changes from baseline in monthly (28-day) motor seizure frequency |
| To characterize the PK of Compound 1 oral suspension in pediatric participants with DEEs | Plasma concentrations of Compound 1 |
| **Exploratory** | |
| To explore the effect of Compound 1 on additional efficacy outcomes in pediatric participants with DEEs | Changes from baseline in other types of seizures<br>Changes from baseline in video electroencephalogram (vEEG) characteristics, including but not limited to electrographic seizures, interictal epileptiform discharges, and background frequency<br>Clinical Global Impression-Improvement (CGI-I) score at each postdose timepoint<br>Caregiver Global Impression-Improvement (CgGI-I) score at each postdose timepoint |
| To explore the effect of Compound 1 on nocturnal seizures in pediatric participants with DEEs | Percent change from Baseline in nocturnal seizure frequency, as assessed by an audio/video detection system (Nelli), at each postdose timepoint |
| **Safety** | |
| To further characterize the safety and tolerability of Compound 1 in pediatric participants with DEEs using additional safety variables | Changes from baseline in vital sign measurements<br>Changes from baseline in clinical laboratory results<br>Changes from baseline in electrocardiogram (ECG) parameters<br>Incidence of suicidal ideation or behavior, as measured by the Columbia-Suicide Severity Rating Scale (C-SSRS) (only for participants aged >7 years) |

PART B: OPEN-LABEL EXTENSION

| Objective | Endpoint |
|---|---|
| **Primary** | |
| To evaluate the long-term safety and tolerability of Compound 1 in pediatric participants with DEEs | Incidence and severity of TEAEs |
| **Secondary** | |
| To assess the effect of Compound 1 on the frequency of countable motor seizures in pediatric participants with DEEs | Changes from baseline in monthly (28-day) motor seizure frequency |
| To characterize the PK of Compound 1 oral suspension in pediatric participants with DEEs | Plasma concentrations of Compound 1 |
| **Exploratory** | |
| To explore the effect of Compound 1 on additional efficacy outcomes in pediatric participants with DEEs | Changes from baseline in other types of seizures<br>CGI-I score at each postdose timepoint<br>CgGI-I score at each postdose timepoint |
| **Safety** | |
| To further characterize the long-term safety and tolerability of Compound 1 in pediatric participants with DEEs using additional safety variables | Changes from baseline in vital sign measurements<br>Changes from baseline in clinical laboratory results<br>Changes from baseline in ECG parameters<br>Incidence of suicidal ideation or behavior, as measured by the C-SSRS (only for participants aged >7 years) |

Part A

Screening Period

Prior to the initiation of any study procedures, participants will provide written informed consent/assent. The Screening Period will be up to 6 weeks in duration, including the 28-day Baseline Observation Period. The Screening Period can be extended by up to an additional 2 weeks to complete all screening procedures if needed and approved by the sponsor medical director.

After completing the screening assessments, participants will begin the 28-day Baseline Observation Period. At the beginning of the Screening Period, participants will be given an electronic diary to record countable motor seizure frequency daily (as defined in the trial inclusion criteria) and, where locally permitted, an audio/visual device (Nelli) to monitor for nocturnal seizure activity. The countable motor seizure data recorded in the diary during this 28-day observation period will be used to determine eligibility for the clinical trial and to establish a baseline for efficacy analyses. In addition, a baseline video electroencephalogram (vEEG) will be performed during the Screening Period.

Double-Blind Treatment Period

The Double-Blind Treatment Period will be 16 weeks in duration. Participants will return to the clinic on Day 1 for additional baseline assessments and confirmation of eligibility. Participants who continue to meet all trial entry criteria will be enrolled into the appropriate cohort based on their clinical diagnosis (SCN2A-DEE or SCN8ADEE). Participants in each cohort will be randomly assigned in a double-blind manner (1:1 ratio) to receive either Compound 1 once daily (QD) for 16 weeks (Compound 1 arm) or Compound 1 QD for 12 weeks and matching placebo QD for 4 weeks (Compound 1/placebo arm). Participants randomized to the Compound 1/placebo arm will receive placebo for 4 consecutive weeks at some point during the 16-week Treatment Period.

The starting dose of study drug for all participants in the Double-Blind Treatment Period will be 0.5 mg/kg/day, administered orally or via gastrostomy/jejunostomy tube (G/J-tube). The dose level(s) of concomitant SCBs (if applicable) and study drugs will be adjusted for tolerability and/or efficacy as described below. The dose levels of other ASMs and pertinent concomitant medications should remain unchanged during the Double-Blind Treatment Period.

Safety Follow-Up Period

After completing the Double-Blind Treatment Period, participants may choose to either discontinue study drug dosing or continue into the long-term OLE Treatment Period (in Part B) to receive Compound 1 for an additional 48 weeks. Participants who choose to not roll over to the OLE Treatment Period will discontinue study drug at Week 16/end of treatment (EOT) and then continue into the Safety Follow-up Period (in Part A). At the end of the Safety Follow-up Period, all participants will complete a Safety Follow-up Visit at Week 20/end of study (EOS).

Part B

Open-Label Extension Treatment Period

Participants who complete the Double-Blind Treatment Period (in Part A) and choose to continue study drug treatment will enter the OLE Treatment Period (in Part B). The OLE Treatment Period will be 48 weeks in duration.

Prior to the initiation of any study procedures, participants will provide written informed consent/assent. Visit 1 (Day 1) of the OLE Treatment Period will be the End-of-Treatment Visit of the Double-Blind Treatment Period (in Part A); participants who enter the OLE Treatment Period will have uninterrupted treatment with study drug.

During the OLE Treatment Period, participants will continue to receive the study drugs at home QD. Study drugs should be administered at approximately the same time each day and can be administered without regard to food.

Participants who roll over to the OLE Treatment Period will continue to receive the same dose of Compound 1 as the last dose they received in Part A which was not associated with severe or moderate tolerability issues. The dose of Compound 1 may be adjusted for tolerability and/or efficacy as described below. The dose level(s) of concomitant medications (including ASMs or and other pertinent medications) may be adjusted at the investigator's discretion during the OLE Treatment Period.

Safety Follow-Up Period

After completing the OLE Treatment Period, participants will continue into the Safety Follow-up Period (in Part B). During this 4-week follow-up period, the participant's concomitant medications (including ASMs or other pertinent medications) may be adjusted at the investigator's discretion. It is recommended that the investigator reinitiate the participant's baseline dose of SCB, if it was decreased, at least 1 week after discontinuation of Compound 1, given the approximately 4-day half-life of Compound 1. At the end of the Safety Follow-up Period, all participants will complete a Safety Follow-up Visit at Week 52/EOS.

Dose Modification

For each participant, the starting dose of the study drug in the Double-Blind Treatment Period will be calculated based on the participant's weight on Day 1 in Part A. At Week 8 of the Double-Blind Treatment Period in Part A and at Weeks 16, 32, and 48 of the OLE Treatment Period in Part B, the study drug dose can be adjusted, if needed, based on the participant's weight at these visits.

Part A

Beginning on Day 1 of the Double-Blind Treatment Period in Part A, each participant will receive study drug at a starting dose of 0.5 mg/kg/day, administered QD orally or via G/J-tube. During the Double-Blind Treatment Period, the dose level(s) of concomitant SCBs or study drug will be adjusted for tolerability and/or efficacy, as further described below.

The dose levels of other ASMs and pertinent concomitant medications should remain unchanged during the Double-Blind Treatment Period.

Dose Modification for Efficacy During the Double-Blind Treatment Period

At Week 8 of the Double-Blind Treatment Period in Part A, if a participant has a <30% decrease in the number of seizures in the preceding 4 weeks compared with during the 28-day Baseline Observation Period and has no tolerability issues, the study drug dose will be increased to 1.0 mg/kg/day. This will be the maximum dose allowed in this trial.

Part B

Participants who roll over to the OLE Treatment Period will continue to receive the same dose of Compound 1 as the last dose they received in Part A which was not associated with severe or moderate tolerability issues. The dose of Compound 1 may be increased by increments of 0.25 mg/kg/day every 4 weeks up to a maximum of 1.0 mg/kg/day for efficacy at the discretion of the investigator. If tolerability issues arise, the dose of Compound 1 or concomitant SCB can be down-titrated as outlined for the Double-Blind Treatment Period of Part A above.

The dose level(s) of concomitant medications (including ASMs or other pertinent medications) may be adjusted at the investigator's discretion during the OLE Treatment Period.

Treatment Emergent Adverse Events

An AE is any untoward medical occurrence in a patient or clinical trial participant, temporally associated with the use of the study drug, whether or not considered related to the study drug. Events meeting the definition of an adverse event may include:

- Any abnormal laboratory test results (hematology, clinical chemistry, or urinalysis) or other safety assessments (eg, ECG, radiological scans, or vital signs measurements), including those that worsen from baseline, are considered clinically significant in the medical and scientific judgment of the investigator (ie, not related to the progression of underlying disease).
- Exacerbation of a chronic or intermittent pre-existing condition including either an increase in frequency and/or intensity of the condition.
- New conditions detected or diagnosed after study drug administration even though it may have been present before the start of the clinical trial.
- Signs, symptoms, or the clinical sequelae of a suspected drug-drug interaction.
- Signs, symptoms, or the clinical sequelae of a suspected overdose of either a study drug or a concomitant medication. Overdose per se will not be reported as an AE/SAE, unless it is an intentional overdose taken with possible suicidal/self-harming intent. Such overdoses should be reported regardless of sequelae.
- For efficacy studies: "Lack of efficacy" or "failure of expected pharmacological action" per se will not be reported as an AE or SAE. Such instances will be captured in the efficacy assessments. However, the signs, symptoms, and/or clinical sequelae resulting from lack of efficacy will be reported as AE or SAE if they fulfill the definition of an AE or SAE.

The each AE and SAE reported during the clinical trial will be assigned to one of the following categories:

Mild: An event that is easily tolerated by the participant, causing minimal discomfort and not interfering with everyday activities.

Moderate: An event that causes sufficient discomfort and interferes with normal everyday activities.

Severe: An event that prevents normal everyday activities. An AE that is assessed as severe should not be confused with an SAE. Severe is a category utilized for rating the intensity of an event; and AEs, AESIs, and SAEs can be assessed as severe.

Seizure Diary

An electronic diary will be used to record countable motor seizure frequency daily during the clinical trial. In addition, study drug dosing and concomitant medication information will also be recorded in this diary.

The parent/legal guardian for each participant will record seizure frequency in the electronic diary daily during the Screening Period, ensuring at minimum 28-days of data is collected during the Baseline Observation Period, and then daily throughout the Double-Blind Treatment Period in Part A and daily for at least 1 week before each clinic visit during the OLE Treatment Period in Part B. The countable motor seizure data recorded during the 28-day Baseline Observation Period will be used to determine eligibility for the clinical trial and to establish a baseline for efficacy analyses. Prompts may be used to ensure adequate data capture in addition to spontaneous reporting. The diary will be completed by the same parent/legal guardian as often as possible.

Video Electroencephalogram

To the extent allowed by local regulations, a vEEG will be performed by a trained technician to record brainwave activity and evaluated for changes over time. The vEEG can be completed at home or in-clinic, ideally with a minimum of 1 hour and up to 24 hours of continuous recording.

Audio/Video-Based Seizure Detection (Nelli)

Where locally permitted, a video/audio-based automated detection system (Nelli) will be used to collect and quantify motion and sound activity that would suggest seizure behavior in the participants. The Nelli system will be placed in the participant's home when feasible and audio/video data will be collected through the duration of the clinical trial. The audio/video data will be analyzed semiautomatically to classify nocturnal seizures by selecting relevant epochs for subsequent review by human experts.

Clinical Global Impression-Severity and Clinical Global Impression-Improvement

The CGI scale was developed for use in National Institutes of Health-sponsored clinical trials in individuals with mental health disorders. The CGI scale provides an overall assessment of improvement over a specified period. The scale includes two, 7-point Likert rating scales: the CGI-S and CGI-I scales. The CGI scale will be anchored with reference to domains/symptoms experienced by participants with SCN2A-DEE or SCN8A-DEE. Participants will be assessed by the clinician at on Baseline (Day 1) and at the End-of-Treatment Visit for the severity of SCN2A-DEE or SCN8A-DEE symptoms using the CGI-S. Change from baseline in SCN2A-DEE or SCN8A-DEE symptoms will be assessed by the clinician using the CGI-I.

Caregiver Global Impression-Severity and Caregiver Global Impression-Improvement The Caregiver Global Impression-Severity (CgCGI-S) and CgCGI-I scales are similar to the CGI-S and CGI-I scales, respectively. Participants will be assessed by the caregiver at Baseline (Day 1) for the severity of their SCN2A-DEE or SCN8A-DEE symptoms using the CgGI-S. Change from baseline in SCN2A-DEE or SCN8A-DEE symptoms will be assessed by the caregiver using the CgGI-I.

Physical Examinations

A complete physical examination will include, at a minimum, assessments of the cardiovascular, respiratory, gastrointestinal, and neurological systems.

Electrocardiograms

Twelve-lead ECGs will be obtained using an ECG machine that automatically calculates the heart rate and measures PR, QRS, QT, and corrected QT intervals. Participants should rest for at least 5 minutes prior to ECG measurements. Triplicate measurements will be taken at Screening and all other timepoints in Part A and single measurements will be taken at all timepoints in Part B, as indicated in the SoAs. When triplicate ECGs are required, 3 individual ECG tracings should be obtained as closely as possible in succession, but no more than 2 minutes apart.

Pharmacokinetic Assessments

Whole blood samples will be collected for the measurement of plasma concentrations of Compound 1. Samples collected may also be used to evaluate the safety or efficacy aspects related to concerns arising during or after the clinical trial. Samples may also be used for additional exploratory method development and/or metabolite characterization purposes.

Example 14

To test the anticonvulsant activity of compound 1 in vivo, compound 1 was administered to developmental and epileptic encephalopathy (DEE) mouse models with mutations in Scn2a and Scn8a genes. The Scn2a mutant mice mice had Q54 mutation and Scn8a mice had N1768D mutation.

Figure 14A:
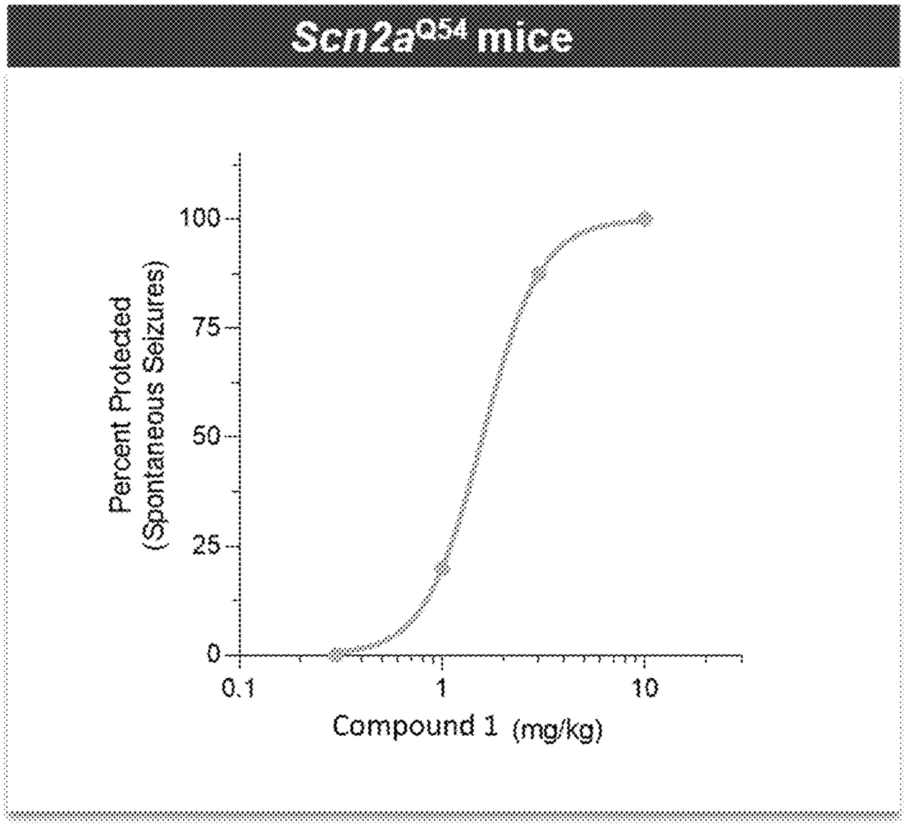
FIG. 14A is a graph showing percent protection from spontaneous seizures in Scn2a DEE mouse model as a function of the administered dose of Compound 1.
Figure 14B:
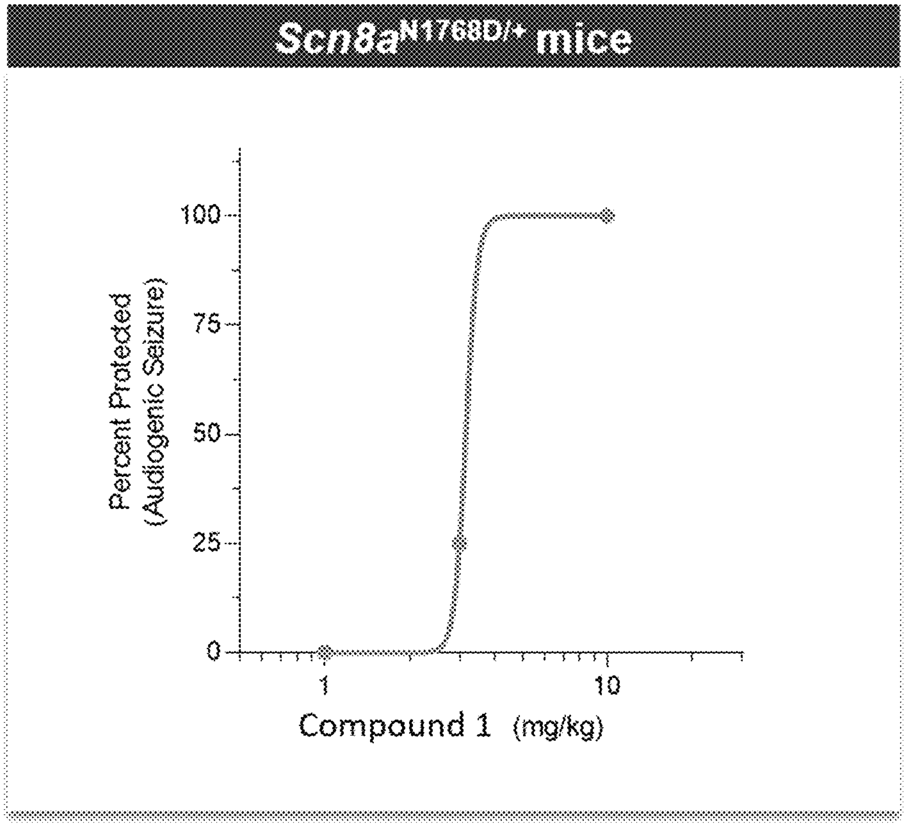
FIG. 14B is a graph showing percent protection from spontaneous seizures in Scn8a DEE mouse model as a function of the administered dose of Compound 1.

FIG. 14A is a graph showing percent protection from spontaneous seizures in Scn2a DEE mouse model as a function of the administred dose of Compound 1. FIG. 14B is a graph showing percent protection from spontaneous seizures in Scn8a DEE mouse model as a function of the administred dose of Compound 1. The results shown in FIGS. 14A and 14B indicate that Compound 1 has potent anticonvulsant activity and can completely block seizures in Scn2a and Scn8a DEE mouse models.

The anticonvulsant activities of Compound 1 were also tested in non-$Na_V$ DEE mouse models. Specifically, Compound 1 was tested in pentylenetetrazole-induced seizure (PTZ) mouse models having mutations in Kcnq2, Kcnc1, and Hcn1 genes. The Kcnq2 mice had K556E mutation, the Kcnc1 mice had R320H mutation, and Hcn1 mice had M305L mutation.

Figure 14C:
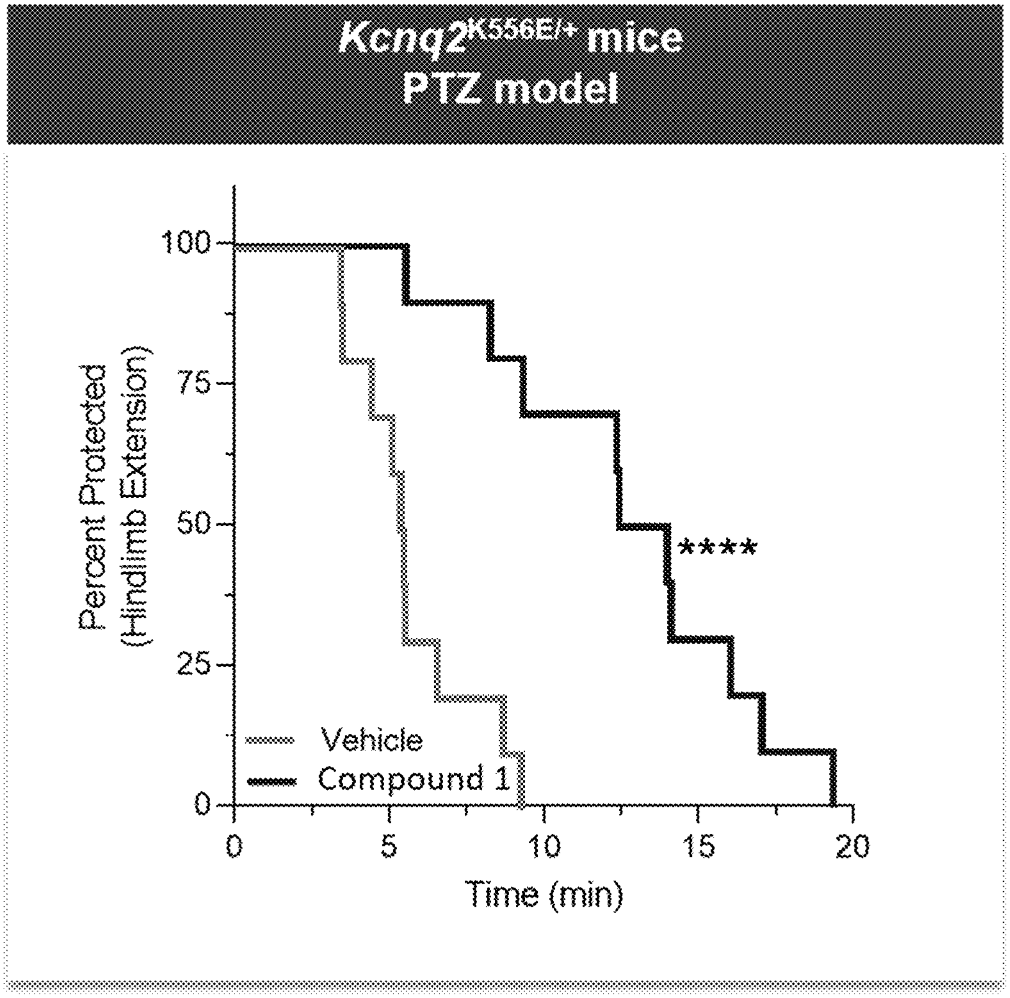
FIG. 14C is a graph showing percent protection from hindlimb extension as a function of time in Kcnq2 DEE mouse model administered vehicle or Compound 1.
Figure 14D:
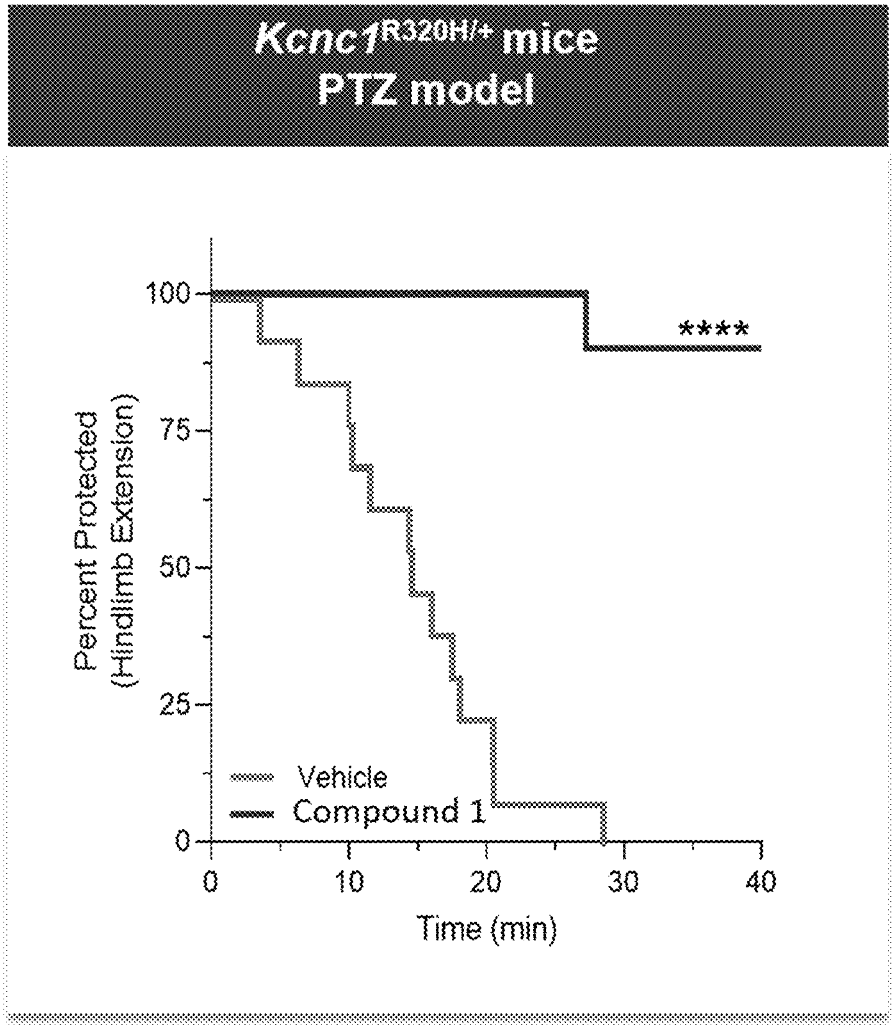
FIG. 14D is a graph showing percent protection from hindlimb extension as a function of time in Kcnc1 DEE mouse model administered vehicle or Compound 1.
Figure 14E:
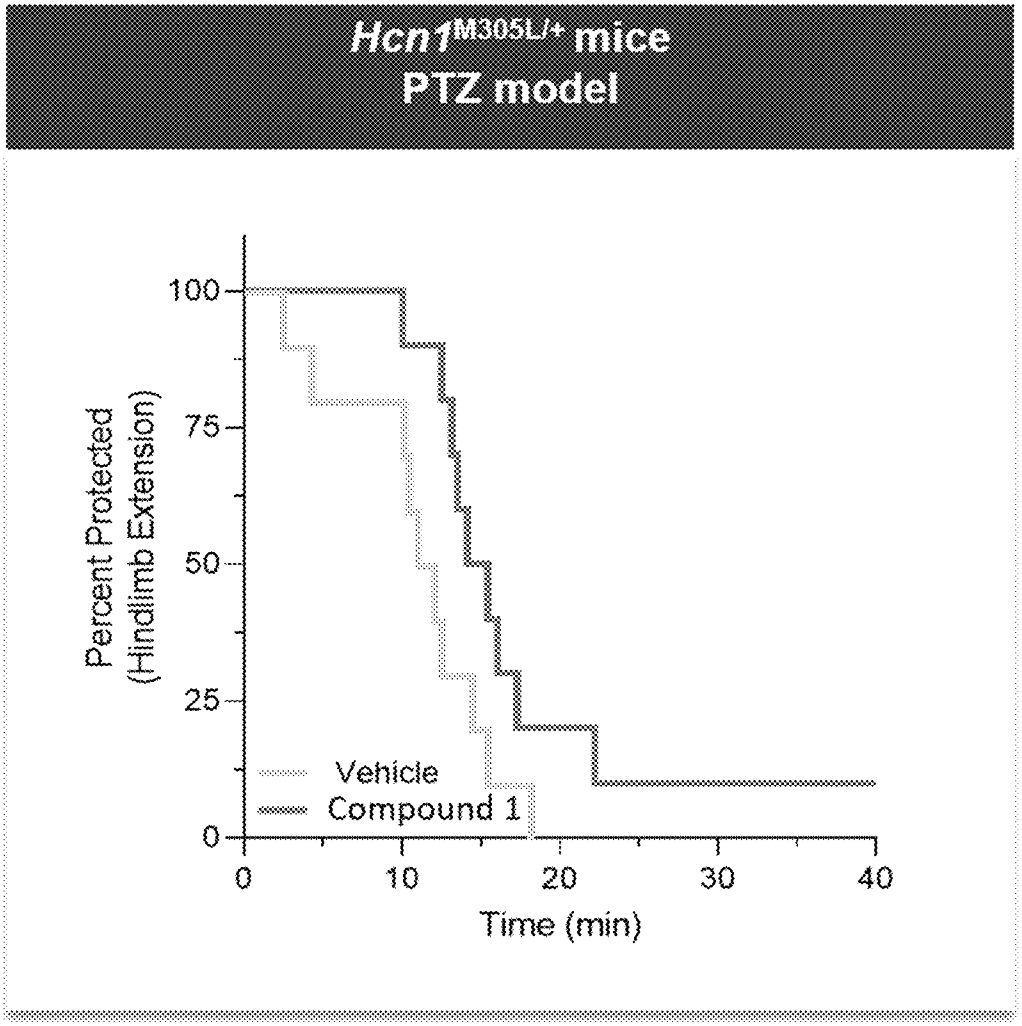
FIG. 14E is a graph showing percent protection from hindlimb extension as a function of time in Hcn1 DEE mouse model administered vehicle or Compound 1.

FIG. 14C is a graph showing percent protection from hindlimb extension as a function of time in Kcnq2 DEE mouse model administered vehicle or Compound 1. FIG. 14D is a graph showing percent protection from hindlimb extension as a function of time in Kcnc1 DEE mouse model administered vehicle or Compound 1. FIG. 14E is a graph showing percent protection from hindlimb extension as a function of time in Hcn1 DEE mouse model administered vehicle or Compound 1. The results presented in FIGS. 14A-14C indicate that Compound 1 exhibits robust anticonvulsant activity across mechanistically divergent models of human epilepsy.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all constructs, methods, and/or component features, steps, elements, or other aspects thereof can be used in various combinations.

Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or the entire group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. In general, where embodiments or aspects of the disclosure, is/are referred to as comprising particular elements, features, etc., certain embodiments or aspects consist, or consist essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification.

All patents, patent applications, websites, other publications or documents, accession numbers and the like cited herein are incorporated by reference in their entirety for all purposes to the same extent as if each individual item were specifically and individually indicated to be so incorporated by reference.

We claim:

1. A method for treating a genetic epilepsy or a genetic epilepsy syndrome in a human in need thereof, wherein the method comprises administering to the human a therapeutically effective amount of Compound 1 of the following formula:

Compound 1

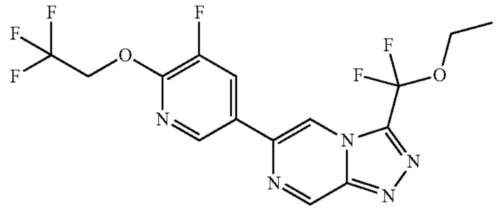

or a pharmaceutically acceptable salt thereof;

wherein Compound 1, or a pharmaceutically acceptable salt thereof, is administered to the human in need thereof in a therapeutically effective dosage amount in the range of 0.1 mg/kg/day to 10 mg/kg/day; and wherein the administration of the therapeutically effective dosage amount of Compound 1, or a pharmaceutically acceptable salt thereof, to the human in need thereof results in any one of (a), (b), (c), (d), (e), (f), or (g);

(a) a reduction in the severity of seizures experienced by the human as compared to the severity of seizures experienced by the human prior to administration of Compound 1, or a pharmaceutically acceptable salt thereof; or (b) a reduction in the number of seizures experienced by the human as compared to the number of seizures experienced by the human prior to administration of Compound 1, or a pharmaceutically acceptable salt thereof; or (c) a reduction in the frequency of seizures experienced by the human as compared to the frequency of seizures experienced by the human prior to administration of Compound 1, or a pharmaceutically acceptable salt thereof; or (d) a reduction in the severity of seizures experienced by the human as compared to the severity of seizures experienced by the human prior to administration of Compound 1, or a pharmaceutically acceptable salt thereof; and a reduction in the number of seizures experienced by the human as compared to the number of seizures experienced by the human prior to administration of Compound 1, or a pharmaceutically acceptable salt thereof; or (e) a reduction in the severity of seizures experienced by the human as compared to the severity of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof; or (f) a reduction in the number of seizures experienced by the human as compared to the number of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof; or (g) a reduction in the severity of seizures experienced by the human as compared to the severity of seizures experienced by the human prior to administration of Compound 1, or a pharmaceutically acceptable salt thereof;

a reduction in the number of seizures experienced by the human as compared to the number of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof.

2. The method of claim 1, wherein the genetic epilepsy or the genetic epilepsy syndrome is selected from the group consisting of KCNQ2 epileptic encephalopathy, KCNT1 epileptic encephalopathy, SCN1A epileptic encephalopathy, SCN2A epileptic encephalopathy, cryptogenic pediatric partial epilepsy with SCN3A mutation, focal epilepsy with SCN3A mutation, and SCN8A epileptic encephalopathy.

3. The method of claim 2, wherein the SCN1A epileptic encephalopathy is Dravet syndrome with SCN1A mutation.

4. The method of claim 2, wherein the genetic epilepsy or the genetic epilepsy syndrome is SCN2A epileptic encephalopathy or SCN8A epileptic encephalopathy.

5. The method of claim 1, wherein the genetic epilepsy or the genetic epilepsy syndrome is a pediatric epilepsy or a pediatric epilepsy syndrome.

6. The method of claim 1, wherein Compound 1, or a pharmaceutically acceptable salt thereof, is administered to the human in a therapeutically effective dosage amount in the range of 0.25 mg/kg/day to 1 mg/kg/day.

7. The method of claim 1, wherein Compound 1, or a pharmaceutically acceptable salt thereof, is administered to the human in a therapeutically effective dosage amount selected from the group consisting of (a), (b), (c), (d), (e), (f), (g), (h), (i), (j), (k), (l), (m), (n), (o), and (p):

(a) 0.25 mg/kg/day;
(b) 0.30 mg/kg/day;
(c) 0.35 mg/kg/day;
(d) 0.40 mg/kg/day;
(e) 0.45 mg/kg/day;
(f) 0.50 mg/kg/day;
(g) 0.55 mg/kg/day;
(h) 0.60 mg/kg/day;
(i) 0.65 mg/kg/day;
(j) 0.70 mg/kg/day;
(k) 0.75 mg/kg/day;
(l) 0.80 mg/kg/day;
(m) 0.85 mg/kg/day;
(n) 0.90 mg/kg/day;
(o) 0.95 mg/kg/day; and
(p) 1.0 mg/kg/day.

8. The method of claim 7, wherein Compound 1, or a pharmaceutically acceptable salt thereof, is administered to the human in a therapeutically effective dosage amount selected from the group consisting of (a), (f), and (p):

(a) 0.25 mg/kg/day;
(f) 0.50 mg/kg/day; and
(p) 1.0 mg/kg/day.

9. The method of claim 1, wherein Compound 1, or a pharmaceutically acceptable salt thereof, is administered orally or via a gastrostomy/jejunostomy tube (G/J-tube) to the human.

10. The method of claim 1, wherein the seizure is selected from the group consisting of an absence seizure, a clonic seizure, a focal seizure, a myoclonic seizure, an obtundation status seizure, and a tonic seizure, or a combination thereof.

11. The method of claim 10, wherein the clonic seizure is a generalized clonic seizure.

12. The method of claim 10, wherein the tonic seizure is a generalized tonic seizure.

13. The method of claim 1, wherein the seizure is a motor seizure.

14. The method of claim 1, wherein the human is a pediatric human.

15. A method for effecting any one of (a), (b), (c), (d), (e), (f), or (g) in a human having a genetic epilepsy or a genetic epilepsy syndrome, wherein the method comprises administering to the human in need thereof a therapeutically effective amount of Compound 1 of the following formula:

Compound 1

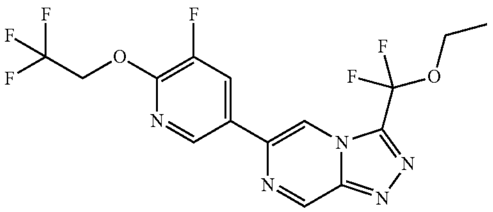

or a pharmaceutically acceptable salt thereof;

wherein (a), (b), (c), (d), (e), (f), or (g) is:

(a) a reduction in the severity of seizures experienced by the human as compared to the severity of seizures experienced by the human prior to administration of Compound 1, or a pharmaceutically acceptable salt thereof; or (b) a reduction in the number of seizures experienced by the human as compared to the number of seizures experienced by the human prior to administration of Compound 1, or a pharmaceutically acceptable salt thereof; or (c) a reduction in the frequency of seizures experienced by the human as compared to the frequency of seizures experienced by the human prior to administration of Compound 1, or a pharmaceutically acceptable salt thereof; or (d) a reduction in the severity of seizures experienced by the human as compared to the severity of seizures experienced by the human prior to administration of Compound 1, or a pharmaceutically acceptable salt thereof; and a reduction in the number of seizures experienced by the human as compared to the number of seizures experienced by the human prior to administration of Compound 1, or a pharmaceutically acceptable salt thereof; or (e) a reduction in the severity of seizures experienced by the human as compared to the severity of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof; or (f) a reduction in the number of seizures experienced by the human as compared to the number of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof; or (g) a reduction in the severity of seizures experienced by the human as compared to the severity of seizures experienced by the human prior to administration of Compound 1, or a pharmaceutically acceptable salt thereof;

a reduction in the number of seizures experienced by the human as compared to the number of seizures experienced by the human prior to administration of Compound 1, or a pharmaceutically acceptable salt thereof; and a reduction in the frequency of seizures experienced by the human as compared to the frequency of seizures experienced by the human prior to administration of Compound 1, or a pharmaceutically acceptable salt thereof; and wherein Compound 1, or a pharmaceutically acceptable salt thereof, is administered to the human in need thereof in a therapeutically effective dosage amount in the range of 0.1 mg/kg/day to 10 mg/kg/day.

16. The method of claim 15, wherein the genetic epilepsy or the genetic epilepsy syndrome is selected from the group consisting of KCNQ2 epileptic encephalopathy, KCNT1 epileptic encephalopathy, SCN1A epileptic encephalopathy, SCN2A epileptic encephalopathy, cryptogenic pediatric partial epilepsy with SCN3A mutation, focal epilepsy with SCN3A mutation, and SCN8A epileptic encephalopathy.

17. The method of claim 16, wherein the SCN1A epileptic encephalopathy is Dravet syndrome with SCN1A mutation.

18. The method of claim 16, wherein the genetic epilepsy or the genetic epilepsy syndrome is SCN2A epileptic encephalopathy or SCN8A epileptic encephalopathy.

19. The method of claim 15, wherein the genetic epilepsy or the genetic epilepsy syndrome is a pediatric epilepsy or a pediatric epilepsy syndrome.

20. The method of claim 15, wherein Compound 1, or a pharmaceutically acceptable salt thereof, is administered to the human in need thereof in a therapeutically effective dosage amount in the range of 0.25 mg/kg/day to 1 mg/kg/day.

21. The method of claim 20, wherein Compound 1, or a pharmaceutically acceptable salt thereof, is administered to the human in need thereof in a therapeutically effective dosage amount selected from the group consisting of (a), (b), (c), (d), (e), (f), (g), (h), (i), (j), (k), (l), (m), (n), (o), and (p):

(a) 0.25 mg/kg/day;
(b) 0.30 mg/kg/day;
(c) 0.35 mg/kg/day;
(d) 0.40 mg/kg/day;
(e) 0.45 mg/kg/day;
(f) 0.50 mg/kg/day;
(g) 0.55 mg/kg/day;
(h) 0.60 mg/kg/day;
(i) 0.65 mg/kg/day;
(j) 0.70 mg/kg/day;
(k) 0.75 mg/kg/day;
(l) 0.80 mg/kg/day;
(m) 0.85 mg/kg/day;
(n) 0.90 mg/kg/day;
(o) 0.95 mg/kg/day; and
(p) 1.0 mg/kg/day.

22. The method of claim 21, wherein Compound 1, or a pharmaceutically acceptable salt thereof, is administered to the human in need thereof in a therapeutically effective dosage amount selected from the group consisting of (a), (f), and (p):

(a) 0.25 mg/kg/day;
(f) 0.50 mg/kg/day; and
(p) 1.0 mg/kg/day.

23. The method of claim 15, wherein Compound 1, or a pharmaceutically acceptable salt thereof, is administered orally or via a gastrostomy/jejunostomy tube (G/J-tube) to the human in need thereof.

24. The method of claim 15, wherein the seizure is selected from the group consisting of an absence seizure, a clonic seizure, a focal seizure, a myoclonic seizure, an obtundation status seizure, and a tonic seizure, or a combination thereof.

25. The method of claim 24, wherein the clonic seizure is a generalized clonic seizure.

26. The method of claim 24, wherein the tonic seizure is a generalized tonic seizure.

27. The method of claim 15, wherein the seizure is a motor seizure.

28. The method of claim 15, wherein the human is a pediatric human.

* * * * *